(12) United States Patent
Tsourkas et al.

(10) Patent No.: US 11,446,391 B2
(45) Date of Patent: Sep. 20, 2022

(54) AMPHIPHILIC DYE-COATED INORGANIC NANOPARTICLE CLUSTERS

(71) Applicant: THE TRUSTEES OF THE UNIVERSITY OF PENNSYLVANIA, Philadelphia, PA (US)

(72) Inventors: Andrew Tsourkas, Bryn Mawr, PA (US); Jayesh Thawani, Houston, TX (US); Ahmad Amirshaghaghi, Philadelphia, PA (US); Lesan Yan, Philadelphia, PA (US); Zhiliang Cheng, Newtown, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/628,739

(22) PCT Filed: Jul. 5, 2018

(86) PCT No.: PCT/US2018/040951
§ 371 (c)(1),
(2) Date: Jan. 6, 2020

(87) PCT Pub. No.: WO2019/010329
PCT Pub. Date: Jan. 10, 2019

(65) Prior Publication Data
US 2020/0282076 A1    Sep. 10, 2020

Related U.S. Application Data

(60) Provisional application No. 62/529,065, filed on Jul. 6, 2017.

(51) Int. Cl.
| | | |
|---|---|---|
| *A61K 47/69* | (2017.01) | |
| *A61K 41/00* | (2020.01) | |
| *A61K 49/00* | (2006.01) | |
| *A61K 49/18* | (2006.01) | |
| *A61P 35/04* | (2006.01) | |
| *A61K 9/00* | (2006.01) | |
| *A61K 9/107* | (2006.01) | |

(52) U.S. Cl.
CPC ...... *A61K 47/6937* (2017.08); *A61K 41/0071* (2013.01); *A61K 47/6923* (2017.08); *A61K 49/0034* (2013.01); *A61K 49/0093* (2013.01); *A61K 49/1833* (2013.01); *A61P 35/04* (2018.01); *A61K 9/0019* (2013.01); *A61K 9/107* (2013.01)

(58) Field of Classification Search
None
See application file for complete search history.

(56) References Cited

U.S. PATENT DOCUMENTS

2009/0081295 A1    3/2009    Berkland et al.
2011/0288234 A1    11/2011   Pandey et al.

FOREIGN PATENT DOCUMENTS

WO    WO-2015183346 A2 *  12/2015  ......... A61K 49/0013
WO    WO 2016/200074 A    12/2016

OTHER PUBLICATIONS

El-Daly et al., Photodynamic therapeutic activity of indocyanine green entrapped in polymeric nanoparticles, Photodiagnosis and Photodynamic Therapy, vol. 10, No. 2, May 2013.
Thawani et al., Photoacoustic-Guided Surgery with Indocyanine Green-Coated Superparamagnetic Iron Oxide Nanoparticle Clusters, Small, vol. 13, No. 37, Jul. 27, 2017.
International Search Report for PCT/US2018/040951 dated Sep. 7, 2018.

* cited by examiner

Primary Examiner — Jennifer Lamberski
(74) Attorney, Agent, or Firm — Mark S. Cohen; Pearl Cohen Zedek Latzer Baratz LLP

(57) ABSTRACT

The invention relates to amphiphilic dye-coated inorganic nanoparticle clusters and uses thereof. Specifically, the invention relates to cyanine and/or cyclic tetrapyrrole dye-coated metallic nanoparticle clusters for use in medical imaging and treatments.

22 Claims, 34 Drawing Sheets

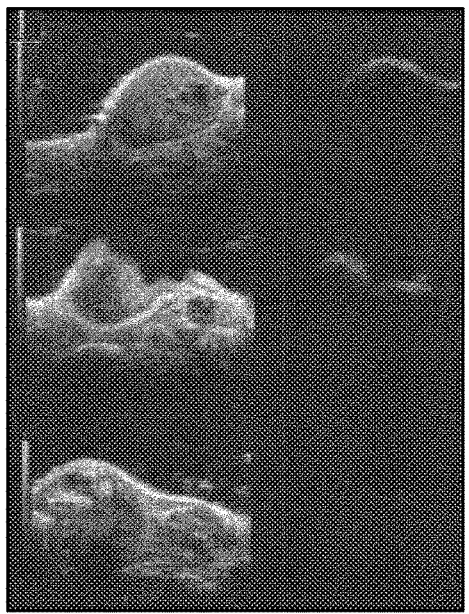 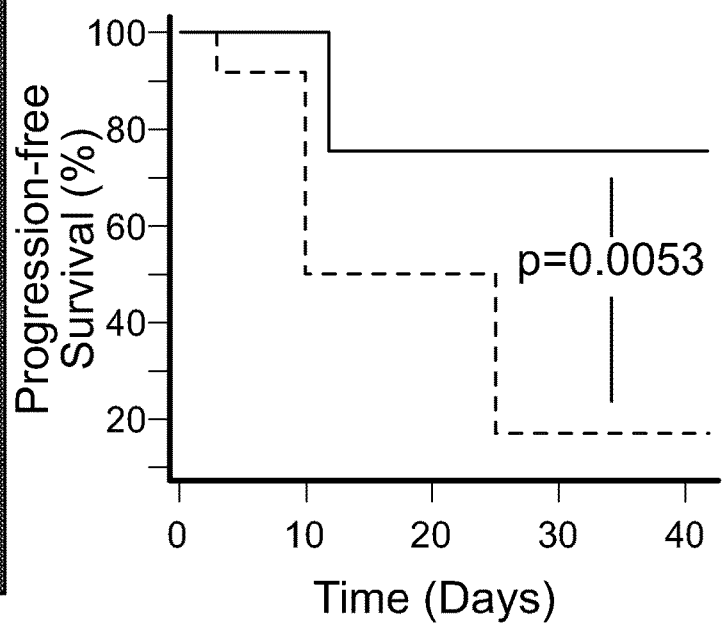
FIG. 11A          FIG. 11B
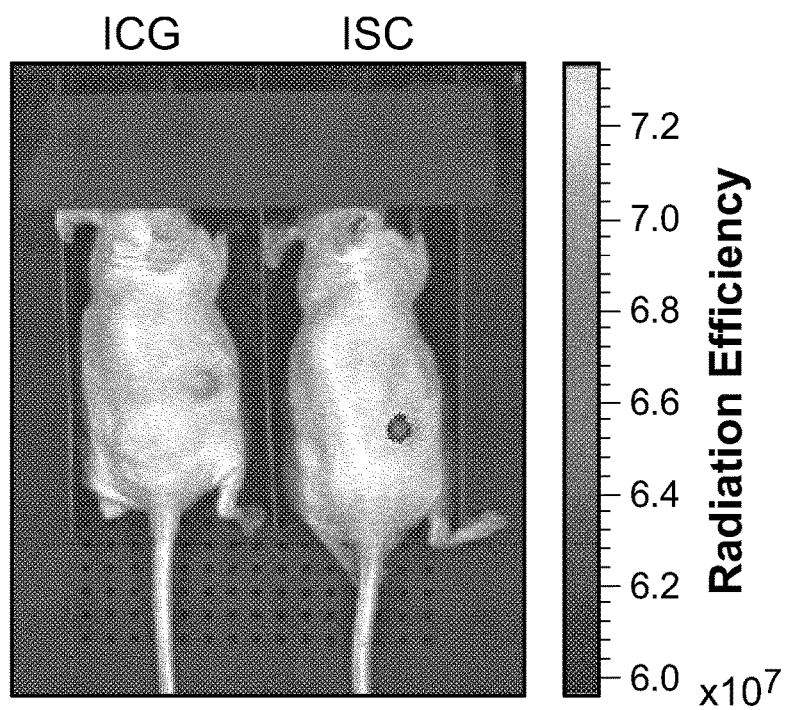
FIG. 12

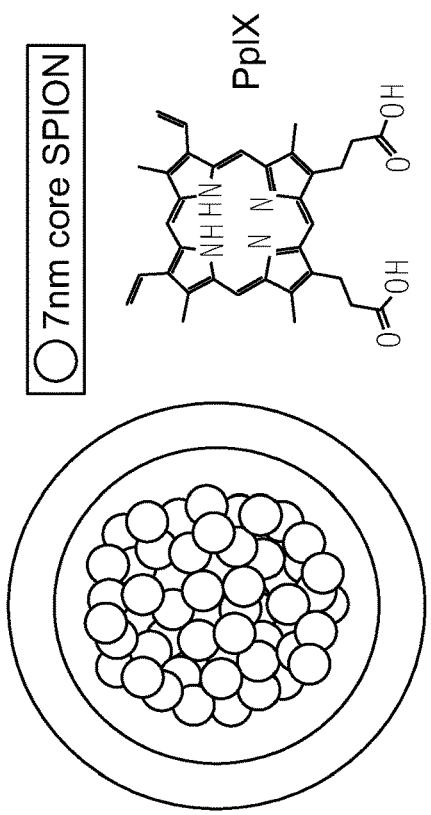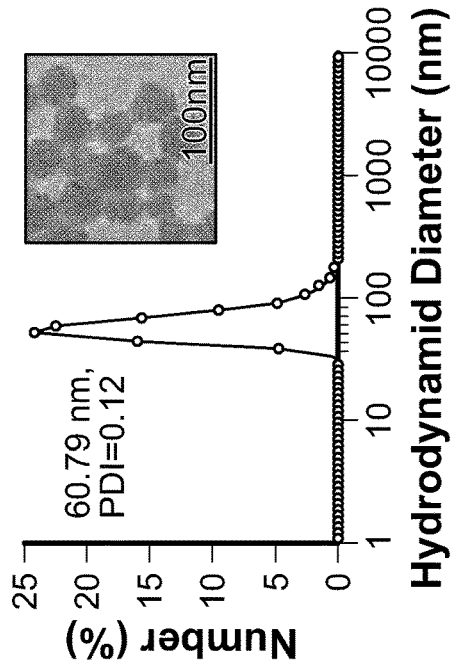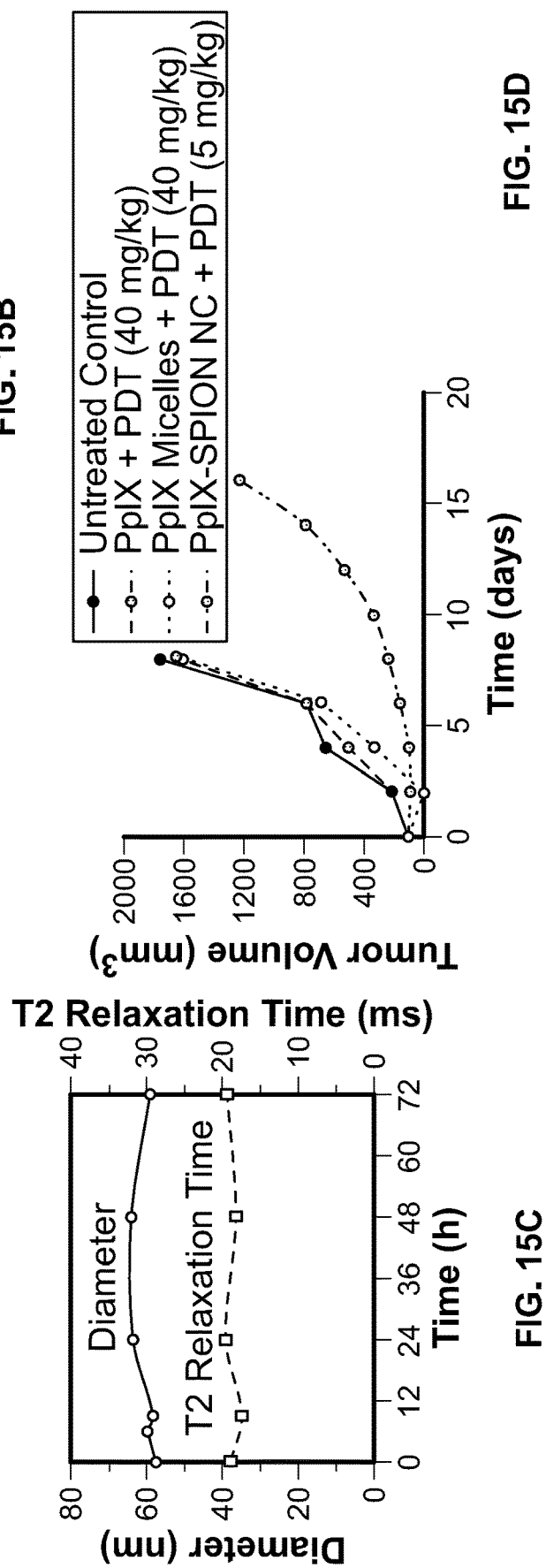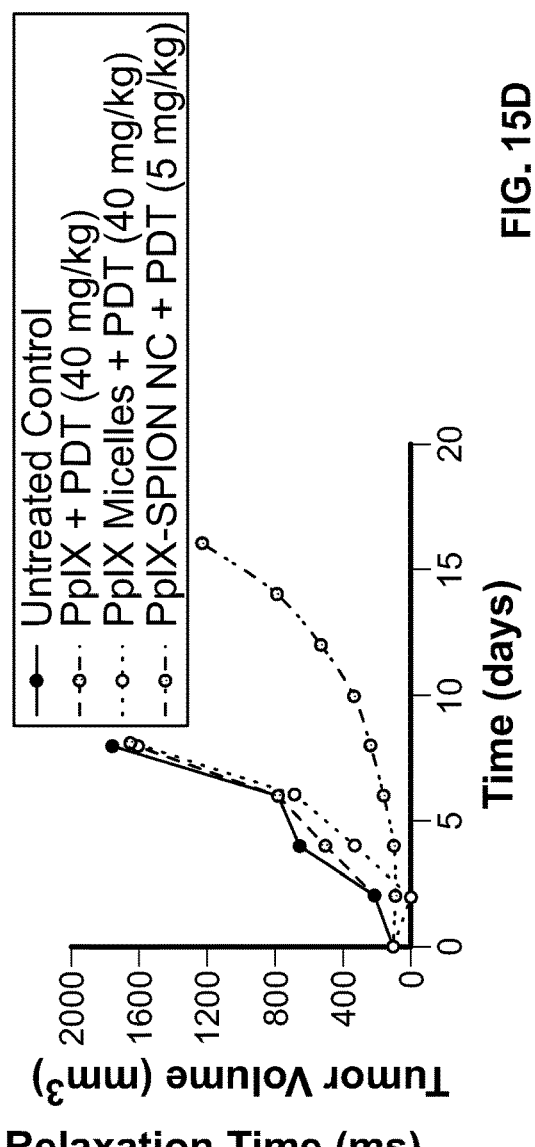
FIG. 15A
FIG. 15B
FIG. 15C
FIG. 15D

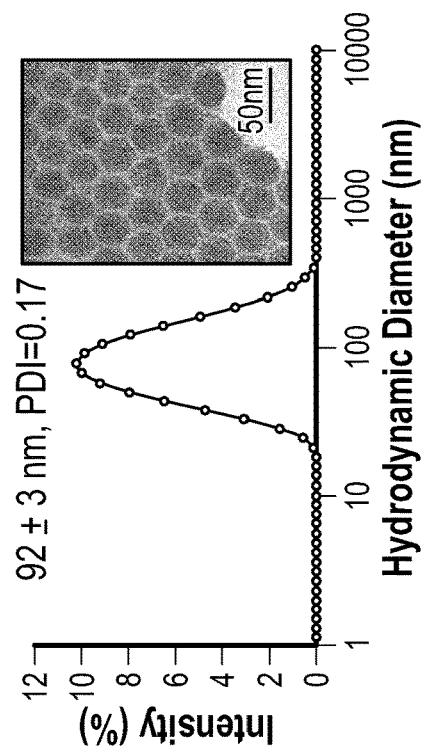
FIG. 22A
FIG. 22B
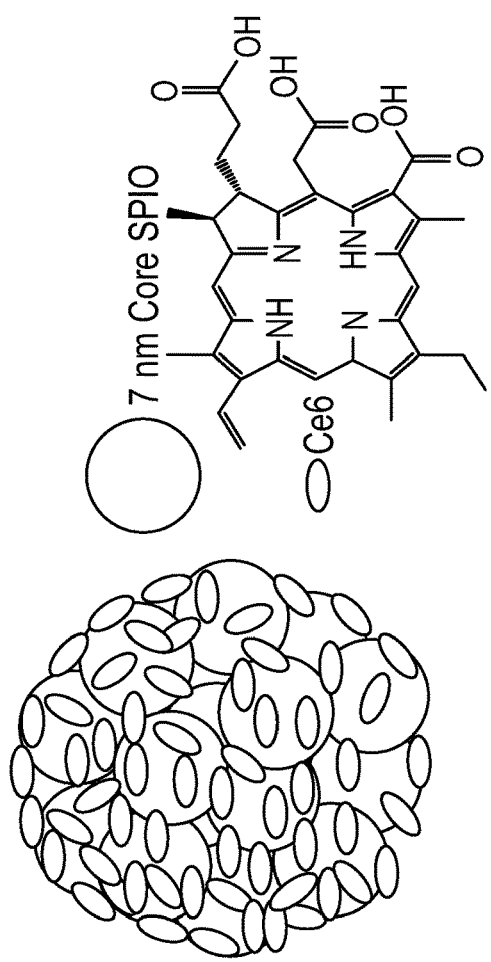
FIG. 22C
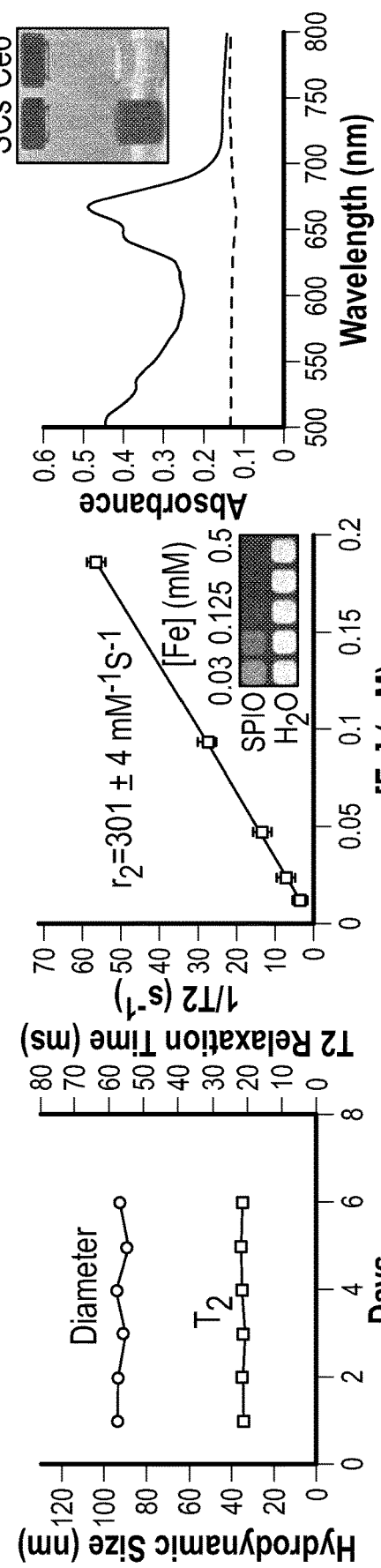
FIG. 22D
FIG. 22E

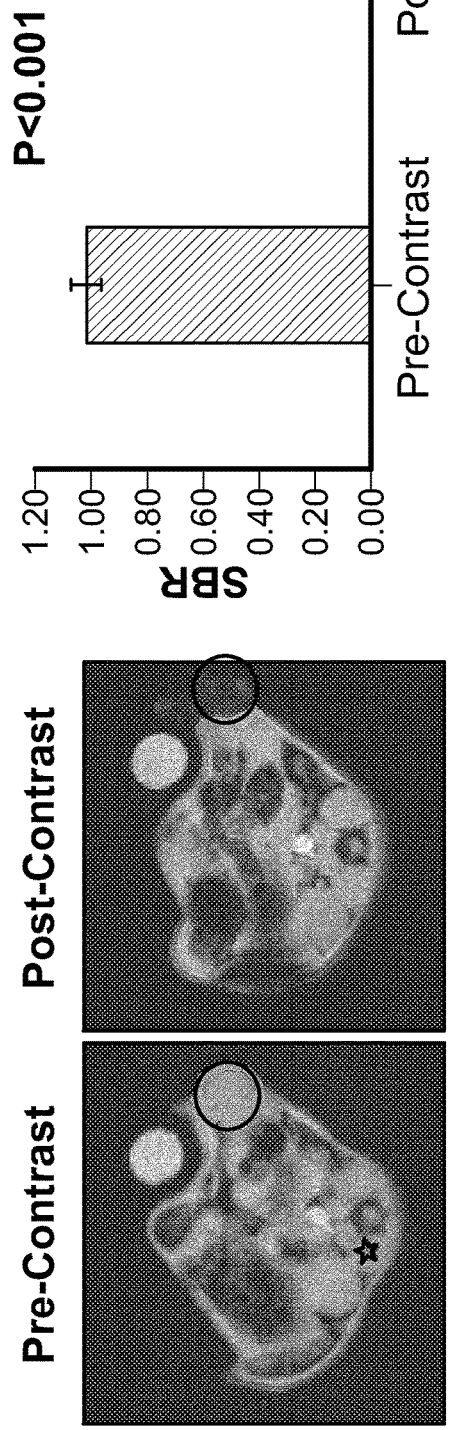
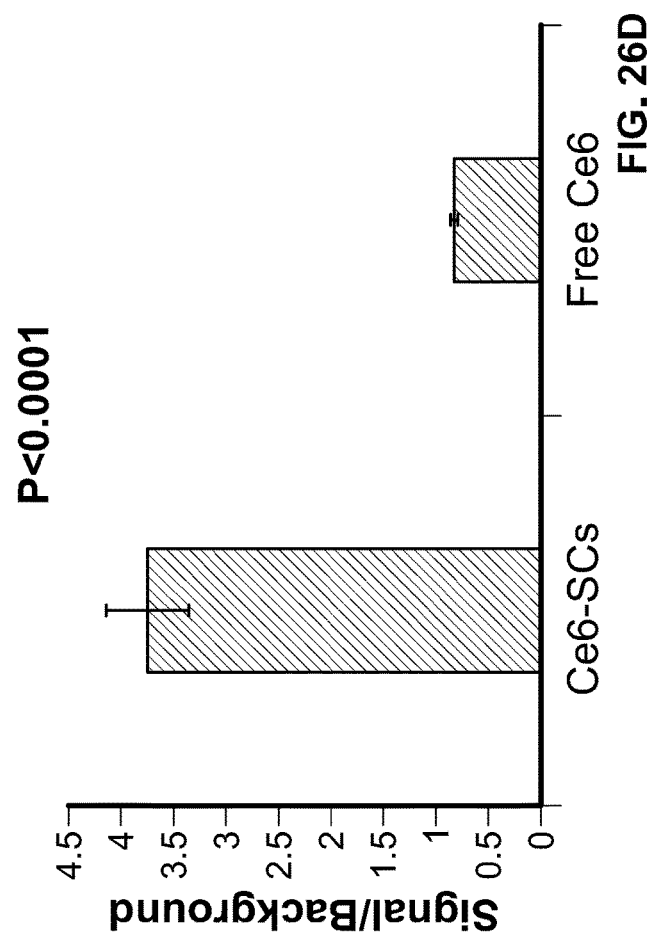
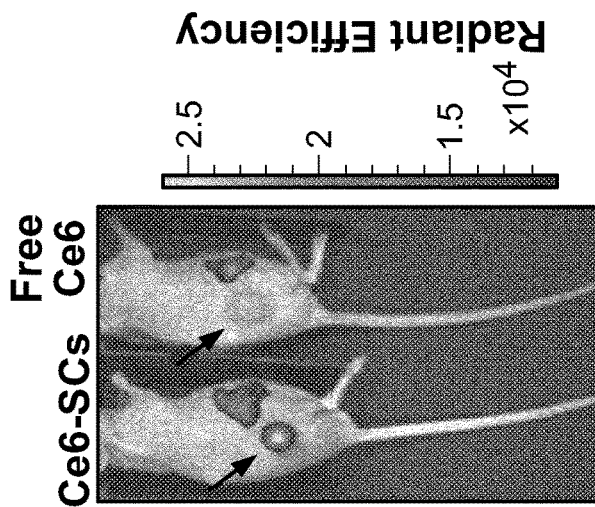
FIG. 26A
FIG. 26B
FIG. 26C
FIG. 26D

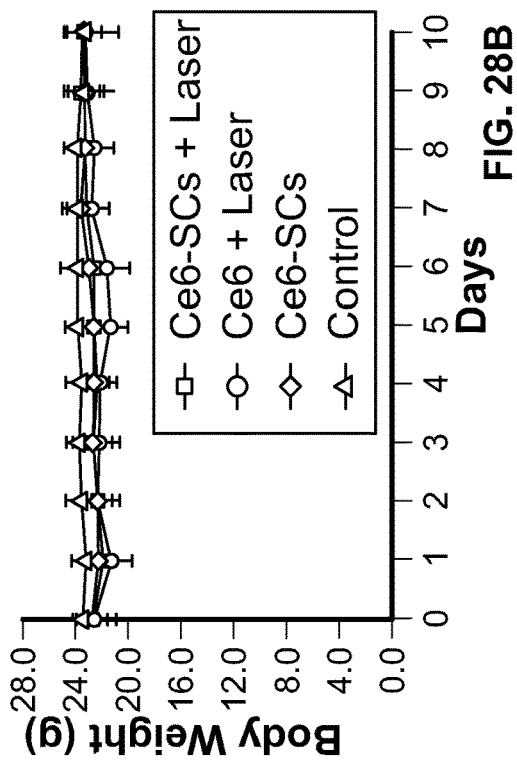
FIG. 28A
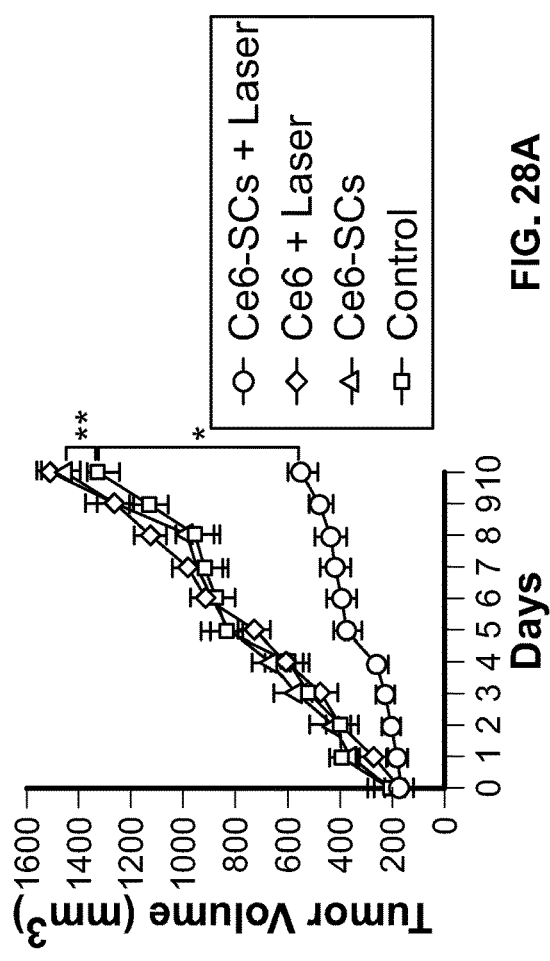
FIG. 28B
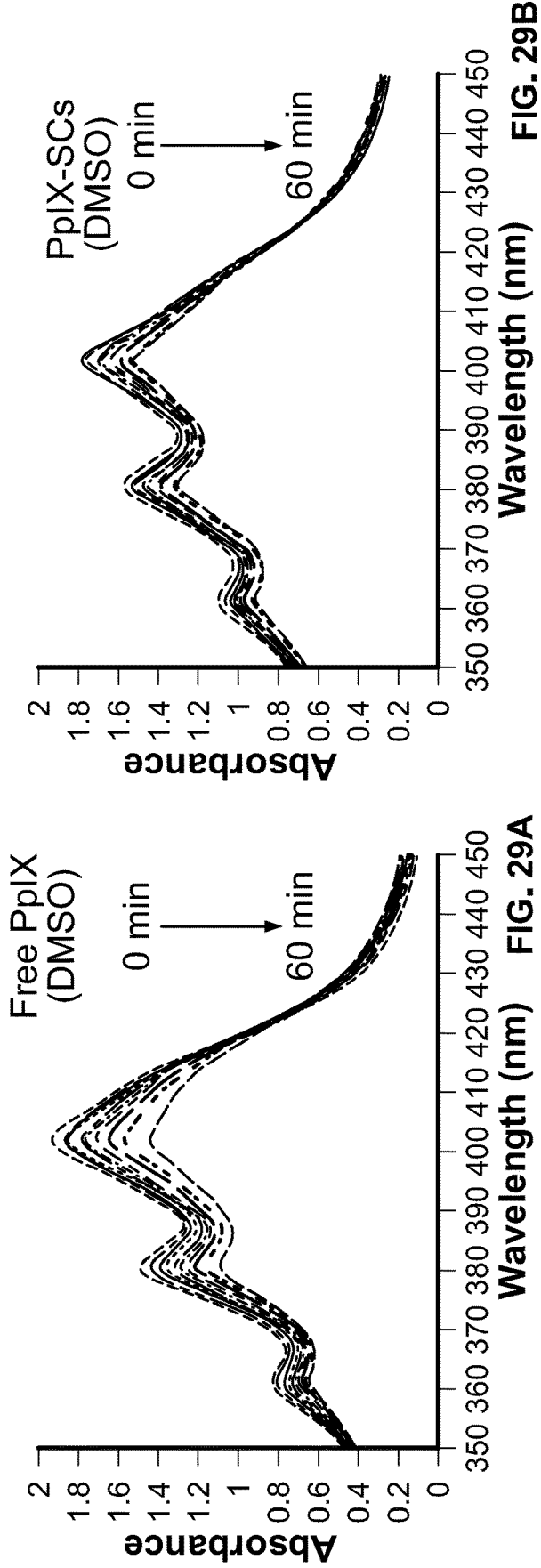
FIG. 29A
FIG. 29B

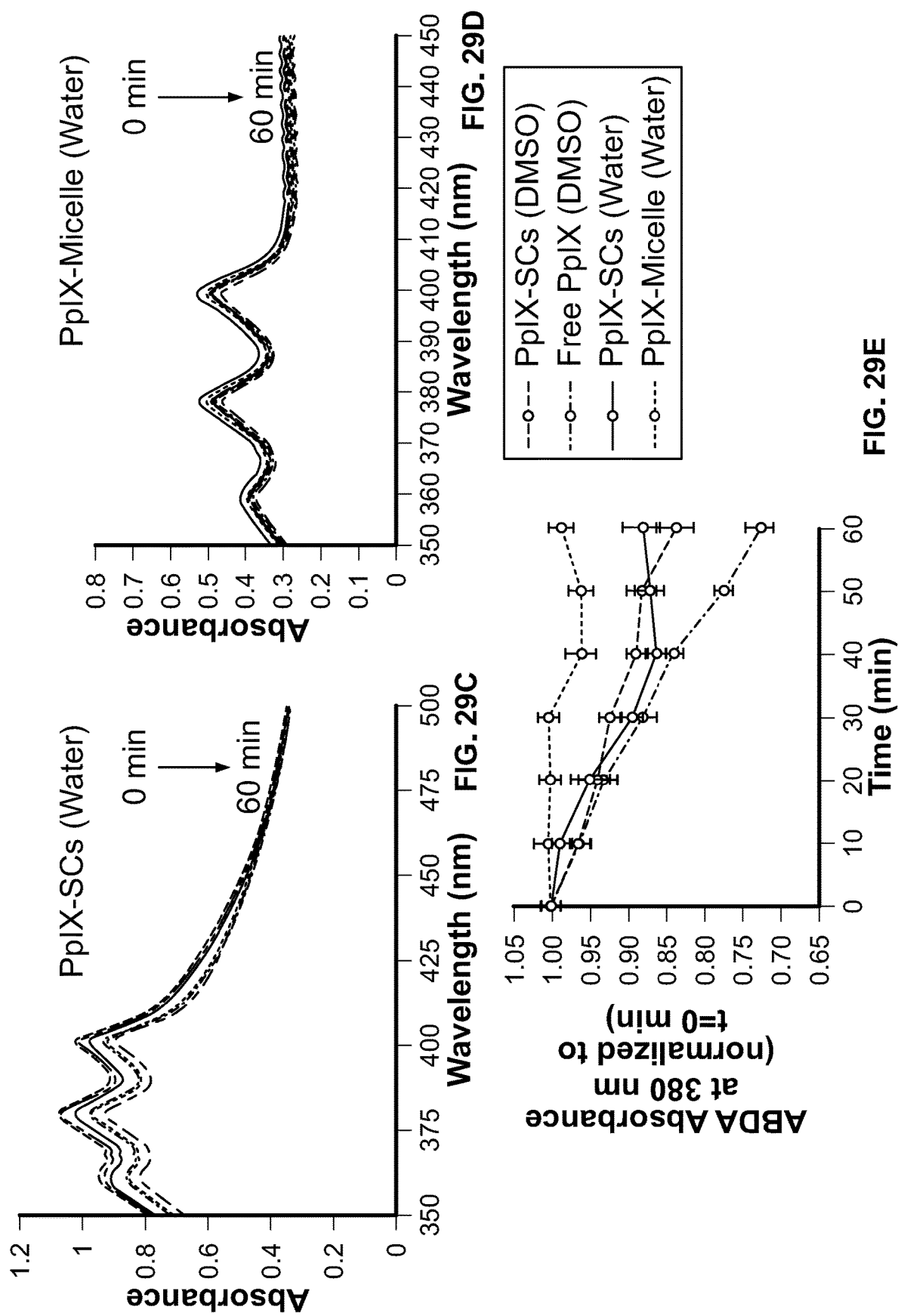

AMPHIPHILIC DYE-COATED INORGANIC NANOPARTICLE CLUSTERS

CROSS-REFERENCE TO RELATED APPLICATIONS

This application is a U.S. national stage application under 37 U.S.C. 371 of PCT International Application PCT/US18/40951, filed Jul. 5, 2018, which claims priority to and benefit of U.S. Provisional Patent Application 62/529,065, filed Jul. 6, 2017, all of which are incorporated by reference herein in their entirety.

GOVERNMENT INTEREST STATEMENT

This invention was made with government support, under Grant Numbers U01-EB016027, R01-CA181429, and R01-CA175480, awarded by the National Institutes of Health. The government has certain rights in the invention.

FIELD OF THE INVENTION

The invention relates to amphiphilic dye-coated inorganic nanoparticles or hydrophobic polymers and uses thereof. Specifically, the invention relates to cyanine and/or cyclic tetrapyrrole dye-coated metallic nanoparticles or hydrophobic polymers for use in various medical imaging and treatments.

BACKGROUND OF THE INVENTION

Numerous retrospective studies have found that increasing the extent of tumor resection and achieving gross total resection correlates with improved survival, for both initial surgery and recurrence. However, the heterogeneity, similarity of tumor appearance under the operating microscope to the surrounding brain parenchyma, and diffusely infiltrative behavior of high-grade gliomas make complete tumor resection difficult to achieve. This has led to the evaluation of various imaging modalities to aid in the visualization of invasive margins for maximal safe resection. Intraoperative fluorescence-guided resection has emerged as a particularly attractive option. The most widely used fluorescent agents for image-guided surgery include the prodrug 5-aminolevulinic acid (5-ALA), which is metabolized in cells to the fluorescent compound protoporphyrin IX (PpIX), fluorescein, and indocyanine green (ICG).

A randomized multi-center phase III clinical trial with 5-ALA found that fluorescence-guidance can lead to significant improvement in the extent of brain tumor resection and progression free survival; however, it did not lead to a significant increase in overall survival. Similar findings have been reported for fluorescein. It has been suggested that lack of improvement in overall survival may stem from inadequate sensitivity, due to visually imperceptible concentrations of PpIX or vague fluorescence due to photobleaching, poor specificity, due to the absence of PpIX at some tumor margins or the presence of PpIX at sites where there is no histological evidence of tumor cells, and subjective interpretation at tumor margins. Lack of specificity, but not sensitivity, was also a limiting factor with ICG. ICG had a sensitivity of 98% and an imaging depth of 13 mm (compared to 3 mm for 5-ALA), but the specificity was only 45% in gadolinium (Gd)-enhancing specimens. The low specificity was partially attributed to the highly diffusive nature of ICG during surgery.

Overall, these results suggest that fluorescence-guidance can improve resection, but many challenges must still be overcome to improve survival. In particular, an agent is yet to be identified that exhibits both high sensitivity and high specificity. Low-molecular weight contrast agents, such as ALA/PpIX and ICG readily diffuse into and out of the interstitium and do not remain in the same distribution over the hours required for tumor resection. Several studies in pre-clinical models of glioblastoma have suggested that nanoparticles may offer a promising solution. For example, fluorescently labeled (Cy5.5) superparamagnetic iron oxide nanoparticles (SPIONs) can provide accurate demarcation of the tumor margin, with a mean over-estimation of 24 µm in a GBM rat model, following intravenous administration. The maximum over-estimation was 151 µm and the maximum underestimation was only 57 µm, i.e. within one cell diameter of the true boundary. Moreover, the nanoparticles are usually trapped within the extracellular matrix or are internalized by cells before surgery commences. Therefore, they do not diffuse out of cells or through the interstitial space during surgery. Despite the promise of this approach, these nanoparticles exhibit reduced fluorescence due to SPION-mediated quenching, required crosslinking and amination of the dextran-coated SPION using techniques that are challenging to adapt for scaled up production and clinical translation, and utilized materials that are not yet FDA approved.

In many instances, not only the inability to visualize the tumor margin prevents total resection, but anatomic and technical factors also do so. For example, diminished extent of resection has been associated with eloquent, periventricular, or dominant hemisphere location. In a retrospective review of a surgical series, one third of GBMs with subtotal resection were initially thought to be amenable to gross total resection by imaging criteria. This has led to an interest in photodynamic therapy (PDT) as a secondary measure to eliminate residual tumor tissue that cannot be safely removed by resection or that is unintentionally missed. PDT involves the use of a photosensitizer, that when excited by light irradiation, produces reactive oxygen species that are cytotoxic to cells.

Photodynamic therapy (PDT) is a minimally-invasive procedure for the treatment of cancers. PDT uses light irradiation in combination with chemical photosensitizers (PS) to eradicate target tumor tissues. In the absence of light, PS are nontoxic to cells, but when illuminated with specific activating wavelengths, the photosensitizers generate cytotoxic reactive oxygen species (ROS) that destroy cells. The power density of PDT is very low and can kill cancer cells in a controlled manner Compared with ionizing radiation therapy or chemotherapy, PDT can be safer for the surrounding normal tissues or organs because the generation of ROS is a light-triggered process, thus limiting the area of exposure, and photosensitizers can preferentially accumulate in tumor cells, further improving the specificity of therapy. PDT has several advantages over more conventional cancer therapies, including cost-effectiveness, highly localized and specific tumor treatments, outpatient therapy, and higher cure rates for some tumors.

There have been numerous clinical trials on the use of PDT to treat malignant brain tumors, using a range of different photosensitizers (e.g., 5-ALA/PpIX, photofrin, talaporfin, hematoporphin derivative, and temoporfrin). The vast majority of these have been uncontrolled Phase I/II studies, making it difficult to draw any definitive conclusions. However, in a multicenter Phase III trial, fluorescence-guided resection and PDT with 5-ALA and photofrin led to a statistically significant increase in overall survival (12.2 mo vs. 5.6 mo) and progression free survival (8.6 mo vs. 4.8 mo). Survival in the control group was lower than what is typically seen with current standard of care, but this was attributed to a much greater proportion of poor prognostic factors in the study population. In a more recent study in Japan, it was found that GBM patients that underwent PDT with talaporfin (i.e. mono-L-aspartyl chlorin e6) had an overall survival of 24.8 months and only mild adverse events.

There is evidence that PDT can also be used to treat malignancies that are in proximity to vital structures. For example, in a pre-clinical canine model for infratentorial glioma, Photofrin-II resulted in significant tumor cell death with only mild neurotoxicity, according to Common Terminology Criteria for Adverse Events (CTCAE). Moreover, in two human trials, only one of eight patients with infratentorial glioma exhibited an adverse response to PDT.

While there is early evidence that PDT can improve outcome in patients with GBM, there is significant room for improvement.

The efficacy of PDT depends on the photosensitizing agent, its concentration, as well as the cell type. PS dosage is severely limited by the poor water solubility of most PS agents. Moreover, many of the clinically-used PS molecules are excited by visible light with limited tissue penetration and display side effects such as prolonged skin photosensitivity. The use of long-wavelength laser irradiation (650-900 nm) significantly improves the depth penetration for in vivo PDT.

Chlorin e6 (Ce6) is a second generation and clinically-used photosensitizer that is characterized by high sensitizing efficacy and rapid elimination from the body. Ce6 can be excited with a 660-670 nm laser that can penetrate deeper into human tissue than the 630-nm laser used for conventional or first generation photosensitizers such as Photofrin. For example, 665 nm light penetrates 22% deeper than 633 nm light in the human prostate gland. When irradiated, Ce6 has a high singlet oxygen ($^1O_2$) quantum yield and shows low dark toxicity, which makes Ce6 a favorable PS for PDT. Promising clinical benefits have been obtained with Ce6-mediated PDT (Ce6-PDT) for the treatment of lung, bladder, skin and head and neck cancers. Moreover, Ce6 exhibits improved therapeutic efficacy and reduced side effects compared to conventional photosensitizers that stem from hematoporphyrin derivatives. However, the clinical use of Ce6 has primarily been limited by its poor water solubility. Furthermore, sharp Soret and Q bands are observed for Ce6 in protic solvents except for water. To improve the poor water solubility of Ce6 for PDT, various kinds of nano-sized drug carriers such as nano-graphene and gold vesicles, or PS-conjugates with polyvinylpyrrolidone (PVP), human serum albumin, polymeric micelles, silica, peptides, glucamine (BLC 1010), and Ce6-conjugates with superparamagnetic iron oxide nanoparticles (SPIONs) by multistep chemical reactions have been developed. Unfortunately, Ce6's characteristic PDT properties are often suppressed when incorporated into a nanocarrier. Moreover, scaling up the synthesis and achieving a reproducible manufacturing process can be a major challenge. Therefore, there is still a need to develop new Ce6 formulations that are stable, scalable, reproducible and capable of delivering Ce6 to tumors in an efficient manner, without compromising its PDT properties.

Current neuro-navigation techniques allow neurosurgeons to make judgments between preoperatively acquired MRI scans and areas felt to represent tumor in the operating room. However, even if the co-registration of the surface anatomy of the skin is precise, the brain can shift during surgery. Because of this situation, many centers have used an intraoperative MRI scanner within the operating room environment, but the timing, dose, and type of intraoperative contrast agent used may affect which areas of the tumor (or brain) are ultimately resected. Intraoperative MRI also remains an expensive technology in terms of cost and time. These shortcomings have been partly responsible for the interest in systemically delivered fluorescent compounds that closely correlate with Gd-enhanced pre-operative scans. Unfortunately, it has been shown that current contrast agents like ICG do not exhibit a high specificity (45%) for gadolinium-enhancing specimens.

Based on these shortcomings, there is a need for highly sensitive and highly specific multi-modality nanoparticles, whereby the optical dye(s) used for image-guided surgery and/or PDT are stably associated with an MRI-detectable agent, so that the preoperative contrast-enhanced radiologic findings can be directly related with the visual presentation of PA-enhanced pathology during surgery. Accordingly, there exists a need to develop improved nanoparticles for biomedical imaging and treatment.

SUMMARY OF THE INVENTION

In one aspect, the invention relates to nanoclusters comprising: a plurality of inorganic nanoparticles, wherein said nanoparticles are coated by one or more amphiphilic dyes, and wherein said one or more amphiphilic dyes are capable of solubilizing said nanoparticles in an aqueous solvent. In an exemplary embodiment, an amphiphilic dye is a cyanine dye, a cyclic tetrapyrrole, or a combination thereof.

In another aspect, the invention provides nanoclusters comprising: a plurality of hydrophobic polymers, wherein said polymers are coated by one or more amphiphilic dyes, and wherein said one or more amphiphilic dyes are capable of solubilizing said polymers in an aqueous solvent. In an exemplary embodiment, an amphiphilic dye is a cyanine dye, a cyclic tetrapyrrole, or a combination thereof.

In another aspect, compositions (e.g., contrast agent composition) are provided, the compositions comprising: a nanocluster comprising a plurality of inorganic nanoparticles, wherein said nanoparticles are coated by one or more amphiphilic dyes, and wherein said one or more amphiphilic dyes are capable of solubilizing said nanoparticles in an aqueous solvent.

In another aspect, compositions (e.g., contrast agent composition) are provided, the compositions comprising: a nanocluster comprising a plurality of hydrophobic polymers, wherein said polymers are coated by one or more amphiphilic dyes, and wherein said one or more amphiphilic dyes are capable of solubilizing said polymers in an aqueous solvent.

In another aspect, methods are provided for identifying a tissue (e.g., a tumor tissue) to treat a disease (e.g., cancer) in a subject, the method comprising: administering to said subject a nanocluster described herein; detecting said nanocluster by an imaging modality; and based on the detection, identifying said tissue associated with said disease in said subject. In an exemplary embodiment, the imaging modality is x-ray imaging, computed tomography (CT), magnetic resonance imaging (MRI), photoacoustic imaging, fluorescence imaging, or fluoroscopy.

In another aspect, methods are provided for treating a cancer in a subject, the method comprising: administering to said subject a nanocluster described herein; detecting said nanocluster by an imaging modality; based on the detection, identifying a tumor associated with said cancer; and treating said cancer.

In another aspect, methods are provided for performing an image-guided surgery in a subject, the method comprising: administering to said subject a nanocluster described herein; detecting said nanocluster by an imaging modality; and based on the detection, identifying a tissue that needs to be surgically removed; and performing a surgery in said subject, and thereby performing said image-guided surgery in said subject.

In another aspect, methods are provided for enhancing the effect of a radiation therapy in a subject, the method comprising: administering to said subject a nanocluster described herein; detecting said nanocluster by an imaging modality; based on the detection, identifying a target site; and treating said subject with a radiation at said identified targeted site, wherein the nanocluster increases the amount of radiation absorbed at said targeted site.

In another aspect, methods are provided for ablating tissue by phototherapy in a subject, the method comprising: administering to said subject a nanocluster described herein; detecting said nanocluster by an imaging modality; based on the detection, identifying a target site; and and treating said subject with electromagnetic radiation at said targeted site, wherein the nanocluster absorbs the electromagnetic radiation and converts the electromagnetic radiation to heat, reactive oxygen species, or a combination thereof, to ablate the tissue at said targeted site.

In one aspect, the invention discloses a nanocluster comprising a plurality of inorganic nanoparticles, wherein the nanoparticles are coated by an amphiphilic dye, and wherein amphiphilic dye solubilizes the nanoparticles in an aqueous solvent or aqueous environment, and wherein the amphiphilic dye is a photosensitizer.

In another aspect, the invention discloses a nanocluster comprising a plurality of hydrophobic polymers, wherein said polymers are coated by an amphiphilic dye, and wherein amphiphilic dye solubilizes the polymers in an aqueous solvent or aqueous environment, and wherein the amphiphilic dye is a photosensitizer.

In one aspect, the invention discloses a theranostic agent comprising a nanocluster, the nanocluster comprising a plurality of inorganic nanoparticles, wherein the nanoparticles are coated by an amphiphilic dye, and wherein amphiphilic dye solubilizes the nanoparticles in an aqueous solvent or aqueous environment, and wherein the amphiphilic dye is a photosensitizer.

In another aspect, the invention discloses a theranostic agent comprising a nanocluster, the nanocluster comprising a plurality of hydrophobic polymers, wherein the polymers are coated by an amphiphilic dye, and wherein amphiphilic dye solubilizes the polymers in an aqueous solvent or aqueous environment, and wherein the amphiphilic dye is a photosensitizer.

In a further aspect, the invention discloses a pharmaceutical composition comprising the theranostic agent according to the invention.

In another aspect, the invention discloses a method for making a photosensitizer coated-nanocluster solubilized in an aqueous medium, the method comprising:
(a) combining (i) a plurality of inorganic nanoparticles or hydrophobic polymers, wherein the inorganic nanoparticles or polymers are in a first solvent, and (ii) an amphiphilic dye, wherein the amphiphilic dye is in a second solvent, and wherein the amphiphilic dye is a photosensitizer, to form a mixture; and
(b) sonicating the mixture of step (a) to form a homogeneous solution;
wherein the amphiphilic dye solubilizes the nanoparticles in an aqueous solvent or aqueous environment, thereby coating the nanoparticles with the photosensitizer.

In yet another aspect, the invention discloses a theranostic method for diagnosing a tumor in a subject and treating the tumor, the method comprising:
(a) administering to the subject the theranostic agent according to the invention;
(b) detecting the theranostic agent by an imaging modality;
(c) identifying the tumor in the subject based on detection step (b); and
(d) light irradiating the identified tumor at a specific wavelength, wherein upon the light irradiation, the photosensitizer generates cytotoxic reactive oxygen species, thereby treating the tumor.

In a further aspect, the invention provides an azide-functionalized nanocluster comprising the nanocluster according to the invention, wherein the amphiphilic dye is bioconjugated to an azide.

In another aspect, the invention provides a method for preparing a targeting antibody conjugated nanocluster, the method comprising:
reacting by copper-free click chemistry (i) an azide-functionalized nanocluster comprising the nanocluster of claim 28, wherein the amphiphilic dye is bioconjugated to an azide, and the nanocluster is carrier-free; and (ii) a targeting antibody functionalized with a dibenzocyclooctyne (DBCO) group, wherein the DBCO group labels the azide, thereby conjugating the antibody to the nanocluster.

In a still further aspect, the invention provides a method for treating a subject having a tumor, the method comprising:
(a) administering the targeting antibody conjugated nanocluster according to the invention to the subject, thereby increasing accumulation of the targteing antibody at the tumor;
(b) detecting the accumulation of the targteing antibody by an imaging modality;
(c) identifying the tumor in the subject based on detection step (b); and
(d) light irradiating the identified tumor at a specific wavelength, wherein upon the light irradiation, the photosensitizer generates cytotoxic reactive oxygen species, thereby treating the tumor.

In another aspect, the invention provides a method for producing a stable polymer-solubilized amphiphilic dye nanocluster, the method comprising:
(a) dissolving the amphiphilic dye in DMSO, wherein the amphiphilic dye is a photosensitizer, to prepare a photosensitizer solution;
(b) dissolving the polymers in toluene to prepare a polymer solution;
(c) combining the photosensitizer solution and the polymer solution into membrane-filtered water to prepare a mixture;
(d) sonicating the mixture of step (c) to form an emulsion;
(e) evaporating the toluene to form a toluene-free mixture;
(f) purifying the toluene-free mixture by dialysis to remove free amphiphilic dye and DMSO, thereby preparing the stable polymer-solubilized amphiphilic dye nanocluster.

Other features and advantages of the present invention will become apparent from the following detailed description examples and figures. It should be understood, however, that the detailed description and the specific examples while indicating embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

(FIG. 1A) Schematic representation of ICG-coated SPIO clusters (ISCs). Iron oxide nanoparticles are self-assembled using a microemulsion technique and stabilized using indocyanine green (ICG), an amphiphilic, cyanine dye. (FIG. 1B) Dynamic light scattering (DLS) profile of ISCs. Size distribution by intensity percentage, in water. Transmission electron microscopy (TEM; inset) performed demonstrate spherical, tightly packed clusters with SPIO-NP cores (scale bar: 100 nm). (FIG. 1C) Particle size based on mean intensity (%) measurements (DLS) taken over a total of 8 days, in water at 25° C. (FIG. 1D) Magnetic resonance (MR) relaxometry measurements of ISCs. MR phantom image (inset) of ISCs at various concentrations in a microplate. (FIG. 1E) Photoacoustic phantom of ISCs, demonstrating increased PA intensity with concentration. Testing performed in 0.5 mm diameter polyethylene tubing submerged in milk, depth between 1-2 cm. PA averages (Average PA intensity (arbitrary units, AU) are computed using photoacoustic intensity per unit volume at 850 nm excitation.

(FIG. 2A) Transmission electron microscopy (TEM) of superparamagnetic iron oxide (SPIO) nanoparticles following thermal decomposition reaction. Scale bar=20 nm. (FIG. 2B) Analysis of TEM results demonstrating the size distribution of SPIO.

(FIG. 6A) ISCs were incubated in serum, at 37° C., and dynamic light scattering (DLS) and relaxometry measurements were recorded as a function of time. (FIG. 6B) Release of ICG from ISCs was monitored as a function of time following addition to serum, at 37° C. (FIG. 6C) Proliferation of human embryonic kidney (HEK) 293T cells (black bar), human umbilical vein endothelial cells (HUVEC) (white bar), and U251 glioblastoma cells (gray bar) was assessed via an MTT assay, after incubation with increasing concentrations of ISCs for 24 hrs.

(FIG. 9A) T2-weighted magnetic resonance (MR) imaging before (left) and 24 hours after (right) intravenous (intraorbital) injection of 1 mg/kg ISCs by ICG weight into mice bearing U251 flank xenografts. Yellow circles denote the location of the flank tumor. (FIG. 9B) Signal-to-background ratio (SBR) measurements were made using the candidate tumor and the paraspinous musculature (green asterisk) as background. Pre-injection versus post-injection SBR measurements are shown. (FIG. 9C) Ultrasound and Photoacoustic imaging before (left) and 24 hours after (right) intravenous (intraorbital) injection of 1 mg/kg ISCs by ICG weight into a mouse bearing U251 flank xenograft tumor. ISCs were noted at a red-shifted wavelength (850 nm) relative to the fluorescence spectra of ICG.

FIGS. 11A-11B. (FIG. 11A) Animals were injected with 1 mg/kg ISCs and imaged 24 hours following injection. Left panels show ultrasound imaging as seen using the Photoacoustic imaging platform. Right panels show photoacoustic imaging (PA) data obtained following injection. Pre-operative PA imaging with excitation at 850 nm demonstrates signal within the tumor (top). Following surgical debulking, persistent PA signal is notable at the resection cavity (middle). Following complete excision, saline irrigation, and skin closure, low residual PA signal is noted (bottom). (FIG. 11B) Surgical resection trial. Twenty-four mice (N=24) were implanted with U251 cells expressing luciferase (U251+Luc) and randomized to either a PA-guided surgery arm (N=12, solid line) or microscopic surgical resection arm (N=12, dashed line). Following surgery, all animals were identified/tagged and monitored for recurrence at varying time points to assess for survival and progression of disease.

FIG. 12. Representative fluorescent images of mice injected with free ICG (left) or ICG SPIO clusters (ISCs), dosed 1 mg/kg based on ICG weight. Fluorescent images were acquired 24 hours following intraorbital injection. Instrumentation/parameters: Perkin Elmer IVIS Spectrum In Vivo Imaging System (excitation 745 nm, emission 800 nm, lamp level=low, exposure times: 10 s, binning 4, f=1).

FIGS. 15A-15D. (FIG. 15A) Schematic of PpIX-coated SPION nanoclusters (NC). The hydrophobic portion of PpIX interacts with the SPIONs (pink), while the hydrophilic domains are exposed to the surrounding aqueous environment (white). (FIG. 15B) DLS of PpIX-coated SPION nanoclusters. Inset: TEM image of PpIX-coated SPIONs, with core composed of tightly packed clusters of 7 nm SPIONs (FIG. 15C) Stability of PpIX-coated SPION nanoclusters in serum. The magnetic properties (i.e. T2 relaxation time) and the hydrodynamic diameter of nanoclusters were measured in serum as a function of time. No signs of aggregation or precipitation were observed. (FIG. 15D) Tumor growth in mice (n=4 or 5 per group) treated with various PpIX formulations, with and without PDT. PpIX-coated SPION nanoclusters led to a significant delay in tumor growth compared with all other groups, despite an 8-fold lower injection dose of PpIX.

(FIG. 16A) Cell culture media, free ICG (40 μg/mL), and ICG-coated SPION nanoclusters (NCs; 40 μg ICG/mL) were subjected to PTT (808 nm, 2 W/cm$^2$). The ICG-coated SPION nanoclusters led to more rapid and higher total heating of media, compared with free ICG. (FIG. 16B) U251 GBM cells were incubated with various concentrations of free ICG or ICG-coated SPION nanoclusters and then subjected to PTT (2 W/cm$^2$, 5 min). ICG-coated SPION nanoclusters were found to be more potent PTT agents than free ICG.

(FIG. 17A) DLS and TEM (inset) of ICG- and PpIX-coated SPION Nanoclusters. (FIG. 17B) UV-VIS absorbance spectrum of ICG- and PpIX-coated SPION Nanoclusters. (FIG. 17C) DLS and TEM (inset) of ICG- and Chlorin e6-coated SPION Nanoclusters. (FIG. 17D) UV-VIS absorbance spectrum of ICG- and Chlorin e6-coated-coated SPION Nanoclusters.

FIGS. 22A-22D. (FIG. 22A) Illustration of Ce6-coated SPION nanoclusters (Ce6-SCs). Iron oxide nanoparticles are stabilized in aqueous media by the self-assembly of amphiphilic PS Chlorin e6 on the surface using a microemulsion. (FIG. 22B) Dynamic light scattering (DLS) of Ce6-SCs in water. Inset: TEM image of Ce6-SCs shows tightly packed nanoclusters (scale bar: 50 nm). (FIG. 22C) Particle size and T2 relaxation time was monitored for 6 days in water at 25° C. (FIG. 22D) Magnetic resonance (MR) relaxometry measurements of Ce6-SCs. Inset: $T_2$-weighted image of Ce6-SCs at various concentrations in a microplate. (FIG. 22E) Absorbance spectra of Ce6-SCs (black) and free Ce6 (brown) in water. The inset images are vials containing solutions of Ce6-SCs and free Ce6 in water.

(FIG. 23A) Transmission electron microscopy (TEM) of superparamagnetic iron oxide nanoparticles (SPIONs) following thermal decomposition reaction. Scale bar=20 nm. (FIG. 23B) Analysis of TEM results demonstrating the size distribution of SPIO (diameter=7.6±1.0 nm).

(FIG. 24B) Ce6-SCs in serum (37° C.) were purified by magnetic separation at various time points to quantify the rate of Ce6 release/dissociation. (FIG. 24C) Viability of HUVEC cells (black bar) and 4T1 cells (gray bar) after incubation with increasing concentrations of Ce6-SCs for 24 h. (FIG. 24D) Viability of 4T1 cells treated with different concentrations of Ce6-SCs, with and without laser irradiation (665 nm, 5 J/cm$^2$).

FIGS. 26A-26D (FIG. 26A) In vivo MR images of mice bearing 4T1 flank tumors pre- and 24 h post-intravenous injection (i.v.) of Ce6-SCs Images were acquired using 4.7 T MRI. Yellow circles denote the location of the flank tumor. Localization of Ce6-SCs in the tumor results in decreased intensity in the post-injection MR images. (FIG. 26B) Signal-to-background ratio (SBR) measurements were made using the candidate tumor and the paraspinous musculature (green star) as background. Quantification of the pre-injection versus post-injection SBR measurements is shown. (FIG. 26C) Representative fluorescent images of mice injected with Ce6-SCs (left) and free Ce6 (right), dosed at 2.5 mg/kg based on Ce6 weight. Fluorescent images were acquired 24 hours following i.v. injection. (FIG. 26D) Signal-to-background ratio of mice injected with Ce6-SCs and free Ce6 at 640 nm excitation and 720 nm emission.

(FIG. 27D) The relative absorbance changes of ABDA at 380 nm versus light irradiation time.

FIGS. 28A-28B (FIG. 28A) Average tumor volume is plotted relative to the number of days after treatment. Tumor volume was measured daily. The error bars represent the standard deviations of 5 mice per group. *, $p<0.001$ and **, $p<0.76$. (FIG. 28B) The body weight of 4T1 tumor-bearing mice was monitored after treatment.

FIGS. 29A-29E The same experiment (as mentioned in FIG. 27A-27D) was applied to free PpIX (FIG. 29A), PpIX-SCs in DMSO (FIG. 29B) and PpIX-SCs in water (FIG. 29C), PpIX micelle in water (FIG. 29D). The solutions were irradiated under a laser ($\lambda$=632 nm, power density=5 mW/cm$^2$). (FIG. 29E) The relative absorbance changes of ABDA at 380 nm versus light irradiation time.

(FIG. 31C) Comparison of 4T1 cell viability when treated with Ce6-SCs+665 nm irradiation or PpIX-SCs+632 nm irradiation (* P<0001 and ** P<0.001). All studies were performed using a power density=5 mW/cm$^2$.

FIG. 32A is a schematic of a targeted nanocluster with a therapeutic/imaging reagents shell (i.e., ICG-N$_3$/ICG or PpIX-N$_3$/PpIX, Blue/Green) containing targeting ligands and hydrophobic SPIONs core. FIG. 32B shows dynamic light scattering (DLS) of ISCs-HER2 in water. FIG. 32B insert is a TEM image of ISCs-HER2 shows tightly packed nanoclusters (scale bar: 50 nm). FIG. 32C illustrates monitoring of particle size and T2 relaxation time for 6 days in water at 25° C. FIG. 32D shows Magnetic resonance (MR) relaxometry measurements of ISCs-HER2.

(FIG. 34A) Dynamic light scattering (DLS) of PSCs-HER2 in water. Inset: TEM image of PSCs-HER2 shows tightly packed nanoclusters (scale bar: 50 nm). (FIG. 34B) Particle size and T2 relaxation time was monitored for 6 days in water at 25° C. (FIG. 34C) Magnetic resonance (MR) relaxometry measurements of PSCs-HER2.

DETAILED DESCRIPTION OF THE INVENTION

Figure 1A:
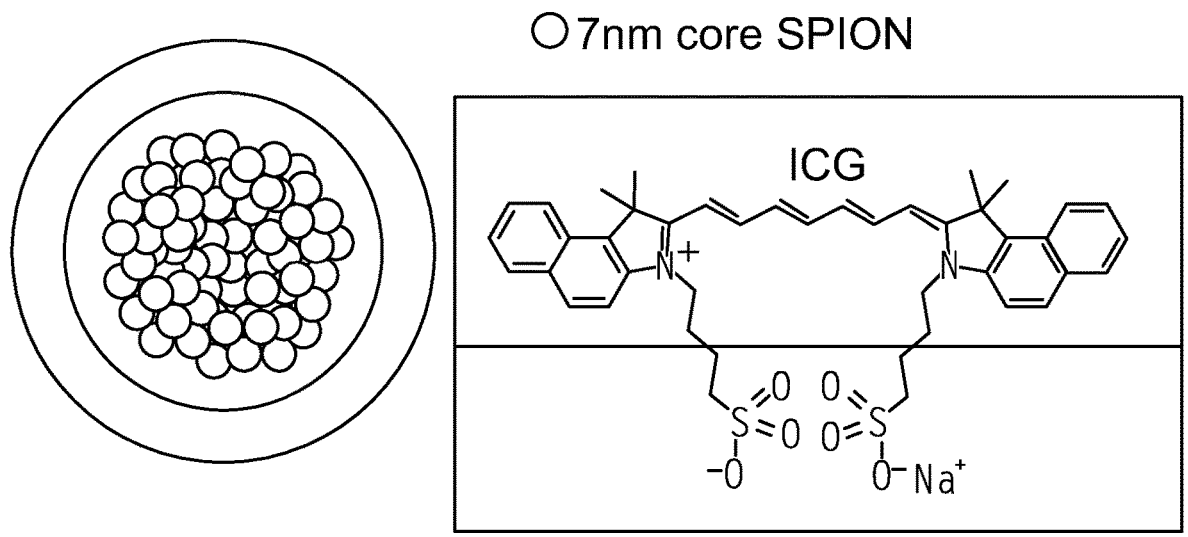
FIGS. 1A-1E.

The subject matter here may be understood more readily by reference to the following detailed description which forms a part of this disclosure. It is to be understood that the invention is not limited to the specific products, methods, conditions, or parameters described and/or shown here, and that the terminology used here is for the purpose of describing particular embodiments by way of example only and is not intended to limit the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality," as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

In one aspect, the invention provides nanoclusters comprising a plurality of inorganic nanoparticles and one or more amphiphilic dyes. In a particular aspect, the invention provides a nanocluster comprising a plurality of inorganic nanoparticles, wherein said nanoparticles are coated by one or more amphiphilic dyes, and wherein said one or more amphiphilic dyes are capable of solubilizing said nanoparticles in an aqueous solvent.

The term "nanocluster," as used herein, refers to a nanoscale grouping of inorganic nanoparticles that have been solubilized through the addition of one or more amphiphilic dyes.

In one embodiment, the nanocluster size may range from about 10 nm to about 750 nm. In some embodiments, the nanocluster size is less than about 200 nm, less than about 100 nm, less than about 50 nm, or less than about 30 nm. Smaller nanoclusters may also be used.

The term "nanoparticle," as used herein, refers to a nanostructure, a particle, a vesicle, or a fragment thereof having at least one dimension (e.g., height, length, width, or diameter) of between about 1 nm and about 10 μm.

In one embodiment, the nanoparticle size may range from about 1 nm to about 500 nm. In some embodiments, the nanoparticle size is less than about 500 nm, less than about 250 nm, less than about 100 nm, less than about 50 nm, less than about 25 nm, less than about 15 nm, less than about 10 nm, less than about 5 nm, less than about 4 nm, less than about 3 nm, less than about 2 nm, or less than about 1 nm Smaller nanoparticles may also be used.

The nanoparticles may have an approximately spherical shape, a rod shape, a disc shape, or another suitable morphology.

In one example, the nanoparticle of the invention is an inorganic nanoscale particle. Examples of an inorganic nanoparticle include, but are not limited to, a metal particle (e.g., gold, tantalum, lanthanum, ytterbium, bismuth, platinum, silver, etc.), an alloy of metals (e.g. gold and silver, gold and copper, copper and silver and others), a combination of metals (e.g. part one metal and part another metal, such as gold-silver core-shell structures), a magnetic nanoparticle (e.g. superparamagnetic iron oxide), a nanophosphor (e.g., gadolinium fluoride, lanthanum nanosphere), a quantum dot (e.g., cadmium selenide or zinc sulfide), and a combined metal-compound nanoparticle such as a silica core coated with gold and other structures, known to one of skilled in the art. In one embodiment, the nanoparticle is superparamagnetic iron oxide.

In one example, the nanocluster of the invention may include only one type of inorganic nanoparticle (e.g., superparamagnetic iron oxide). In another example, the nanocluster of the invention may include at least two different types of inorganic nanoparticles. For example, the nanocluster may comprise a plurality of superparamagnetic iron oxide nanoparticles and a plurality of gold nanoparticles.

According to one embodiment, the nanoparticle comprises a combination of two or more metals. For example, the nanoparticle may comprise a core-shell particle comprising a core of one metal coated with a shell of a second metal. The shell may be continuous or discontinuous. For example, the nanoparticle may comprise a silver core coated with a gold shell. The gold shell may completely cover the silver core, or the gold shell may have openings through which the underlying silver core is exposed.

The nanoparticle may comprise a diagnostically active material. As used herein, the term "diagnostically active material," refers to material that may be detected by a diagnostic instrument, such as, for example, a CT imaging system or an MRI scanner. The nanoparticle may be a contrast agent or an imaging agent.

In one embodiment, the nanoparticle comprises a compound suitable for use as an imaging agent or contrast agent. In one example, the nanoparticle comprises a compound suitable for use as an MRI imaging agent, such as, for example, iron oxide. The iron oxide may be doped or undoped. For example, the iron oxide may be doped with manganese, cobalt, nickel, or bismuth. The dopant may be selected, for example, to increase or decrease contrast of the image.

In another example, the nanoparticle comprises a compound suitable for use as a contrast agent in an X-ray based diagnostic technique (e.g., CT imaging or fluoroscopy), such as, for example, iodine, gold, silver, bismuth, yttrium, ytterbium, tantalum, tungsten, or platinum, as well as alloys, combinations, and salts thereof. In one embodiment, the nanoparticle is a gold nanoparticle.

In another aspect, the nanocluster may also comprise a drug. In one embodiment, the nanocluster may comprise inorganic nanoparticles and a drug, that have been solubilized through the addition of one or more amphiphilic dyes (e.g., cyanine and/or cyclic tetrapyrrole dyes). As used herein, the term "drug," broadly describes a molecule that has a biological effect on humans or other animals. For example, a drug may be a small molecule compound or a large molecule biopharmaceutical (i.e., biologics), for example, peptides, antibodies, proteins, and nucleic acids.

In one aspect, the nanoparticles are hydrophobic. In another aspect, the nanoparticles are dissolved in an organic solvent.

In another aspect, the nanoparticles are coated with a carbon-based ligand. Examples of a carbon-based ligand include, but are not limited to, oleic acid, oleylamine, dodecanethiol, and other carbon-based ligands known in the art.

As described above, the nanoclusters may comprise a plurality of inorganic nanoparticles and one or more amphiphilic dyes. In one embodiment, the nanoparticles are fully or partially coated by one or more amphiphilic dyes. The amphiphilic dye solubilizes the nanoparticles in an aqueous solvent, forming a stable nanocluster.

In one embodiment, the amphiphilic dye is a cyanine dye, a cyclic tetrapyrrole, or another suitable amphiphilic dye known to one of skilled in the art.

Cyanine dyes may be selected from a molecule containing a polymethine bridge between two nitrogen atoms with a delocalized charge. Examples of a cyanine dye include, but are not limited to, indocyanine green (ICG), cypate, Cy3, Cy3.5, Cy5, Cy5.5, Cy7, Cy7.5, LS-276, IR-820, LS-277, LS-288, CTTCI, IR-806, and variants thereof.

Examples of a cyclic tetrapyrrole dye include, but are not limited to, porphin, porphyrin, chlorin, corrin, and a variant thereof. Specific examples include, but are not limited to, PpIX and Chlorin e6.

The nanoclusters can be made, for example, via an oil-in-water emulsion method, known to one of skilled in the art. In one embodiment, the nanoparticles and the cyanine dyes are dissolved in an organic solvent, prior to formation of an oil-in-water emulsion. As used herein, the term "organic solvent" refers to a carbon-based solvent, for example, toluene, DMF, DMSO, dichloromethane, hexane, chloroform, THF, ethanol, methanol, and other solvents known in the art.

According to another aspect, the nanoclusters may be operably linked to one or more targeting agents (also known as "targeting ligands"). The targeting agent may be a molecule or a structure that provides targeting of the nanocluster to a desired organ, tissue or cell. Non-limiting examples of such targeting agents include peptides, antibodies, proteins, nucleic acids, small molecules, etc. The targeting agent(s) is preferably attached to the outer surface of the nanocluster for targeted imaging. A nanocluster composition comprising one or more targeting agents can be targeted to a specific diseased area of the subject's body.

The nanoclusters disclosed herein may be used in diagnostic imaging techniques, such as, for example, x-ray, CT imaging, mammography, dual energy (DE) mammography, tomosynthesis, MRI, fluorescence imaging, photoacoustic imaging, or other techniques using diagnostically active agents.

In another aspect, provided herein is a method for identifying a tissue (e.g., a tumor tissue) to treat a disease (e.g., cancer) in a subject, the method comprising: administering to said subject a nanocluster described herein; detecting said nanocluster by an imaging modality; and based on the detection, identifying said tissue associated with said disease in said subject. In another aspect, provided herein is a method for treating a disease (e.g., cancer) in a subject.

The nanoclusters disclosed herein may be used for image-guided surgery, using imaging modalities such as photoacoustic imaging, MRI, fluorescence imaging, fluoroscopy, or other imaging techniques capable of guiding a surgeon.

In another aspect, provided herein is a method for performing an image-guided surgery in a subject, the method comprising: administering to said subject a nanocluster described herein; detecting said nanocluster by an imaging modality; and based on the detection, identifying a tissue that needs to be surgically removed; and performing a surgery in said subject, and thereby performing said image-guided surgery in said subject.

The nanoclusters disclosed herein may be used for presurgical imaging/planning and subsequently for image-guided surgery.

The nanoclusters disclosed herein may be used for photothermal therapy, photodynamic therapy, radiation therapy and combinations thereof. For example, the nanoclusters could be used in photothermal ablation or other ablation techniques where the nanoclusters would preferentially absorb electromagnetic radiation such as far red or near infra-red light and convert it to heat, thereby resulting in pathological tissue death. In another example, the nanoclusters could be used in photodynamic where the nanoclusters would preferentially absorb electromagnetic radiation such as far red or near infra-red light and convert it to reactive oxygen species, thereby resulting in pathological tissue death. Accordingly, in another aspect, the invention relates to a method for ablating a tissue by a phototherapy in a subject, the method comprising: administering to said subject a nanocluster described herein; detecting said nanocluster by an imaging modality; based on the detection, identifying a target site; and treating said subject with electromagnetic radiation at said targeted site, wherein the nanocluster absorbs the electromagnetic radiation and converts the electromagnetic radiation to heat, reactive oxygen species, or a combination thereof, to ablate the tissue at said targeted site.

In another aspect, the invention provides a nanocluster comprising: a plurality of hydrophobic polymers, wherein said polymers are coated by one or more amphiphilic dyes, and wherein said one or more amphiphilic dyes are capable of solubilizing said polymers in an aqueous solvent. In various embodiments, the polymer is a biodegradable polyester. In further embodiments, the biodegradable polyester is polylactic acid (PLA), polyglycolic acid (PGA), poly-ε-caprolactone (PCL), polyhydroxybutyrate (PHB), and poly (3-hydroxy valerate)polycaprolactone, poly(ethylene succinate) (PESu), poly(propylene succinate) (PPSu) and poly (butylene succinate) (PBSu). In an embodiment, at least one of the one or more amphiphilic dyes is a cyanine dye, a cyclic tetrapyrrole, or a combination thereof. In another embodiment, the cyanine dye is indocyanine green. In certain embodiments, the cyclic tetrapyrrole is photoporphyrin IX (PpIX) or Ce6. In additional embodiments, the size of the nanocluster ranges from about 10 nm to about 750 nm.

In other embodiments, the nanocluster further comprises at least one targeting agent on the surface of said nanocluster. In an embodiment of the nanocluster according to the invention, the nanocluster further comprises a drug on the surface of the nanocluster, within a core of the nanocluster, dispersed throughout the nanocluster, or a combination thereof. In another embodiment, the nanocluster are formed via an oil-in-water emulsion. In a further embodiment, the polymers and the amphiphilic dyes are dissolved in an organic phase. In an additional embodiment of the nanocluster according to the invention, at least one of the one or more amphiphilic dyes is a cyanine dye, a cyclic tetrapyrrole, or a combination thereof. In an embodiment, the cyanine dye is indocyanine green. In another embodiment, the cyclic tetrapyrrole is photoporphyrin IX (PpIX) or Ce6. In another embodiment, the size of the nanocluster ranges from about 10 nm to about 750 nm.

In an embodiment, the nanocluster further comprises at least one targeting agent on the surface of said nanocluster. In another embodiment, the nanocluster further comprises a drug on the surface of the nanocluster, within a core of said nanocluster, dispersed throughout said nanocluster, or a combination thereof. In a further embodiment, the nanoclusters are formed via an oil-in-water emulsion. In still another embodiment, the polymers and the amphiphilic dyes are dissolved in an organic phase.

In another aspect, the invention provides a method for making the nanocluster comprising: a plurality of hydrophobic polymers, wherein said polymers are coated by one or more amphiphilic dyes, and wherein said one or more amphiphilic dyes are capable of solubilizing said polymers in an aqueous solvent, the method comprising: forming the nanocluster according to the invention via an oil-in-water emulsion. In a embodiment of the method, the polymers and the amphiphilic dyes are dissolved in an organic phase. In another embodiment, the polymers and the amphiphilic dyes are dissolved in an organic phase.

In a further aspect, the invention provides a composition comprising: a nanocluster comprising a plurality of polymeric molecules, wherein said polymers are coated by one or more amphiphilic dyes, and wherein said one or more amphiphilic dyes are capable of solubilizing said polymers in an aqueous solvent. In an embodiment, the composition is a contrast agent composition. In another embodiment, the composition is a pharmaceutical composition.

In an aspect, the invention provides a method for identifying a tumor associated with a cancer to treat said cancer in a subject, the method comprising: administering to said subject the nanocluster comprising: a plurality of hydrophobic polymers, wherein said polymers are coated by one or more amphiphilic dyes, and wherein said one or more amphiphilic dyes are capable of solubilizing said polymers in an aqueous solvent; detecting said nanocluster by an imaging modality; and based on the detection, identifying said tumor associated with said cancer in said subject. In an embodiment, the imaging modality is x-ray imaging, computed tomography (CT), magnetic resonance imaging (MRI), photoacoustic imaging, fluorescence imaging, or fluoroscopy. In another embodiment, the cancer is glioblastoma multiforme, lung cancer, mesothelioma, breast cancer, ovarian cancer, prostate cancer, or head and neck cancer.

In another aspect, the invention provides a method for performing an image-guided surgery in a subject, the method comprising: administering to said subject the nanocluster comprising: a plurality of hydrophobic polymers, wherein said polymers are coated by one or more amphiphilic dyes, and wherein said one or more amphiphilic dyes are capable of solubilizing said polymers in an aqueous solvent; detecting said nanocluster by an imaging modality; and based on the detection, identifying a tissue that needs to be surgically removed; and performing said surgery in said subject, and thereby performing said image-guided surgery in said subject. In an embodiment, the imaging modality is x-ray imaging, computed tomography (CT), magnetic resonance imaging (MRI), photoacoustic imaging, fluorescence imaging, or fluoroscopy.

In a further aspect, the invention provides a method for ablating a tissue by a phototherapy in a subject, the method comprising: administering to said subject the nanocluster the nanocluster comprising: a plurality of hydrophobic polymers, wherein said polymers are coated by one or more amphiphilic dyes, and wherein said one or more amphiphilic dyes are capable of solubilizing said polymers in an aqueous solvent; detecting said nanocluster by an imaging modality; based on the detection, identifying a target site; and treating said subject with electromagnetic radiation at said targeted site, wherein the nanocluster absorbs the electromagnetic radiation and converts the electromagnetic radiation to heat, reactive oxygen species, or a combination thereof, to ablate the tissue at said targeted site.

The nanoclusters may also be used for photodynamic therapy, photothermal therapy and combinations thereof, of the surgical resection cavity.

The nanoclusters disclosed herein can be injected in a subject and then the subject scanned to ensure that the nanocluster is delivered to the desired location.

In another aspect of the present invention, the nanoclusters could be used as therapeutic adjuvants. For example, the nanoclusters could be used to enhance the effect of radiation therapy by increasing the radiation absorbed in a diseased site. Accordingly, in another aspect, provided herein is a method for enhancing the effect of radiation therapy in a subject, the method comprising: administering to said subject a nanocluster described herein; detecting said nanocluster by an imaging modality; based on the detection, identifying a target site; and treating said subject with a radiation at said identified targeted site, wherein the nanocluster increases the amount of radiation absorbed at said targeted site.

In another aspect, provided herein is a method for transfecting a cell with a nanocluster, comprising contacting a cell with a nanocluster described herein, where the nanocluster may comprise a targeting agent. In one embodiment, the method comprises contacting the cell with the nanocluster in the presence of an applied magnetic field.

The term "subject," as used herein, refers to any suitable mammal, including primates, such as monkeys and humans, horses, cows, cats, dogs, rabbits, and rodents such as rats and mice. In one embodiment, the subject is a human.

As used herein, the terms "component," "composition," "composition of compounds," "compound," "drug," "pharmacologically active agent," "active agent," "therapeutic," "therapeutic agent," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder.

The term "theranostic agent" as used herein refers to a single agent comprising both a diagnostic agent and a therapeutic agent. In specific embodiments, the theranostic agent is nanoparticle-based. The terms "diagnostic agent" and "diagnostically active material" are used interchangeably herein. In an embodiment, the theranostic agent comprises a nanocluster, the nanocluster comprising nanoparticles, the nanoparticles comprising a diagnostically active material, as defined herein, and a therapeutic agent, as defined herein. In certain embodiments, the nanop article may be a contrast agent or an imaging agent. In some embodiments, the therapeutic agent comprises an agent used to effect PDT. In some embodiments, the agent used to effect PDT is a photosensitizer. In certain embodiments, the therapeutic agent comprises an antibody. In some embodiments, the antibody comprises an anti-HER2 antibody (also referred to herein as "anti-Her2 targeting" antibody). In additional embodiments, the therapeutic agent comprises anti-Her2 targeting affibodies. In some embodiments, the therapeutic agent comprises a therapeutic adjuvant. In certain embodiments, the therapeutic agent comprises a therapeutic agent and an imaging agent (also referred to herein as a "therapeutic/imaging" agent or reagent. In further embodiments, the theranostic agent is a dual-made agent for imaging and photodynamic therapy. In particular embodiments, the photosensitizer is chlorin e5 (Ce6). In some embodiments, the Ce6 is adsorbed on the nanocluster.

In particular embodiments, the theranostic agent comprises superparamagnetic iron oxide nanoparticle (SPION) nanoclusters, wherein the SPION nanoclusters are coated with a photosensitizer, wherein the photosensitizer is capable of solubilizing the SPION nanoclusters in an aqueous solvent to form a stable nanocluster, without addition of any extra carrier and without complicated chemical reaction to produce the solubilized photosensitizer coated-SPION nanoclusters. In various embodiments, the photosensitizer solubilizes the SPION nanoclusters in an aqueous solvent to form a stable nanocluster, without addition of any extra carrier and without complicated chemical reaction to produce the solubilized photosensitizer coated-SPION nanoclusters. In specific embodiments the photosensitizer is Ce6; and such Ce6 coated-SPION nanoclusters are referred to herein as "Ce6-SCs". In an embodiment the Ce6 is adsorbed on the SPION nanoclusters. In some embodiments, the aqueous solvent is a mammalian body fluid. In various embodiments, the aqueous environment is a mammalian tissue or organ. In various embodiments, the aqueous environment is a tumor located in a mammalian body fluid, tissue or organ. In an embodiment, the mammalian body fluid includes but is not limited to blood, blood components, e.g., plasma, serum, cerebrospinal fluid, lymphatic fluid (lymph).

In one aspect, the invention discloses a nanocluster comprising a plurality of inorganic nanoparticles, wherein the nanoparticles are coated by an amphiphilic dye, and wherein amphiphilic dye solubilizes the nanoparticles in an aqueous solvent or aqueous environment, and wherein the amphiphilic dye is a photosensitizer.

In an embodiment, the adsorption of the photosensitizer on the nanoparticles solubilizes the nanoparticles. In another embodiment, the nanoparticles are superparamagnetic iron oxide nanoparticles (SPIONs).

In a further embodiment, the photosensitizer is a chlorin or a derivative thereof. In an additional embodiment, the chlorin is Ce6. In an embodiment, the chlorin derivative is amidochlorin p6 (ACP). In another embodiment, the chlorin derivative is single aspartyl Ce6 (N-aspartyl chlorin Npe6).

In certain embodiments, the chlorin derivative is pheophorbide a (2-deacetyl-2-vinylbacteriopheophorbide). In other embodiments, the chlorin is meso-tetra (3-morphlinomethyl-4-methoxyphenyl) chlorin (TMMC). In certain embodiments, the photosensitizer is a Ce6 derivative. The Ce6 derivative may be chlorin e6 ethylenediamide or a chlorin e6 and polyvinylpyrrolidone (Ce6-PVP) complex.

In another aspect, the invention discloses a theranostic agent comprising a nanocluster, the nanocluster comprising a plurality of inorganic nanoparticles, wherein the nanoparticles are coated by an amphiphilic dye, and wherein amphiphilic dye solubilizes the nanoparticles in an aqueous solvent or aqueous environment, and wherein the amphiphilic dye is a photosensitizer.

In an embodiment of the theranostic agent, the adsorption of the photosensitizer on the nanoparticles solubilizes the nanoparticles. In certain embodiments, the nanoparticles are superparamagnetic iron oxide nanoparticles (SPIONs). In other embodiments, the photosensitizer is a chlorin or a derivative thereof. In various embodiments, the chlorin is Ce6. In additional embodiments, the chlorin derivative is amidochlorin p6 (ACP). In further embodiments, the chlorin derivative is single aspartyl Ce6 (N-aspartyl chlorin Npe6). In another embodiment, the chlorin derivative may be pheophorbide a (2-deacetyl-2-vinylbacteriopheophorbide). In other embodiments, the chlorin may be meso-tetra (3-morphlinomethyl-4-methoxyphenyl) chlorin (TMMC). In a further embodiment, the photosensitizer may be a Ce6 derivative. In a still further embodiment, the Ce6 derivative may be chlorin e6 ethylenediamide or a chlorin e6 and polyvinylpyrrolidone (Ce6-PVP) complex.

In a further aspect, the invention discloses a pharmaceutical composition comprising the theranostic agent according to the invention.

In another aspect, the invention discloses a method for making a photosensitizer coated-nanocluster solubilized in an aqueous medium, the method comprising:
(a) combining (i) a plurality of inorganic nanoparticles, wherein the inorganic nanoparticles are in a first solvent, and (ii) an amphiphilic dye, wherein the amphiphilic dye is in a second solvent, and wherein the amphiphilic dye is a photosensitizer, to form a mixture; and
(b) sonicating the mixture of step (a) to form a homogeneous solution;
wherein the amphiphilic dye solubilizes the nanoparticles in an aqueous solvent or aqueous environment, thereby coating the nanoparticles with the photosensitizer.

In certain embodiments, the method further comprises: (c) evaporating the second solvent, (d) performing dialysis to remove the first solvent; and (e) purifying the photosensitizer coated-nanocluster. In an embodiment, the first solvent is an organosulfur compound and the second solvent is toluene or a substitute for toluene. In another embodiment, the organosulfur compound is dimethyl sulfoxide (DMSO) or a non-organosulfur compound substitute for DMSO. In additional embodiments, the non-organosulfur compound substitute for DMSO is dimethylformamide (DMF), gamma-butyrolactone (GBL), N-Methyl-2-pyrrolidone (NMP), or dimethylacetamide (DMAc). In a further embodiment, the substitute for toluene is methyl cyclohexane, n-propyl acetate, or methyl ethyl ketone.

In yet another aspect, the invention discloses a theranostic method for diagnosing a tumor in a subject and treating the tumor, the method comprising:
(a) administering to the subject the theranostic agent according to the invention;
(b) detecting the theranostic agent by an imaging modality;
(c) identifying the tumor in the subject based on detection step (b); and
(d) light irradiating the identified tumor at a specific wavelength, wherein upon the light irradiation, the photosensitizer generates cytotoxic reactive oxygen species, thereby treating the tumor.

In various embodiments of the theranostic method, the adsorption of the photosensitizer on the nanoparticles solubilizes the nanoparticles. In an embodiment, the nanoparticles are superparamagnetic iron oxide nanoparticles (SPIONs). In another embodiment, the photosensitizer is a chlorin or a derivative thereof. In an additional embodiment, the chlorin is Ce6. In a further embodiment, the chlorin derivative is amidochlorin p6 (ACP). In a still further embodiment, the chlorin derivative is single aspartyl Ce6 (N-aspartyl chlorin Npe6). In another embodiment, the chlorin derivative is pheophorbide a (2-deacetyl-2-vinylbacteriopheophorbide). In yet another embodiment, the chlorin is meso-tetra (3-morphlinomethyl-4-methoxyphenyl) chlorin (TMMC). In various embodiments of the theranostic method, the photosensitizer is a Ce6 derivative. In other embodiments, the Ce6 derivative is chlorin e6 ethylenediamide or a chlorin e6 and polyvinylpyrrolidone (Ce6-PVP) complex. In further embodiments, the imaging modality is x-ray imaging, computed tomography (CT), magnetic resonance imaging (MRI), photoacoustic imaging, fluorescence imaging, or fluoroscopy.

In a further aspect, the invention provides an azide-functionalized nanocluster comprising the nanocluster according to the invention, wherein the amphiphilic dye is bioconjugated to an azide. In certain embodiments, the amphiphilic dye is protoporphyrin IX (PpIX) or indocyanine green (ICG).

In an additional aspect, the invention provides a targeting ligand comprising azide-functionalized nanocluster In further aspect, conjugated to the ligand. In some embodiments, the ligand is a targeting antibody. In other embodiments, the targeting antibody is a humanized monoclonal antibody targeting human epidermal growth factor receptor-2 (HER2).

In another aspect, the invention provides a method for preparing a targeting antibody conjugated nanocluster, the method comprising:
reacting by copper-free click chemistry (i) an azide-functionalized nanocluster comprising the nanocluster of claim 28, wherein the amphiphilic dye is bioconjugated to an azide, and the nanocluster is carrier-free; and (ii) a targeting antibody functionalized with a dibenzocyclooctyne (DBCO) group, wherein the DBCO group labels the azide, thereby conjugating the antibody to the nanocluster.

In an embodiment of the method according to the invention, the method further comprises washing the antibody conjugated nanocluster to remove non-specifically bound antibody, wherein the washing is a high stringency washing. In another embodiment, the targeting antibody is a humanized monoclonal antibody targeting human epidermal growth factor receptor-2 (HER2). In yet another embodiment, the reacting is in vivo in live mammalian cells. In various embodiments, the reacting is in vivo in a subject. In certain embodiments, the reacting is in vitro. In particular embodiments, the amphiphilic dye is protoporphyrin IX (PpIX) or indocyanine green (ICG).

In a still further aspect, the invention provides a method for treating a subject having a tumor, the method comprising:

(a) administering the targeting antibody conjugated nanocluster of claim 71 to the subject, thereby increasing accumulation of the targeting antibody at the tumor;
(b) detecting the accumulation of the targeting antibody by an imaging modality;
(c) identifying the tumor in the subject based on detection step (b); and
(d) light irradiating the identified tumor at a specific wavelength, wherein upon the light irradiation, the photosensitizer generates cytotoxic reactive oxygen species, thereby treating the tumor.

In embodiments of the method according to the invention, the imaging modality is x-ray imaging, computed tomography (CT), magnetic resonance imaging (MRI), photoacoustic imaging, fluorescence imaging, or fluoroscopy. In specific embodiments, the amphiphilic dye is protoporphyrin IX (PpIX) or indocyanine green (ICG). In a further embodiment, the targeting antibody is a humanized monoclonal antibody targeting human epidermal growth factor receptor-2 (HER2). In a still further embodiment, the HER2 targeting antibody treats breast cancer.

In another aspect, the invention provides a method for producing a stable polymer-solubilized amphiphilic dye nanocluster, the method comprising:
(a) dissolving the amphiphilic dye in DMSO, wherein the amphiphilic dye is a photosensitizer, to prepare a photosensitizer solution;
(b) dissolving the polymer in toluene to prepare a polymer solution;
(c) combining the photosensitizer solution and the polymer solution into membrane-filtered water to prepare a mixture;
(d) sonicating the mixture of step (c) to form an emulsion;
(e) evaporating the toluene to form a toluene-free mixture;
(f) purifying the toluene-free mixture by dialysis to remove free amphiphilic dye and DMSO, thereby preparing the stable polymer-solubilized amphiphilic dye nanocluster.

In various embodiments, the polymer is a biodegradable polyester. In particular embodiments, the biodegradable polyester is polylactic acid (PLA), polyglycolic acid (PGA), poly-ε-caprolactone (PCL), polyhydroxybutyrate (PHB), and poly(3-hydroxy valerate)polycaprolactone, poly(ethylene succinate) (PESu), poly(propylene succinate) (PPSu) and poly(butylene succinate) (PBSu). In other embodiments, the photosensitizer is a chlorin or a derivative thereof. In specific embodiments, the chlorin is Ce6. In additional embodiments, the chlorin derivative is selected from the group consisting of amidochlorin p6 (ACP), single aspartyl Ce6 (N-aspartyl chlorin Npe6), and pheophorbide a (2-deacetyl-2-vinylbacteriopheophorbide). In further embodiments, the chlorin is meso-tetra (3-morphlinomethyl-4-methoxyphenyl) chlorin (TMMC). In other embodiments, the photosensitizer is a Ce6 derivative. In still further embodiments, the Ce6 derivative is chlorin e6 ethylenediamide or a chlorin e6 and polyvinylpyrrolidone (Ce6-PVP) complex.

All patents and literature references cited in this specification are hereby incorporated by reference in their entirety.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLES

Example 1

ICG and/or PpIX Coated SPIO Nanoclusters for Treating Cancer

Materials and Methods:

Superparamagnetic Iron Oxide (SPIO) Synthesis:

SPIO nanoparticles were prepared by thermal decomposition. Iron(III) acetylacetonate [Fe(acac)$_3$], 1,2-hexadecanediol, oleic acid, and oleylamine and benzyl ether were stirred under nitrogen. The mixture was heated to 200° C. for 15 min, and then under a blanket of nitrogen, heated to reflux (300° C.) for 1 h. After allowing the reaction to cool to room temperature, two volumes of ethanol were added and the resulting mixture was centrifuged (5500 g×15 min) to precipitate the nanoparticles. The particles were then allowed to air dry and dissolved in toluene. Large aggregates were removed by centrifugation at 3000 g×15 min.

ICG SPIO Nanocluster Synthesis:

A mixture (200 μL) containing indocyanine green (ICG) (2 mg into dimethylformamide) and SPIO (1.1, 2.2, 4.4, 6.6, and 8.8 mg based on the Fe concentration in toluene) was pipetted into a glass vial containing 4 mL of water, and the sample was sonicated until a homogenous solution was observed. The toluene was evaporated overnight. Dialysis was performed in 4 L of water to remove dimethylformamide. The nanoclusters were purified by passing through a MACS® (25 LD columns, Miltenyi Biotec, Germany) column.

PpIX/Ce6 SPIO Nanocluster Synthesis:

1 mg PpIX in 50 μL dimethyl sulfoxide (DMSO) was vortexed at 50° C. until PpIX becomes fully dissolved in DMSO. A mixture (200 μL) containing PpIX (1 mg into DMSO) and SPIO (1.1, 2.2, 4.4, and 6.6 mg based on the Fe concentration in toluene) was prepared and vortexed for 5 minutes. The mixtures were further mixed together and vortexed at 50° C. for ~10 minutes to ensure fully dissolved PpIX and then pipetted into a glass vial containing 4 mL of water. The sample was sonicated until the solution became homogenous. The toluene was evaporated overnight. Dialysis was performed in 4 L of water to remove dimethylformamide. The nanoclusters were purified by passing through a MACS® (25 LD columns, Miltenyi Biotec, Germany) column.

Preparation of ICG+Photosensitizer Nanoclusters:

SPIONs are synthesized by thermal decomposition. To prepare ICG/photosensitizer_nanoclusters, SPIONs (in toluene) ICG (in DMSO) and cyclic tetrapyrrole dyes (e.g., PpIX or chlorin e6 (in DMSO)) are mixed at a desired ratio. The SPION, ICG, and photosensitizer mixture are added to water and sonicated. The sample is left open to air overnight, allowing for the slow evaporation of toluene and formation of stable nanoclusters. Nanoclusters are further purified by dialysis or diafiltration. Magnetic purification (Miltenyi Biotec) can also be added as part of the purification procedure.

ICG-Gold Nanocluster Synthesis:

A solution of indocyanine green (ICG) was prepared (100 mg/mL in dimethylformamide), and 20 μL was dissolved into a mixture containing dimethylformamide and toluene (30 μL and 60 μL, respectively). A second solution was prepared containing 1.9-nm dodecanethiol-coated gold nanoparticles (40 mg/mL in toluene based on dry particle mass), and variable amounts (50-500 μL) were combined with the primary ICG solution. The resulting mixture was pipetted into a glass vial containing 4 mL of water, and the sample was sonicated until a homogeneous solution was observed. The toluene was evaporated overnight. Dialysis was performed in 4 L of water to remove dimethylformamide. The nanoclusters were purified by passing through a Sepharose CL-4B column (1.5×12 cm).

Results

The inventors of this application demonstrated that ICG-coated SPION nanoclusters (FIG. 1A) could assist with gross tumor resection, under photoacoustic (PA)-guidance (FIG. 11A), and increase progression-free survival in a murine flank tumor model (FIG. 11B). PA offers the advantage of greater penetration depth (>6×) than fluorescence imaging. A photosensitizer (e.g., PpIX or chlorin e6)) can be added to this nanoplatform for photodynamic therapy treatment (FIG. 17). Notably, this nanoplatform can be composed solely of three reagents (i.e. SPIONs, ICG, and a photosensitizer, e.g. either PpIX or chlorin e6), all of which have been clinically tested or approved in some form or composition and are generally considered safe. No additional materials (e.g., surfactants, polymers, etc.) or modifications are required.

The inventors demonstrated that photoporphyrin IX (PpIX)-coated SPION nanoclusters can be produced in large-scale, have a high PpIX loading efficiency (>90%), a high loading capacity (~50% PpIX w/w), high stability, and high potency (FIG. 15). Moreover, the inventors have demonstrated that the PpIX-coated SPION nanoclusters can lead to a significant reduction in tumor growth rate and an increase in survival compared with PpIX alone and even PpIX-loaded PEG-PCL micelles (FIG. 15D). The improvement with these nanoclusters over PpIX-loaded micelles is at least partly due to the increased stability (i.e. reduced leakage/dissociation of PpIX) in serum. The nanoclusters are quite unique, since they are formulated with only PpIX and SPION. No additional stabilizing materials are utilized, similar to the ICG-coated SPIONs described above. While these types of surfactant-/polymer-free nanoformulations cannot be prepared with any compound, the inventors found that very stable nanoclusters can be formed with ICG, PpIX, Chlorin e6 and similar cyanine and cyclic tetrapyrrole dyes compounds.

Figure 16A:
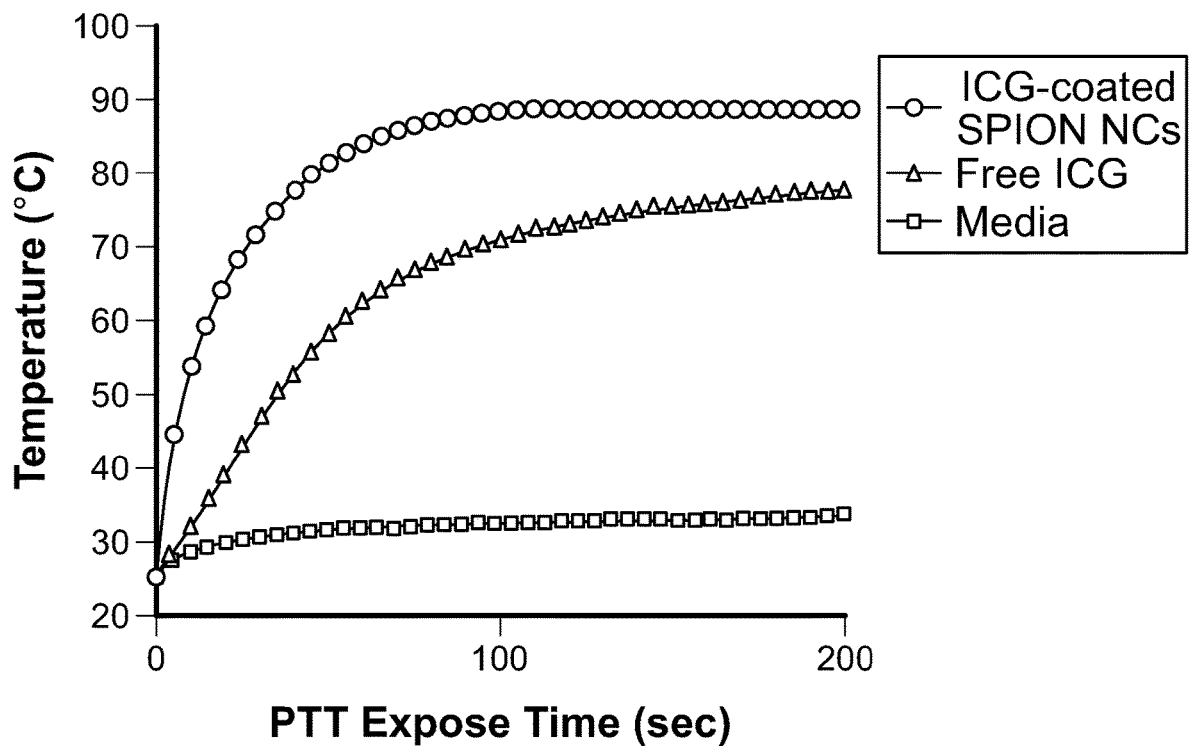
FIGS. 16A-16B.
Figure 16B:
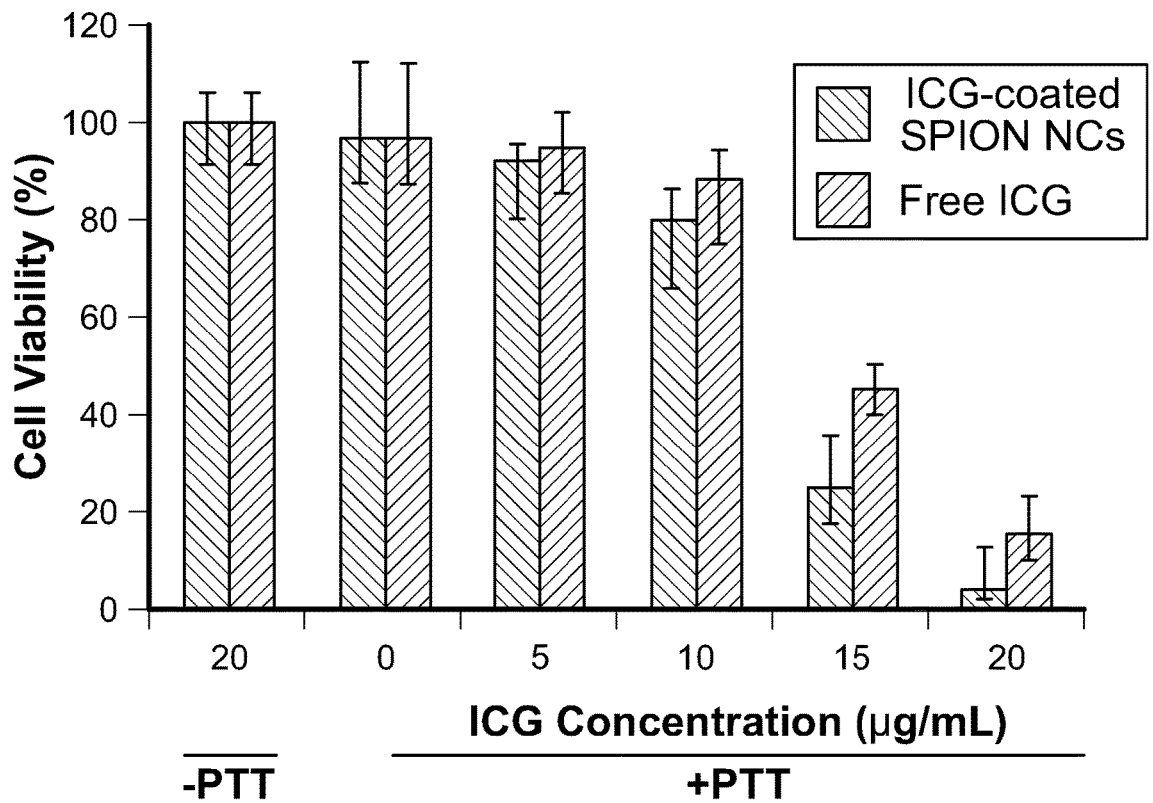
Figure 17A:
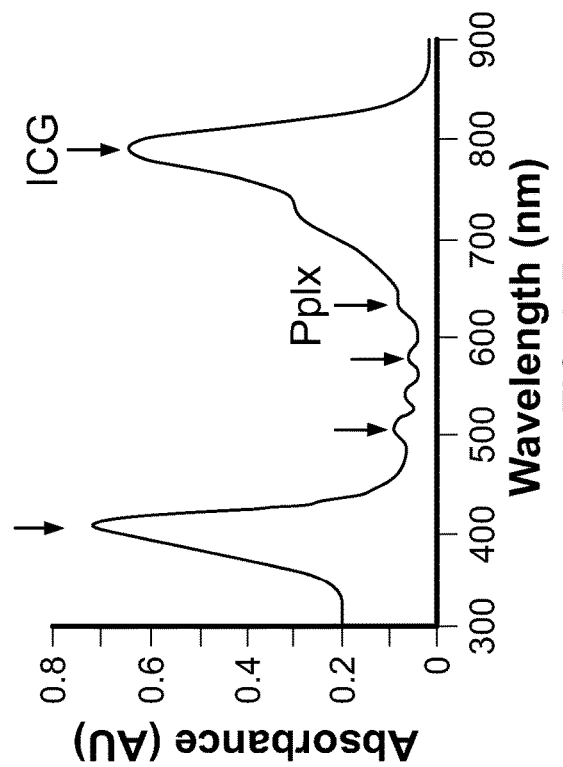
FIGS. 17A-17D.
Figure 17B:
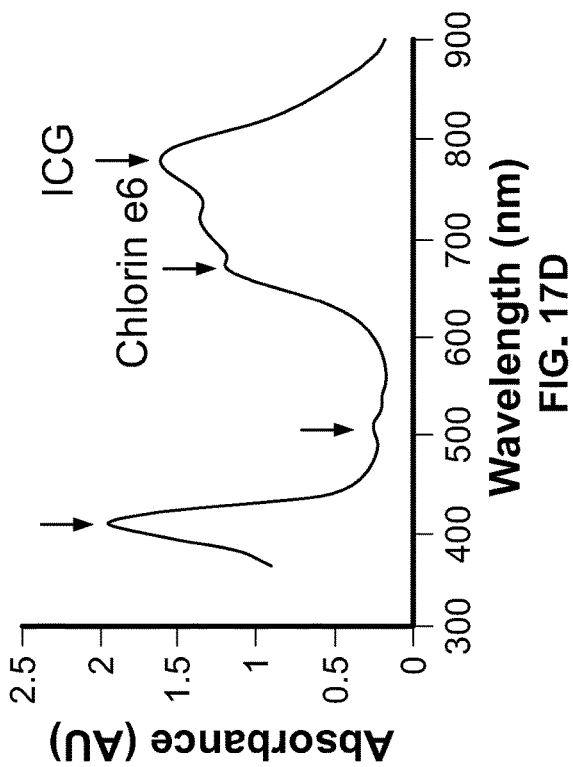
Figure 17C:
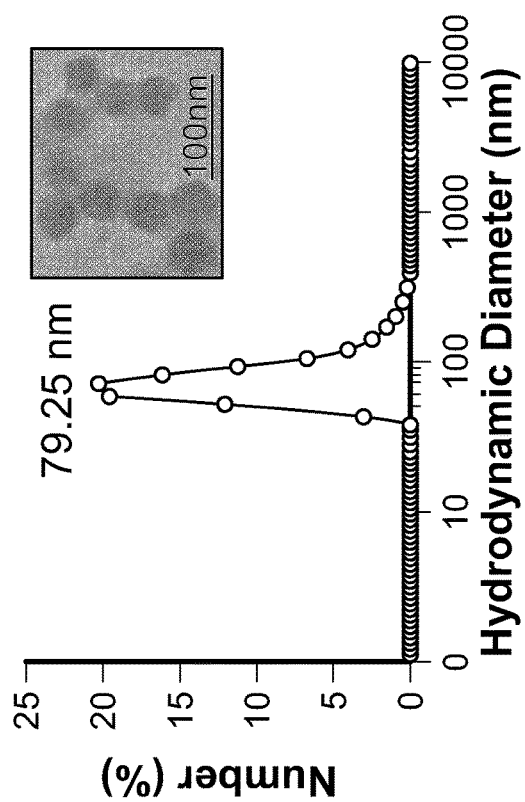
Figure 17D:
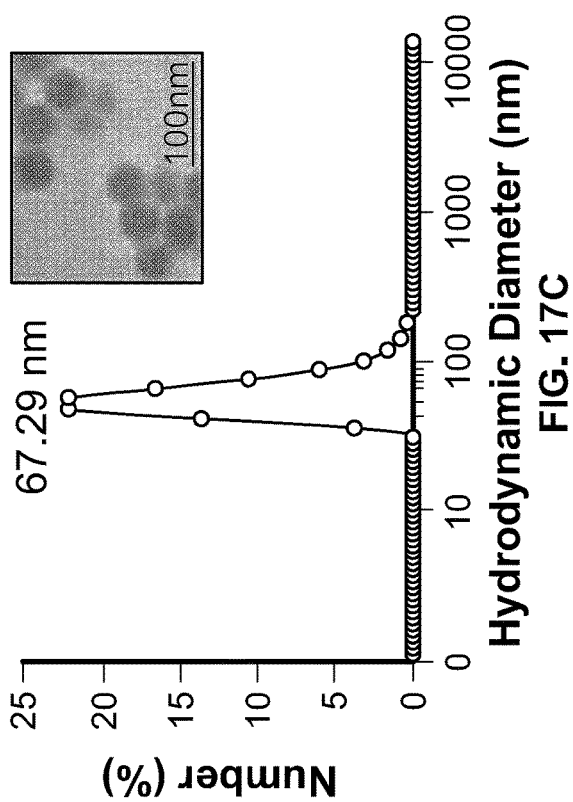
Figure 18:
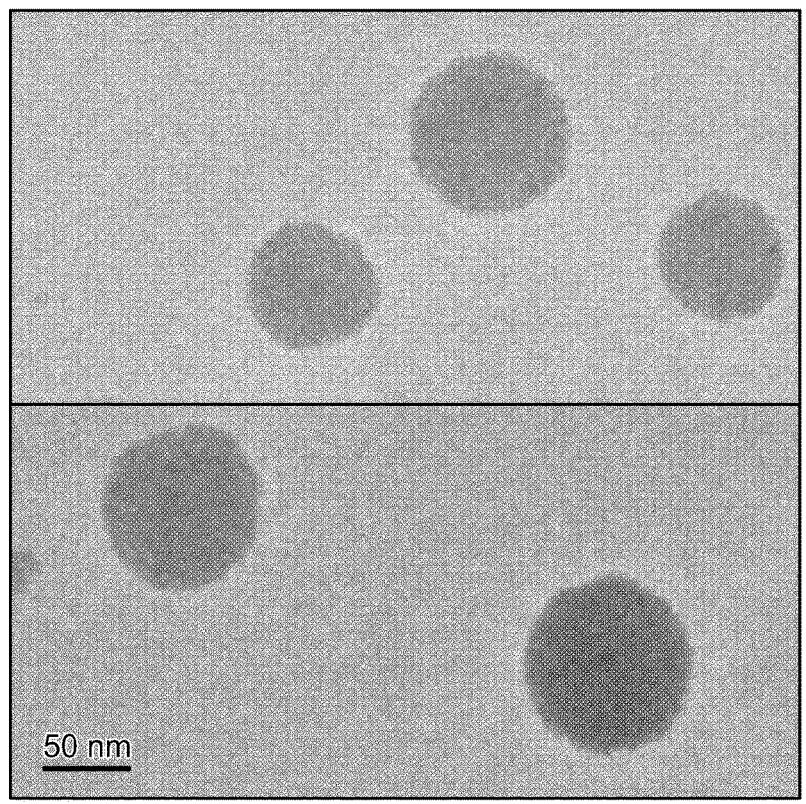
FIG. 18. Transmission electron micrograph of ICG-coated gold nanoclusters (scale bar: 100 nm).

A photosensitizer (PpIX or Chlorin e6), ICG, and SPION can be combined into a single nanocluster. This allows imaging across multiple imaging modalities (MR, optical, and photoacoustic) and allows for PDT and/or photothermal therapy (PTT), individually or in combination. ICG-coated SPIONs act as effective PTT agents (FIG. 16). Moreover, it has been shown that PTT and PDT can be combined to create a significant synergistic effect.

Figure 9A:
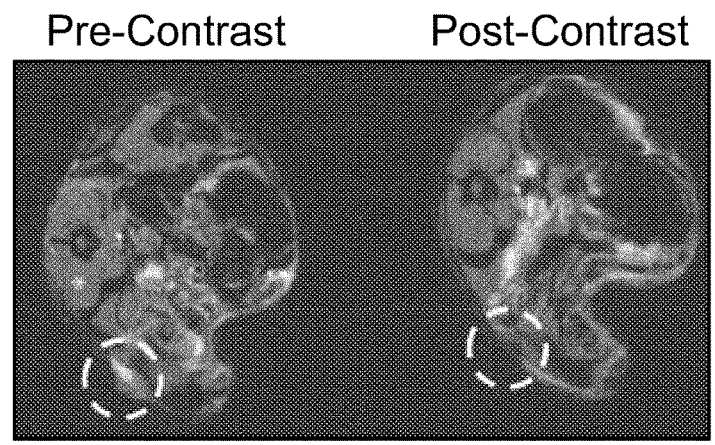
FIGS. 9A-9C.

Current neuro-navigation techniques allow neurosurgeons to make judgments between preoperatively acquired MRI scans and areas felt to represent tumor in the operating room. However, even if the co-registration of the surface anatomy of the skin is precise, the brain can shift during surgery. Because of this situation, many centers have used an intraoperative MRI scanner within the operating room environment, but the timing, dose, and type of intraoperative contrast agent used may affect which areas of the tumor (or brain) are ultimately resected. Intraoperative MRI also remains an expensive technology in terms of cost and time. These shortcomings have been partly responsible for the interest in systemically delivered fluorescent compounds that closely correlate with Gd-enhanced pre-operative scans. Unfortunately, it has been shown that current contrast agents like ICG do not exhibit a high specificity (45%) for gadolinium-enhancing specimens. Nanoclusters, which possess a PA/optically detectable near-infrared dye (e.g. ICG) that is stably associated with an MRI-detectable magnetic nanoparticle, can be used to directly relate preoperative radiologic findings with the visual presentation of pathology during surgery (FIG. 9).

Example 2

Photoacoustic-Guided Surgery with Indocyanine Green-Coated Superparamagnetic Iron Oxide Nanoparticle Clusters A common cause of local tumor recurrence in brain tumor surgery results from incomplete surgical resection. Adjunctive technologies meant to facilitate gross total resection have had limited efficacy. Contrast agents used to delineate tumors pre-operatively cannot be easily or accurately used in a real-time operative setting. Although multimodal imaging contrast agents have been developed to help the surgeon discern tumor from normal tissue in the operating room, these contrast agents are not readily translatable. The inventors of this application have developed a contrast agent comprised solely of two FDA-approved components, indocyanine green (ICG) and superparamagnetic iron oxide (SPIO) nanoparticles with no additional amphiphiles or carrier-materials, to allow pre-operative detection by MRI and intraoperative photoacoustic (PA) imaging. The encapsulation efficiency of both ICG and SPIO within the formulated clusters is ~100% and the total ICG payload is 20-30% of the total weight (ICG+SPIO). The ICG-SPIO clusters are stable in physiologic conditions, can be taken up within tumors by enhanced permeability and retention, and are detectable by MRI. In a pre-clinical surgical resection model in mice following injection of ICG-SPIO clusters, animals undergoing PA-guided surgery demonstrated increased progression-free survival compared to animals undergoing microscopic surgery.

Materials and Methods

Superparamagnetic Iron Oxide (SPIO) Synthesis: SPIO nanoparticles were prepared by thermal decomposition as previously described with some modifications as noted here. Briefly, iron(III) acetylacetonate [Fe(acac)$_3$] (2 mmol), 1,2-hexadecanediol (5 mmol), oleic acid (2 mmol), and oleylamine (6 mmol) and benzyl ether (20 mL) were stirred under nitrogen. The mixture was heated to 200° C. for 15 min, and then under a blanket of nitrogen, heated to reflux (300° C.) for 1 h. After allowing the reaction to cool to room temperature, two volumes of ethanol were added and the resulting mixture was centrifuged (5500 g×15 min) to precipitate the nanoparticles. The particles were then allowed to air dry and dissolved in toluene. Large aggregates were removed by centrifugation at 3000 g×15 min.

ICG SPIO Cluster Synthesis:

A mixture (200 µL) containing indocyanine green (ICG) (2 mg into dimethylformamide) and SPIO (1.1, 2.2, 4.4, 6.6, and 8.8 mg based on the Fe concentration in toluene) was pipetted into a glass vial containing 4 mL of water, and the sample was sonicated until a homogenous solution was observed. The toluene was evaporated overnight. Dialysis was performed in 4 L of water to remove dimethylformamide. The ISCs were purified by passing through a MACS® (25 LD columns, Miltenyi Biotec, Germany) column. Finally, the purified clusters were characterized by UV-absorption spectroscopy (Varian, 100 Bio), plasma optical emission spectroscopy (ICP-OES) (Spectro Genesis, GMBH) DLS (Malvern, Zetasizer, Nano-ZS), TEM (JOEL 1010) analysis, and relaxometry (Bruker, mq60 NMR analyzer). The ICG and SPIO encapsulation efficiency (EE) was calculated according to the following equation:

$$\text{Encapsulation efficiency (\%)} = \frac{\text{Weight of ICG in purified nanoparticles}}{\text{Weight of ICG used in synthesis}} \times 100$$

ICG and Iron concentrations were quantified by UV-absorption and ICP-OES, respectively.

ISC Release and Stability Studies:

The amount of ICG adsorbed on ISCs in fetal bovine serum (FBS) was determined based on absorbance measurements. A 1:10 dilution of ISCs in water:FBS solution was prepared and stored in the dark at 37° C. with shaking. The pH was 7.4 for mixtures. Aliquots were run through MACS columns to separate ICG released (ICG bound to serum proteins+free) from that still adsorbed onto SPIO cores. 'Free ICG' considers ICG that is not associated with the SPIO cores and exists bound to serum proteins (majority) or in free form. The peak absorbance spectra of ICG in the particle-adsorbed compartment was determined by dissolving ISCs in DMF (dissolving free ICG in DMF). Normalized peak absorbance was measured over time. Release of ICG from ISCs was measured, over time, as a fraction of the total amount of ICG in ISCs at t=0. Absorbance was used to determine the amount of ICG in solution (based on a standard curve of ICG in DMF). In addition, DLS was used to measure the particle size based on mean intensity (%) measurements taken over a total of 8 days in water and FBS. Finally, ISCs were incubated in water and FBS at 37° C. Aliquots taken from the sample (ISCs:solvent) were tested for magnetic properties (T2 mode).

Mtt Assay:

U251 human glioblastoma cells ($2.6 \times 10^4$ cells per well) were seeded in 96-well plates and incubated overnight to allow the cells to attach to the surface of the wells. The cells were then mixed with increasing concentrations of ISCs for 24 hrs and the cell viabilities were determined by a standard MTT assay.

Cell Line Selection and Initial Animal Studies:

Athymic nude female mice (aged 6 weeks) were utilized for the study (n=12). U251 human glioma cells expressing firefly luciferase (U251+Luc) were utilized for (1) the invasive phenotype observed across studies and (2) ease of detection by bioluminescence. U251 demonstrates the histological and MR imaging characteristics of glioblastoma as seen clinically in humans. These cells were cultured and implanted in the right flank as previously described protocols[44,46,47]. Briefly, cells were passaged in DMEM with antibiotics (1% penicillin/streptomycin). Non-enzymatic dissociation media was used. $5 \times 10^6$ cells were implanted in the right flank of the mice at approximately 6-8 weeks of age; animals were observed every 4 days to evaluate tumor growth. In a subset of animals, bioluminescence testing was undertaken to confirm peak timing in terms of administration of D-luciferase. Dose testing (0.25, 1, 5 mg/kg ICG in ISCs injected intraorbital) was performed with no toxicity observed in animals. Visualization by in vivo fluorescence imaging and MR imaging (9T) confirmed the presence of ISCs at 24 hours. Equivalent concentrations of ICG free dye were also evaluated. Instrumentation/parameters: Perkin Elmer IVIS Spectrum In Vivo Imaging System (excitation 745 nm, emission 800 nm, lamp level=low, exposure times: (A) 1, (B) 3, (C) 10, binning 4, f=1). Bioluminescence studies were performed 12 minutes following IP injection of D-luciferin sodium salt based on peak signal time (200 uL, 15 mg/mL intraperitoneal injection).

All animals in this study were anesthetized according to an approved IACUC protocol (1-2.5% inhalational isofluorane with meloxicam dosed 5-10 mg/kg subcutaneous given every 12-24 hours) and euthanized by $CO_2$ inhalation/cervical dislocation. Animals were monitored by regular staff and by veterinarians if they demonstrated illness outside of protocol. Histology was performed using hematoxylin and eosin staining. Tumors were surgically removed and resection sites were catalogued for gross pathologic findings. In a group of 12 mice with U251 orthotopic flank xenografts, only 1 of 4 animals (25%) with tumors less than 7 mm in size exhibited myoinvasion on histology as compared to 100% of 8 animals with tumors >7 mm in size showing histologic evidence of myoinvasion.

Fluorescence Imaging:

Serial 1/2× dilutions from [5 μg/ml] to 1/16×[0.31 μg/ml] of ISCs were used in a 120-well plate as a phantom. An equivalent amount of ICG was used as control Images were acquired with a Perkin Elmer IVIS Spectrum In Vivo System (excitation 745 nm, emission 800 nm, lamp level=low, exposure time=10 s, binning 4, f=1).

MRI Phantom and Animal Imaging by MRI:

Relaxometry measurements were performed in T2* mode (Varian, 9.4 Tesla); Iron concentration was quantified by ICP-OES. A plastic 120-well plate (MR phantom) was used in order to test the T2 hypointensity associated with ISCs compared to control (free ICG at equivalent concentrations) on a 9T magnet. [Fe] concentrations were as follows: 1, 0.5, 0.25, 0.125, and 0.0625 mM. Mice bearing U251 flank xenografts were injected with 1 mg/kg ISCs via intraorbital injection. Imaging was performed 24 hours after injection. Contrast enhancement on T2*-weighted imaging (seen as hypoenhancement following injection of ISCs) was quantified using ImageJ. Pre- and post-injection imaging parameters (gems, TR200, TE3, 1 avr) were matched and confirmed by an attending radiologist. Imaging analyses were performed on T2-weighted imaging sequences, using the tumor (signal) and the paraspinous musculature as background. Comparison of means testing was performed to compare the mean SBRs of animals pre-injection versus post-injection.

Photoacoustic Phantom and Animal Imaging:

Photoacoustic (PA) testing on the Vevo Lazr device (VisualSonics, Toronto CA) was performed in 0.5 mm diameter polyethylene tubing submerged in water at a depth between 1-2 cm. Samples were injected (50 μL) into the tubing prior to imaging Spectra and imaging data were collected. ISCs were tested according to ICG concentrations (0.5, 0.45, 0.40, 0.35, and 0.3 mg/mL) with the following settings: ultrasound gain+27 dB, PA gain 25 dB, priority 95%, distance 1.2-1.5 cm from the transducer. PA average (Average PA intensity (arbitrary units, AU) were computed by the built-in imaging software using photoacoustic intensity per unit two-dimensional area. 3D-mode testing of ISCs (with different concentrations of ICG) was performed on the phantom demonstrating increased PA intensity with concentration. The LZ550 transducer was utilized (Axial resolution 44 μm, broadband frequency 32-55 MHz).

ISCs were intravenously (orbital) injected into mice bearing U251 (+Luc) flank xenografts. Twenty-four hours following injection (1 mg/kg based on ICG weight), the animals were imaged with excitation at 850 nm with the following parameters: ultrasound gain+27 dB, PA gain 25 dB, priority 95%. 1 mg/kg was chosen as a candidate dose based on human dosing for solid tumor imaging and previously published data on ICG and iron oxide dosing required for MR imaging[14-16].

Surgical Resection Trial:

Twenty-four mice (N=24) were implanted with U251 (+Luc) cells expressing as above and randomized to either a photoacoustic (PA)-guided surgery arm (N=12) or microscopic resection arm (N=12). The animals in both groups undergoing surgery had operations performed using 3.5× loupe magnification and white light, once the tumors reached >7 mm in their largest dimension. The PA-guided surgery arm underwent Photoacoustic imaging studies done as part of surgery to identify areas of residual tumor following initial resection. Following surgery, all animals were identified/tagged and monitored for recurrence by a different individual than the operating surgeon at varying timepoints to assess for survival and progression of disease. Animals were injected with 1 mg/kg ISCs based on ICG weight (intraorbital) and imaged 24 hours following injection as above. For all animals, PA imaging parameters were kept constant (ultrasound gain+27 dB, PA gain 25 dB, priority 95%) including time-gain constant.

Progression-free survival data in both groups was calculated based on periodic assessments with bioluminescence imaging as previously described. Timepoints for intraperitoneal injection of D-Luciferin (to assess recurrence) were at 0, 10, 25, and 42 days for the microscopic surgery cohort and at 0, 12, 25, and 42 days for the PA-guided surgery cohort. Bioluminescence studies were performed 12 minutes following IP injection of D-luciferin sodium salt based on peak signal time (200 uL, 15 mg/ml intraperitoneal injection). Animals were monitored for pain (as above) and treated appropriately as per the IRB/IACUC protocol. Kaplan-Meier and log-rank statistical analyses were performed in Stata v.12.

Figure 1B:
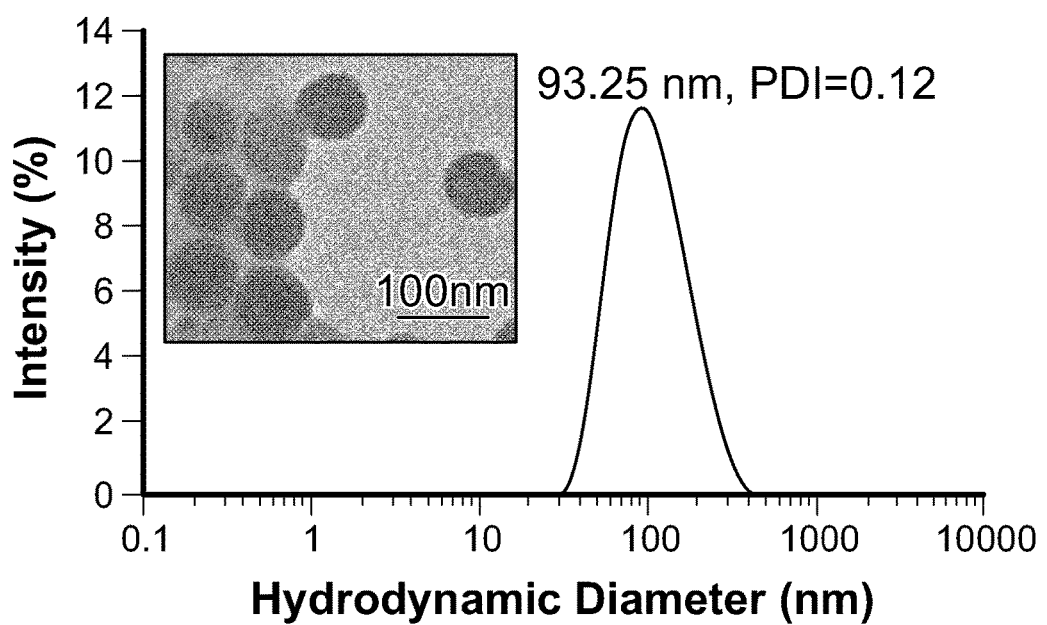

Results:

Preparation and Characterization of Indocyanine Green-Coated Superparamagnetic Iron Oxide Clusters:

Indocyanine green (ICG)-coated superparamagnetic iron oxide (SPIO)-nanoparticle clusters (ISCs) (FIG. 1) were formed via an inverse emulsion with ICG and SPIO nanoparticles (diameter=7.3±1.0 nm; FIG. 2) in the oil-phase. No additional amphiphiles (e.g. polymers, surfactants, etc) or other carrier-materials were included in the emulsion. The generated ISCs are soluble in water, with ICG acting as the amphiphilic solubilizing agent (FIG. 1A). The synthetic approach is highly reproducible (Table 1), resulting in ISCs that have an average diameter of 96.87±7.8 nm and a polydispersity (PDI) index of <0.18 (based on dynamic light scattering, DLS) (FIG. 1B). ISCs are visible on TEM as densely packed clusters of SPIO nanoparticles (FIG. 1B, inset). The loading efficiency is >95% for SPIO and >90% for ICG, when the ICG:Fe ratio (w/w) is in the range of 1:4 to 1:3 (Table 2). A further increase in the ratio of ICG:Fe during micelle formation does not result in significantly more ICG per cluster, but rather just a reduction in the ICG encapsulation efficiency. Accordingly, regardless of the starting ICG:Fe ratio (w/w), from 1:4 to 2:1, the resultant ISCs have remarkably similar physical-chemical properties. The final payload of ICG for each of the synthetic conditions tested was 20-30% of the total weight (ICG+Fe).

TABLE 1

Repeatability of ISC Synthesis

|  | ISC Batch 1 | ISC Batch 2 | ISC Batch 3 | Average | St. Dev. |
|---|---|---|---|---|---|
| Hydrodynamic Diameter (nm) | 102.8 | 87.98 | 99.82 | 96.87 | 7.84 |
| PDI | 0.171 | 0.172 | 0.138 | 0.16 | 0.019 |
| Relaxivity (r2) ($mM^{-1}s^{-1}$) | 338 | 308 | 309 | 318 | 17.4 |

TABLE 2

ICG Encapsulation Efficiency and ISC physical chemical properties as a function of starting ICG:Fe ratio (w/w)

| | Starting ICG:Fe Ratio (w/w) | | | | |
|---|---|---|---|---|---|
| | 2:1 | 1:1 | 1:2 | 1:3 | 1:4 |
| Encapsulation Efficiency (%) | 41 | 60 | 83 | 93 | 100 |
| ICG Payload: ICG/ (ICG←Fe) (%) | 27.33 | 30 | 27.66 | 23.25 | 20 |
| Relaxivity (r2) ($mM_{-1}s_{-1}$) | 295 | 301 | 315 | 350 | 345 |
| Hydrodynamic Diameter (nm) | 109 | 92 | 91 | 89 | 93 |
| PDI | 0.195 | 0.190 | 0.171 | 0.163 | 0.195 |

Figure 1C:
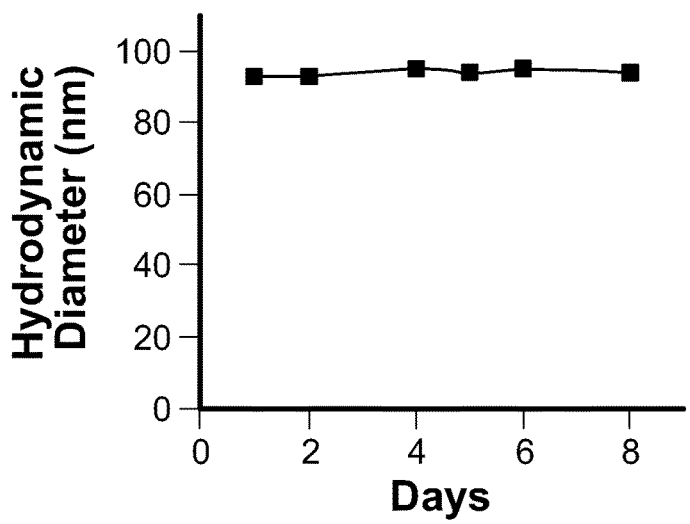
Figure 1D:
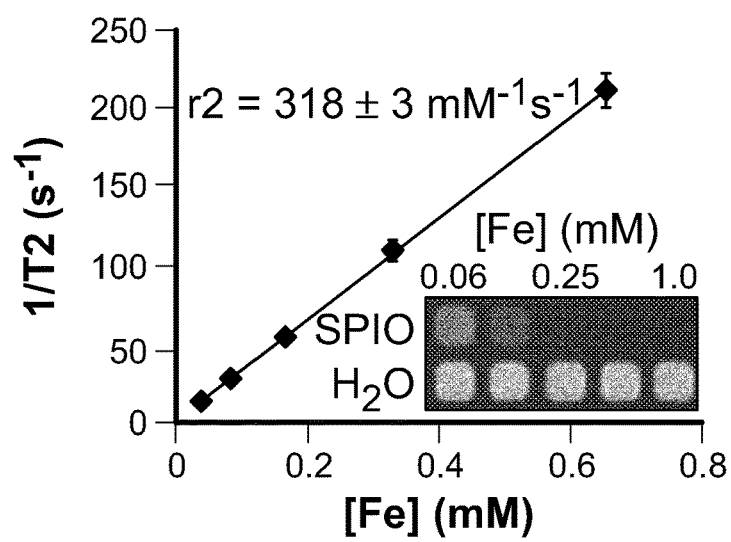
Figure 1E:
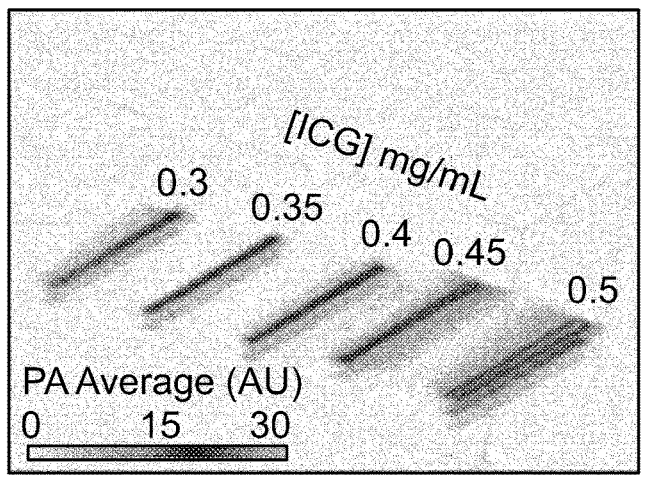
Figure 2A:
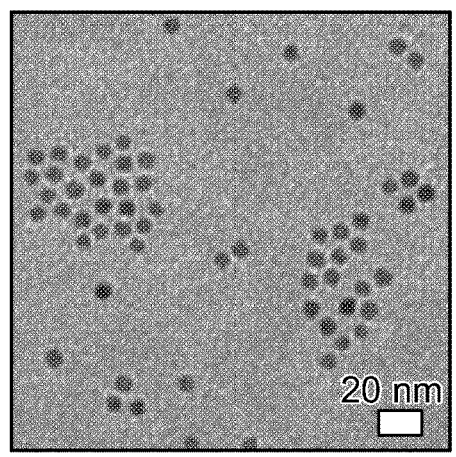
FIGS. 2A-2B.
Figure 2B:
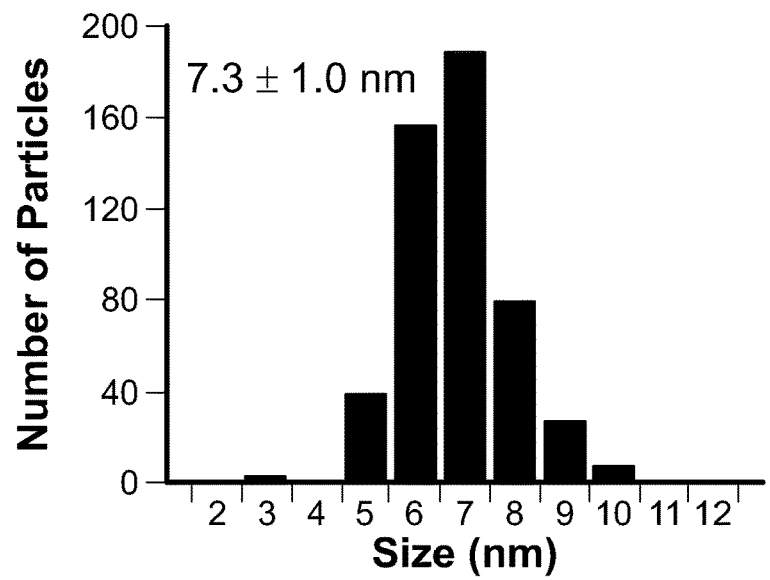
Figure 3:
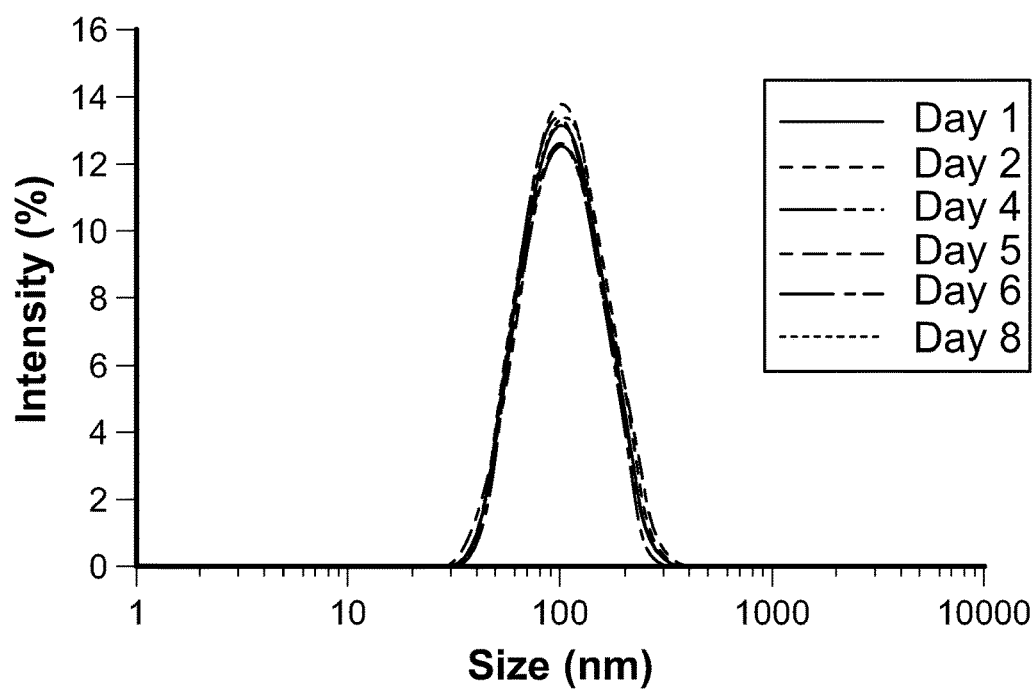
FIG. 3. Dynamic light scattering (DLS) results of ICG SPIO clusters (ISCs) over time in water, 25 C. Size measured as intensity %.
Figure 4:
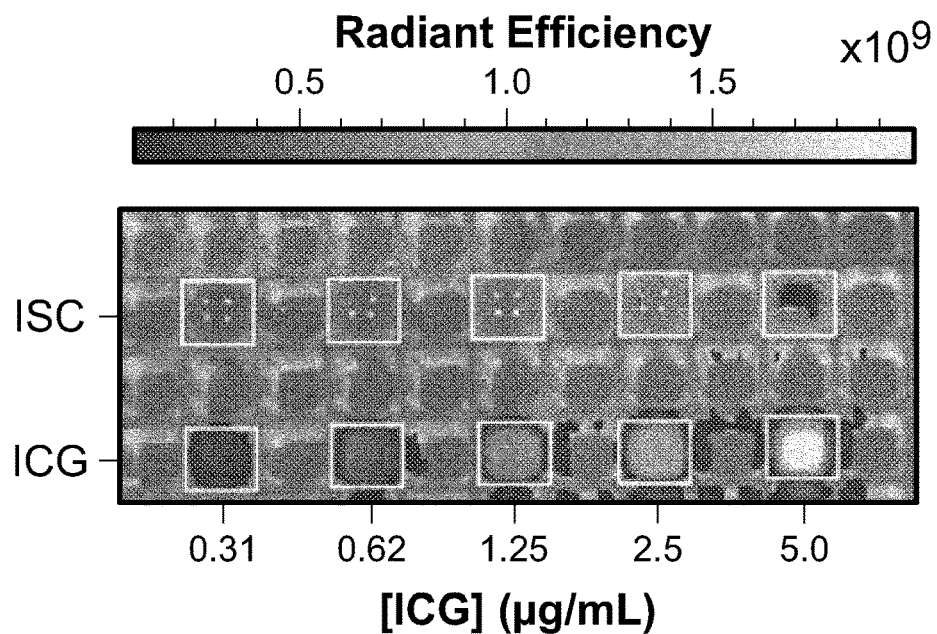
FIG. 4. Fluorescent image of a microplate containing increasing concentrations of ISCs (top row) and ICG dye (bottom row) in water. Instrumentation/parameters: Perkin Elmer IVIS Spectrum In Vivo System (excitation 745 nm, emission 800 nm, lamp level=low, exposure time=10 s, binning 4, f=1).
Figure 5:
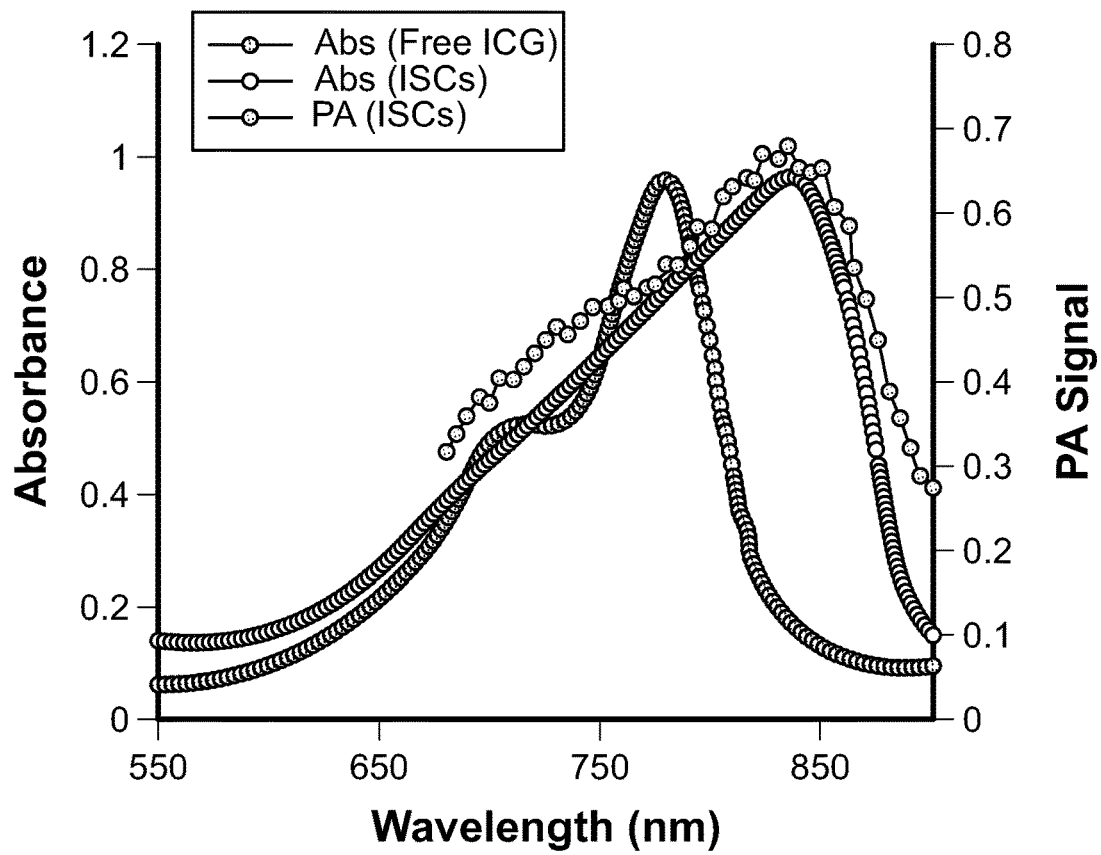
FIG. 5. Absorbance and Photoacoustic (PA) spectra of ICG SPIO clusters (ISCs) show a red-shifted peak wavelength of ~850 nm relative to the absorbance spectra of free ICG.

The ISCs are highly stable in water, with no observable change in size over 8 days, based on DLS measurements (FIG. 1C and FIG. 3). Relaxometry measurements revealed an average r2 value of 318±3 $mM^{-1}$ $s^{-1}$ and MR images of a phantom confirmed strong T2 contrast relative to controls (FIG. 1D). Given the high concentrations of ICG and SPIO present in the final nano-formulation, ISC fluorescence is extremely low, due to both self-quenching and iron-mediated quenching (FIG. 4); however, a robust photoacoustic (PA) signal is detectable, even when ISCs within polyethylene tubing are submerged at a depth of 1-2 cm in an aqueous (e.g. water) fluid (FIG. 1E). Spectral analysis of ISC absorbance and the PA signal reveals a red-shifted peak (~835 nm), relative to the absorbance peak of free ICG (~780 nm; FIG. 5).

Figure 6A:
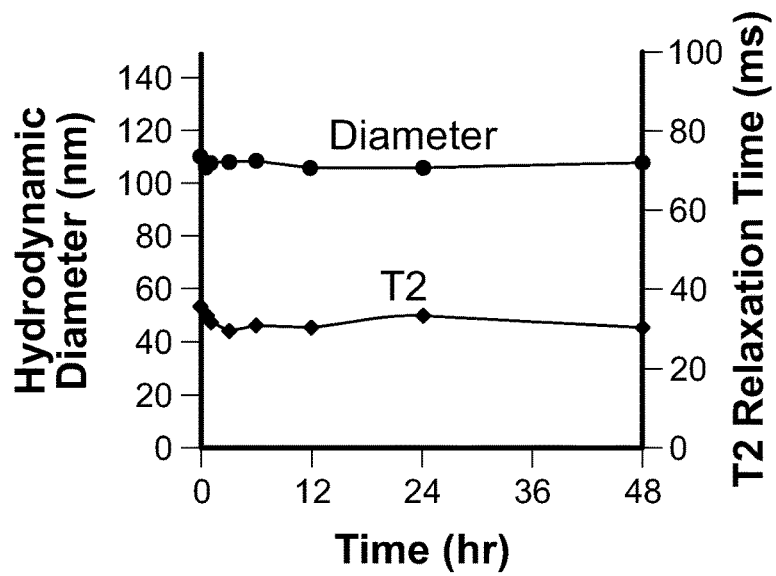
FIGS. 6A-C.
Figure 6B:
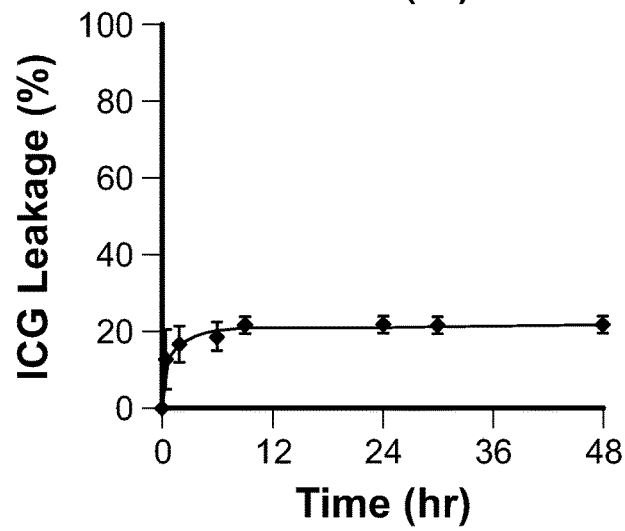

Evaluation of ISCs within Biological Samples:

To evaluate ISC stability under physiological conditions, the ISCs were diluted in fetal bovine serum (FBS) and kept at 37° C. under constant shaking. A slight (~10 nm) increase in the hydrodynamic diameter of ISCs was observed immediately after addition to serum, consistent with some protein absorption. However, no aggregation or precipitate was observed and there was no significant change in the T2 relaxation time (FIG. 6A). Approximately 20% of the surface-bound ICG was released from the ISCs within the first few hours after addition of serum, but then no further release was detectable for up to 48 hours (FIG. 6B). These findings suggest that the ICG forms a highly stable interaction with the SPIO surface.

Figure 6C:
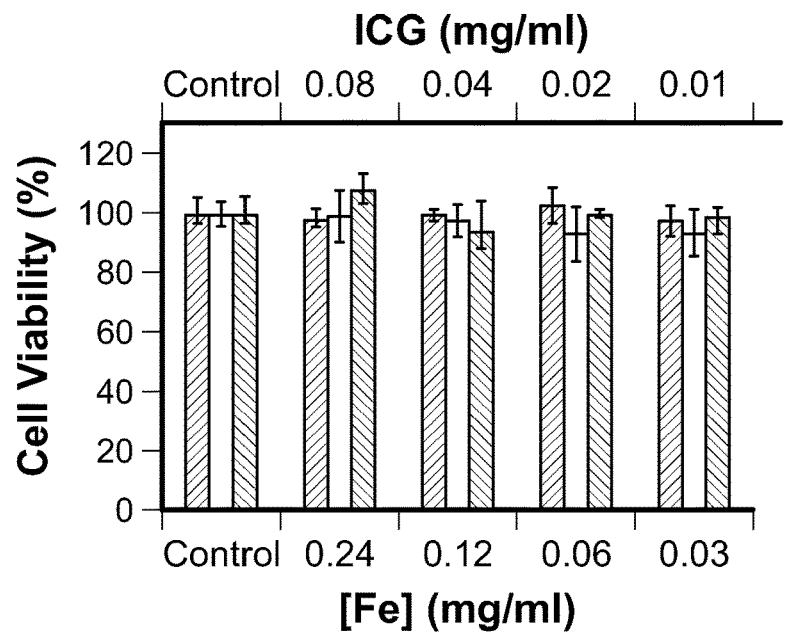

The cytotoxicity of the ISCs was examined in an MTT cell proliferation assay. Specifically, increasing concentrations of ISCs were incubated with U251 glioblastoma cells, human umbilical vein endothelial cells (HUVEC), and human embryonic kidney (HEK) 293T cells. It was found that the ISCs had no effect on the proliferation of any of the cells tested, up to a concentration of 0.24 mg Fe/mL (FIG. 6C).

Figure 7:
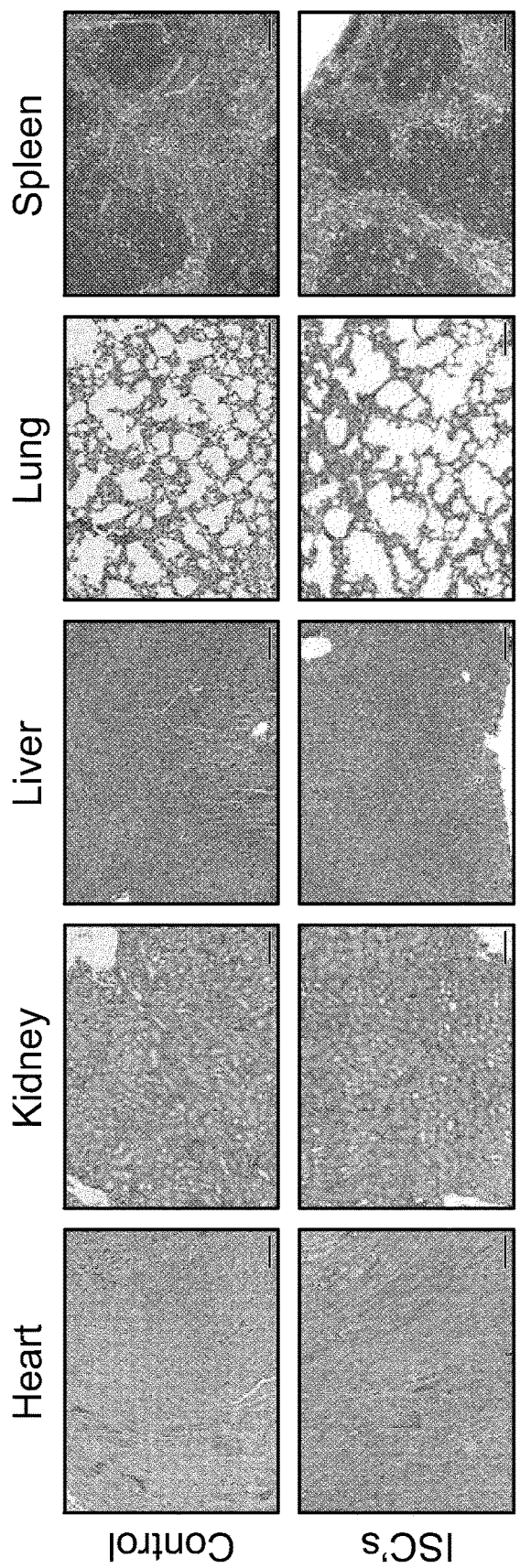
FIG. 7. Histology of various organs for mice treated with ISCs. Mice received a single intravenous injection of either PBS (control) or ISC (1 mg/kg, based on ICG weight). Organs were harvested 24 hrs post-injection. Tissues were sectioned and stained with H&E and images were acquired via light microscopy (scale bar=100 µm).

To evaluate the potential cytotoxicity of ISCs in mice, histological analysis was performed on the liver, spleen and kidney 1 day following the injection of ISCs (1 mg/kg, based on ICG weight) into C57BL/6J mice. Hematoxylin and eosin (H&E) staining of these organs showed no evidence of abnormal pathology or adverse effects (FIG. 7).

Small Animal Imaging: Magnetic Resonance and Photoacoustic Imaging

Figure 8B:
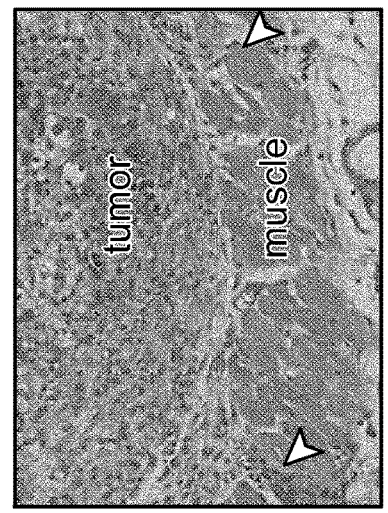
FIGS. 8A-8B. Histological sections of a human glioblastoma U251 flank tumors in mice. Gross pathologic findings are notable for evidence of myoinvasion (black arrowheads).
Figure 8A:
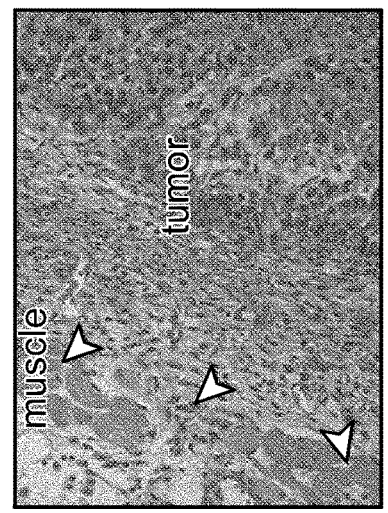

To assess the contrast-enhancing capabilities of ISCs in a murine tumor model, the human glioblastoma cell line U251 was selected and implanted in the flank of athymic nude mice. U251 tumors exhibit gross pathologic evidence of tumor myoinvasion (noted with tumor growth >7 mm in size) (FIG. 8). Nests of tumor cells were evident throughout the adjacent musculature. The U251 cells were engineered to express firefly luciferase, to allow tumor cells to be detected in live animals (for recurrence studies).

Figure 9B:
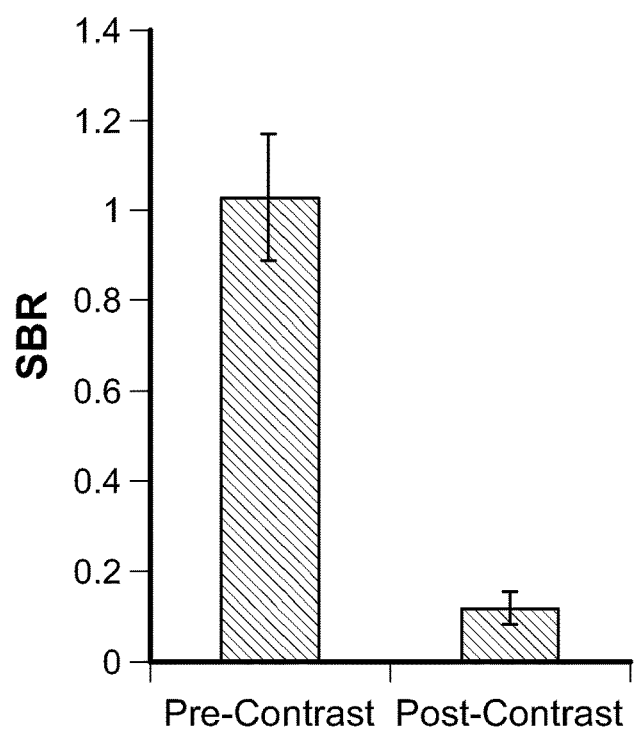
Figure 10:
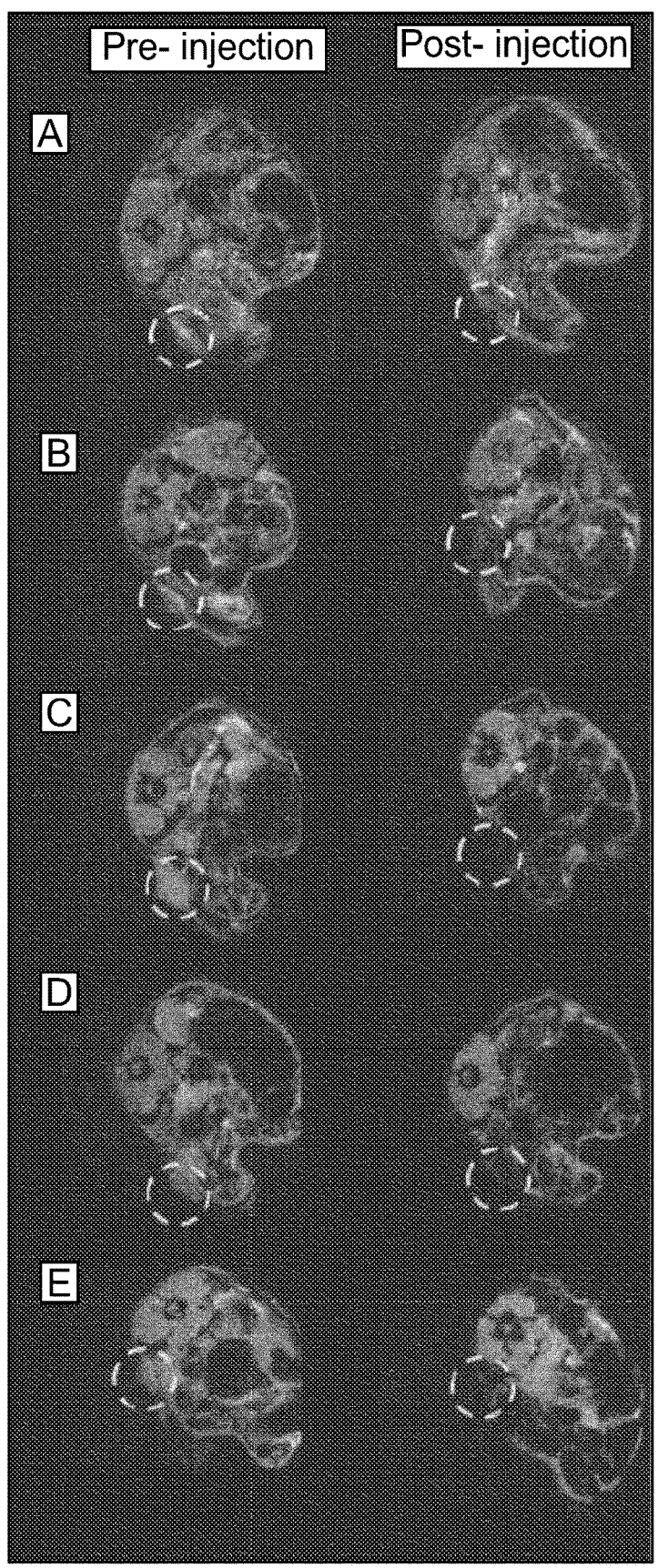
FIG. 10. T2-weighted magnetic resonance (MR) imaging before (left) and 24 hours after (right) intravenous (intraorbital) injection of 1 mg/kg ISCs by ICG weight into mice bearing U251 orthotopic flank xenografts. Yellow circles denote location of the flank tumor.

MR imaging before and 24 hours after injection of 1 mg/kg ISCs (based on ICG weight) revealed a notable loss in signal (i.e. hypointensity) in the flank tumors following injection (FIG. 9A and FIG. 10), consistent with the accumulation of SPIO nanoparticles. Tumor-specific accumulation of ISCs is likely a consequence of enhanced permeability and retention (EPR) and has been demonstrated at 24 hours following intravenous injection[16,21-23]. Signal-to-background (SBR) measurements were made using the tumor and the paraspinous musculature as background. The post-injection SBR was significantly lower at 0.12+/−0.03 compared to pre-injection SBR of 1.03+/−0.14, p<0.001 (FIG. 9B).

Figure 9C:
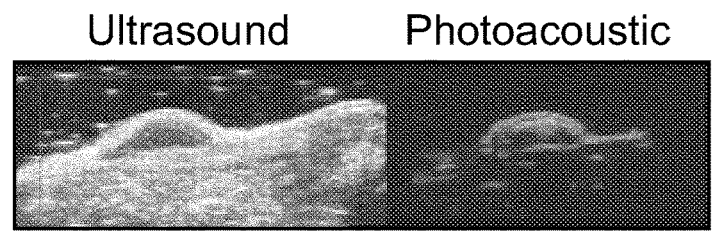

ISCs were also detectable via PA imaging, 24 hours post-injection (1 mg/kg), as noted by the appearance of a signal with a peak wavelength at ~850 nm (ultrasound gain+27 dB, PA gain, 25 dB, priority 95%) (FIG. 9C). No PA signal was observed pre-contrast. The PA signal was often limited to the outer surface of the tumor and was not always detectable throughout the entire tumor mass; however, partial resection of the tumor showed that the ICS nanoclusters were in fact present within the tumor core (FIG. 11A). This suggested that ICSs could be used to detect residual tumor tissue during surgery and further supported the use of ISCs for image-guided surgery.

Notably, ISCs within the tumor were also detectable via fluorescence (FIG. 12), 24 hours post-injection, despite the significant degree of quenching in the stock formulation. The fluorescent signal within the tumor was significantly more robust than in animals injected with an equivalent dose of free ICG, likely because of higher ISC accumulation at this time point.

Evaluating Recurrence Following Surgery: Comparing Resection Mediated by PA Imaging to Microscopic Surgical Resection A randomized, blinded surgical trial to evaluate recurrence following two surgical methods was performed. Thirty athymic nude female mice were implanted with U251(Luc+) cells in the right dorsal flank. Of these, 24 demonstrating suitable tumor growth were selected and randomized 4 weeks after implantation into two groups (PA-guided surgery arm, N=12; microscopic surgery arm, N=12) in order to closely match tumor sizes between groups. The mean animal weights were 26.2 g (24-30 g) in the PA cohort and 27.5 g (23.1-31.2 g) in the microsurgery cohort. The mean largest dimension in terms of tumor size was 1.1 cm (0.7-1.3 cm) in the PA cohort and 1.0 cm (0.6-1.1 cm) in the microsurgery cohort.

Photoacoustic imaging performed prior to injection (850 nm) showed minimal/no PA signal within tumors. Twenty-four hours after intraorbital injection of ISCs (1 mg/kg based on ICG weight), PA imaging was performed; tumors demonstrated uptake based on PA imaging with excitation set at 850 nm. All animals were injected with ISCs at the same dose. No immediate toxicity was observed during the surgical procedure or in the perioperative period. Surgical resection was performed in both groups by a neurosurgeon under 3.5× magnification with bright white lighting. A combination of forceps and sharp dissection was carried out in order to completely resect the tumors. Where tumors involved the flank musculature, efforts were made to resect the tumor completely from the muscle. After gross tumor resection, the mice in the microscopic surgical resection cohort had their wounds irrigated with 0.9% normal saline. The mice in the PA-guided surgery cohort similarly underwent surgical resection aimed at gross total resection. Following irrigation, however, PA imaging was performed. In 10/12 animals, additional tumor tissue was identified and additional surgery was carried out to completely remove tumor. Resection proceeded until PA average was <50% of pre-operative value at 850 nm and post-resection spectra matched that of background tissue in the flank. For all animals, imaging parameters and time-gain constant were maintained at the same level. Following skin closure, 8/12 animals in the PA-guided surgery cohort and 7/12 animals in the microscopic surgery cohort had seromas noted at the site of surgery. No drains were placed. These seromas were all fluctuant and not solid or nodular in appearance.

Figure 13:
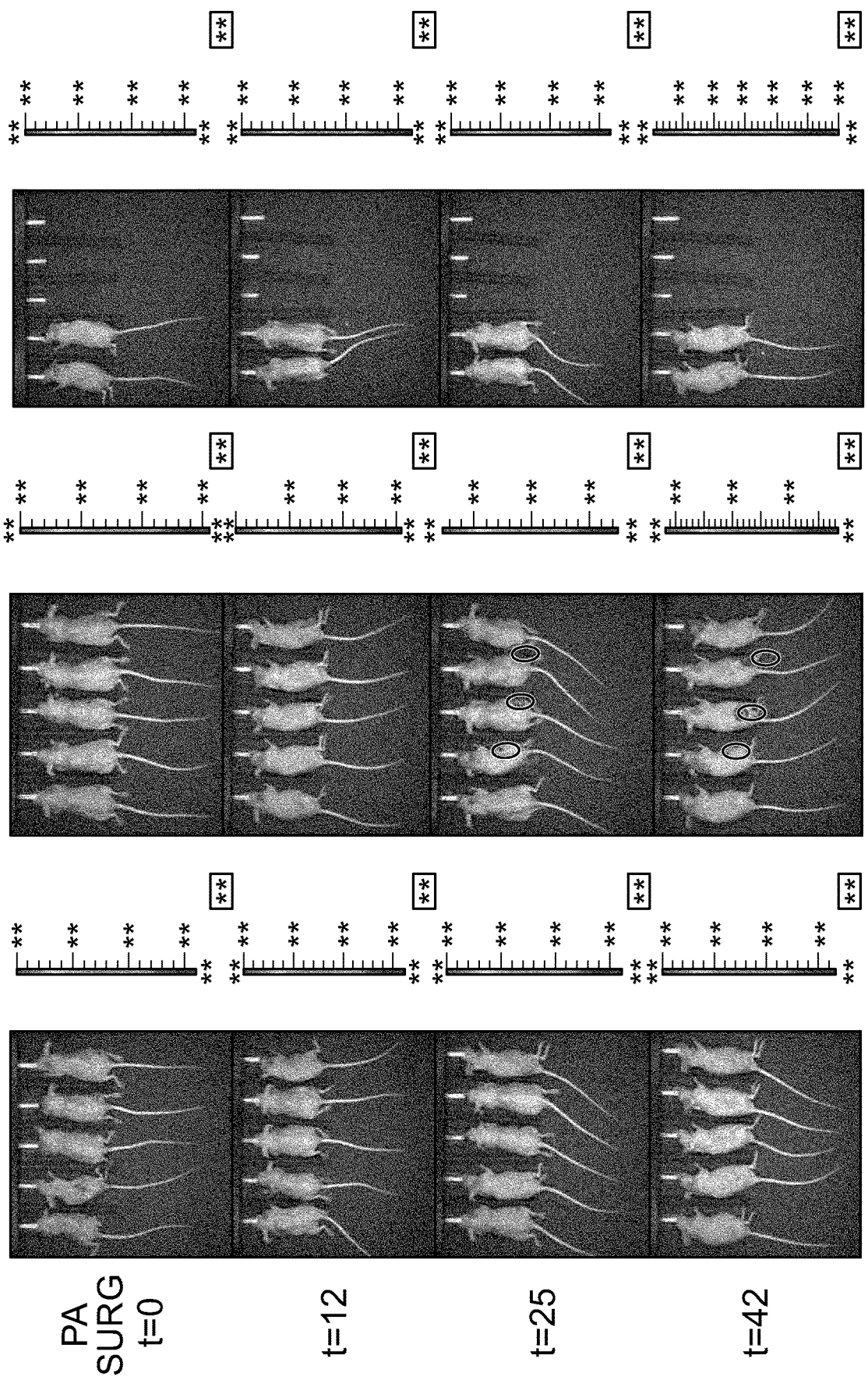
FIG. 13. Photoacoustic (PA)-guided surgery cohort. Twelve animals underwent PA-guided surgery, 24 hours following intraorbital injection of ISCs. Timepoints for intraperitoneal injection of D-Luciferin (to assess recurrence) were at 0, 12, 25, and 42 days. In the PA-guided surgery cohort, 3/12 animals demonstrated recurrence noted at t=25 days, all animals survived. Although post-operative seromas were noted in animals, the presence of tumor was ascertained solely by bioluminescence.
Figure 14:
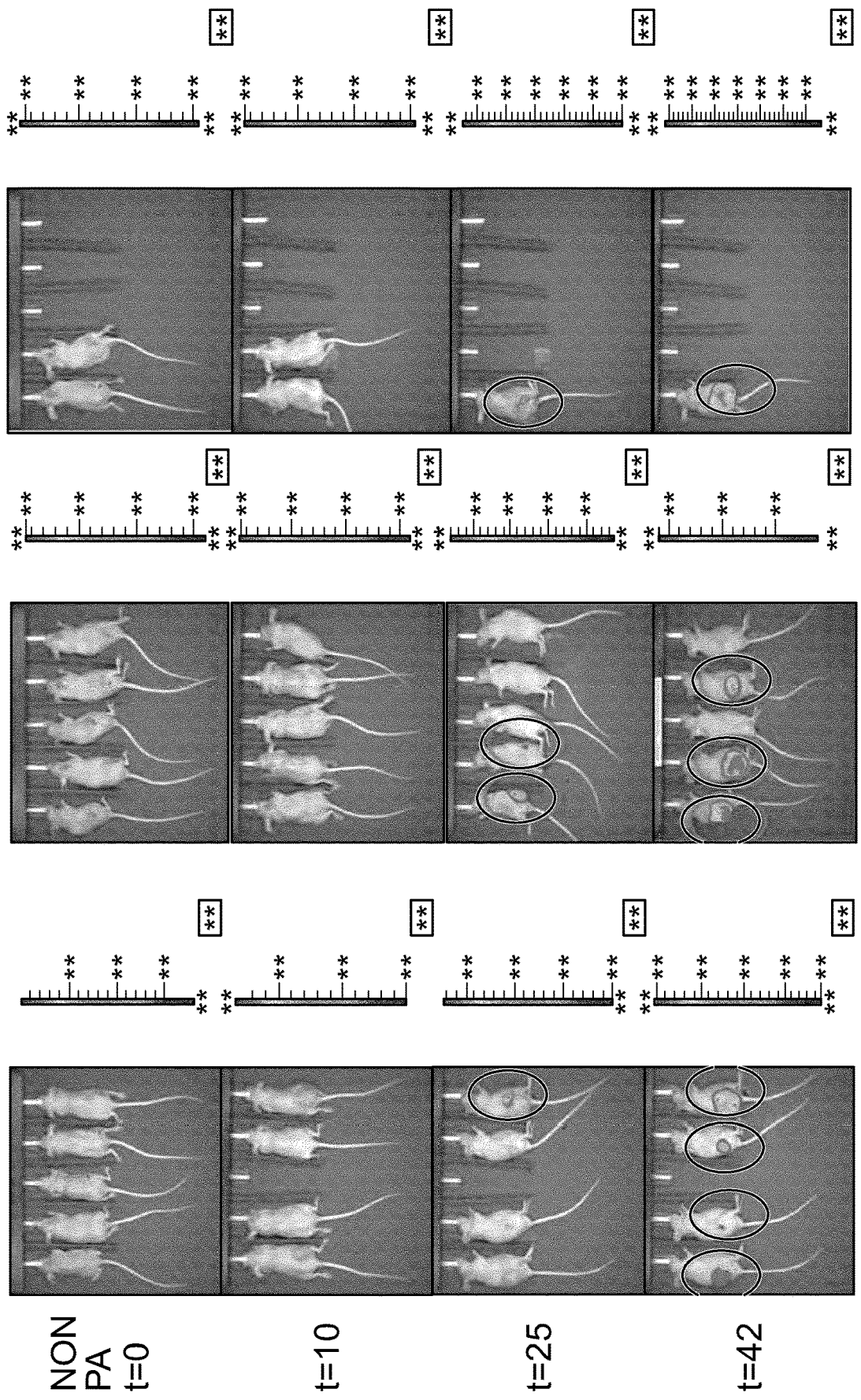
FIG. 14. Microscopic surgery cohort. Twelve animals underwent surgery using 3.5×loupe magnification, 24 hours following intraorbital ISC injection. Timepoints for intraperitoneal injection of D-Luciferin (to assess recurrence) were at 0, 10, 25, and 42 days. In the microscopic surgical resection cohort, 8 animals showed recurrent tumors (first noted at t=25 days) and two animals died (t=10 and t=25). Although post-operative seromas were noted in animals, the presence of tumor was ascertained solely by bioluminescence.

Animals were tagged and identified following the surgical procedure by another individual; injection of D-Luciferin and bioluminescence studies were also carried out blinded to the surgeon. Animals were imaged through bioluminescence imaging at four time points (FIGS. 13 and 14). Recurrence was noted based on the appearance of bioluminescence 12 minutes following injection of D-luciferin for each animal. In the PA-guided surgery cohort, 3/12 animals demonstrated recurrence noted at t=25 days and no additional recurrent tumors were detected through 42 days. All three animals that developed recurrence were from the group that had tissue removed following PA-guided surgery. The two animals that did not have additional tumor identified at the time of PA imaging (following first-stage surgical resection) did not develop recurrent tumor. All animals survived.

In the microscopic surgical resection cohort, 4/12 animals showed recurrent tumors at 25 days and 8/12 animals showed recurrent tumors by 42 days. 2/12 animals died (t=10 and t=25). The PA-guided surgical resection cohort (N=12) demonstrated improved progression-free survival at an endpoint of 42 days as compared to the microscopic surgical resection cohort (N=12) based on the log-rank test (p=0.0053) (FIG. 11B).

In conclusion, the inventors of this application developed a contrast agent comprised entirely of FDA-approved components that is detectable by MR and PA imaging in real-time. ICG SPIO clusters are stable in in vitro and in physiologic conditions, can be taken up within tumors by EPR, and are detectable in a preclinical animal model 24 hours following injection. In a surgical resection model following injection of ISCs, animals undergoing PA-guided surgery demonstrated increased progression-free survival compared to animals undergoing microscopic surgery. Further work can incorporate ISCs into cell-specific technologies and can contribute to wider usage of photoacoustic imaging in surgery.

Example 3

Image-Guided Resection and Local Treatment of Glioblastoma

Synthesizing and Characterizing the Physical-Chemical Properties of IPS Nanoclusters Preparation of IPS nanoclusters: 7 nm SPIONs can be synthesized by thermal decomposition as known in the art. To prepare IPS nanoclusters, SPIONs (in toluene) ICG (in DMSO) and either PpIX or chlorin e6 (in DMSO) can be mixed at varying ratios, so that a formulation with well-aligned imaging and therapeutic capabilities can be identified. The SPION, ICG, photosensitizer mixture can be added to water and sonicated. The sample can be left open to air overnight, allowing for the slow evaporation of toluene and formation of stable nanoclusters. IPS nanoclusters can be further purified by dialysis or diafiltration. We have previously performed magnetic purification (Miltenyi Biotec) as part of the purification procedure, but found it to be unnecessary. Preliminary studies have revealed that IPS nanoclusters can easily be prepared with both PpIX and Chlorin e6 in high yields and with low polydispersity (PDI<0.15), with a mean hydrodynamic diameter of <80 nm (FIG. 17).

Our preliminary PDT studies have been performed with PpIX; however, chlorin e6 can also be used since it possesses a higher peak extinction coefficient (55,000 at 667 nm vs. 5,186 at 631 nm) and higher singlet oxygen quantum yield (0.75 vs. 0.54). Therefore, chlorin e6 can exhibit >10× higher phototoxicity than PpIX. To improve the sensitivity and accuracy of measuring the clearance and biodistribution of IPS nanoclusters, trace levels of gadolinium can be incorporated into SPION for all pharmacokinetic studies, to allow for tracking via ICP-OES.

Physical-Chemical Characterization of SPIONs and IPS nanoclusters: The size of individual SPIONs and IPS nanoclusters can be determined by transmission electron microscopy (TEM) using a JOEL 1010 operating at 200 kV. The hydrodynamic diameter and surface charge of all nanoclusters can be measured by dynamic light scattering using a Zetasizer Nano zs (Malvern). The longitudinal (r1) and transverse (r2) relaxivity of each nanocluster can be calculated as the slope of the curves 1/T1 and 1/T2 versus Fe concentration, respectively.

T1 and T2 relaxation times can be determined using a Bruker mq60 MR relaxometer operating at 1.41 T (60 MHz). Preliminary studies have indicated that IPS nanoclusters possess an r2 value of 307 $mM^{-1} s^{-1}$. T1 and T2* maps can also be acquired on a 4.7T MR system (higher magnetic strength used for high resolution rabbit brain imaging), interfaced with a Varian DirectDrive console.

The number of IPS nanoclusters in stock samples can be calculated by using Einstein's viscosity equation to determine the volume fraction of the nanoclusters and DLS measurements to determine the average volume of individual nanoclusters. ICP-OES can be used to determine the amount of iron in each sample, as known in the art. Combined, the above measurements can allow us to determine the number of iron atoms (and SPIONs) per nanocluster. Quantification of nanocluster concentration within a given sample can also be performed by measuring iron concentration via ICP-OES and the average number of SPIONs (and thus Fe) per nanocluster by TEM.

The amount of ICG and photosensitizer in each sample can be determined spectrophotometrically. Measurements of nanocluster concentration can be used to determine the amount of ICG and photosensitizer per nanocluster. Nanoclusters can also be dried and weighed to determine the w/w fraction of ICG and photosensitizer.

Characterization of photophysical properties: The optical properties of all nanocluster samples (UV-Vis absorption spectrum and excitation/emission spectrum) can be evaluated as a function of nanocluster/ICG/photosensitizer concentration using a Varian Cary 100 UV-Vis Spectrophotometer and Spex Fluoromax-3 spectrofluorometer, respectively. The photoacoustic properties can be evaluated on a Vevo LAZR scanner using a homemade phantom device (FIG. 1E).

Measurements can be compared to free ICG and photosensitizer at equivalent concentrations. Furthermore, various nanocluster samples can be compared in their ability to form singlet oxygen. This can be measured using a comparative method and the 102 quantum yield can be calculated by comparison with a standard photosensitizer. Illumination can be performed at a wavelength that is specific to the absorption peak of the photosensitizer using one of several diode lasers (632 nm for PpIX and 665 nm for chlorin e6).

Determination of nanocluster stability: The dissociation of ICG and photosensitizer from the IPS nanoclusters can be assessed by incubating the nanoclusters in saline or serum at pH 7.4 or pH 5.0 for various periods of time, up to 1 month. The nanoclusters can be separated from free dye at each time point via magnetic purification (Miltenyi Biotec). The ratio of ICG and photosensitizer to Fe can then be calculated and plotted as a function of time. In addition, measurements of the hydrodynamic diameter, size of the nanocluster, and the size of individual SPIONs within the nanocluster can be determined by DLS and TEM, respectively, at each time point. The relaxivity of the nanoclusters can also be assessed.

Statistics: Statistical significance between groups/time points will be determined by analysis of variance (ANOVA) or a Student's t-test where appropriate. A $p<0.05$ can be considered statistically significant.

Evaluating the Therapeutic Potential of IPS Nanoclusters In Vitro

In Vitro Assays for PDT-mediated cytotoxicity: The cytotoxicity of the various IPS nanocluster formulations can be assessed by MTT, trypan blue exclusion, clonogenic, and the HepG2 Hepatocarcinoma Homogeneous Apoptosis Assay (per guidelines of the ISO 10993-5 Biological evaluation of medical devices: Part 5 Tests for in vitro cytotoxicity). Time course (up to 48 h) of various concentrations of each nanocluster formulation (up to 1 mg/mL Fe) can be incubated with rabbit cancer cells (VX2). Analogous studies can be performed with matching concentrations of ICG and photosensitizer, individually and in combination.

After predetermined incubation periods, cells can be rinsed of nanoclusters/ICG/photosensitizer, provided with fresh media and then illuminated. Illumination can be performed at a wavelength that is specific to the absorption peak of the photosensitizer (632 nm for PpIX and 665 nm for chlorin e6) and/or 808 nm for ICG. Light doses up to 10 $J/cm^2$ can be tested for PDT and light doses up to 600 $J/cm^2$ for PTT. Both the fluence rate and the exposure time can be varied. The time at which the cells are illuminated after incubation with nanoclusters can also be varied, as well as the time between PDT and PTT, for studies where combination therapy is applied. Analogous experiments can be performed in the absence of light-activation. Parallel dishes of nanoclusters/ICG/photosensitizer-exposed cells can be imaged by confocal microscopy to evaluate uptake and subcellular distribution. In particular, one can study the time course of photosensitizer/ICG localization to the cell surface (membrane bound) and its internalization. These studies will inform interpretation of cytotoxicity data relative to measured levels of total drug uptake. For example, poorer cytotoxicity in the presence of equivalent bulk levels of nanoclusters may be a function of differences in the time course of photosensitizer and/or ICG localization. PDT generally leads to damage of the organelle/surface at which the photosensitizer is localized due to the limited diffusion distance of singlet oxygen. For all cellular assays, dose response curves and $EC_{50}$ values can be determined using four-parameter curve fitting. An optimal IPS nanocluster formulation can be identified based on potency (i.e. low $EC_{50}$) as well as alignment between therapeutic and photoacoustic and MR imaging properties/sensitivity. This optimal IPS nanocluster formulation can be used for all animal studies.

Once an optimal IPS nanocluster formulation has been identified, additional in vitro cytotoxicity studies (with and without PDT/PTT) can also be performed, with mouse (GL26 and GL267) GBM cells, normal mouse astrocytes, human GBM cells (U251), Hep G2 polarized human hepatocytes, human umbilical vein endothelial cells (HUVECs), normal human astrocytes (NHAs) and glioma stem cells (kindly provided by Jeremy Rich, Cleveland Clinic).

Statistics: Statistical significance between groups/time points will be determined by ANOVA or a Student's t test where appropriate. A $p<0.05$ can be considered statistically significant.

The nanoclusters are unlikely to be cytotoxic (without illumination), since no components alone are cytotoxic. Moreover, we have already demonstrated that neither ICG-coated SPION nor PpIX-coated SPION nanoclusters are cytotoxic; however, toxicity may result from nanocluster aggregation or impurities that are not removed following synthesis. As such, the nanoclusters can be further purified by extended dialysis or diafiltration to remove small contaminants and 0.2 μm filtered to remove large aggregates. Additional options for purification included graded centrifugation, magnetic purification (Miltenyi Biotec), or size exclusion chromatography.

We have already demonstrated that PTT with ICG-coated nanoclusters results in a higher cytotoxicity compared with free ICG (FIG. 16). We have also found that PDT with PpIX-coated nanoclusters exhibit a higher phototoxicity compared with free PpIX. Therefore, similar results can be obtained when ICG and the photosensitizers are combined into a single nanocluster. Nonetheless, if the $EC_{50}$ worsens when ICG and the photosensitizer are formulated into a single IPS nanocluster, perhaps because of energy transfer, one can consider using mixtures of ICG-coated and photosensitizer-coated nanoclusters. If the combination of PDT+PTT do not produce a synergistic cytotoxic effect, one can explore a wider range of exposure times and times between washing of cells, PDT, and PTT. One can also test whether there is a synergistic effect when mixtures of ICG-coated and PpIX-coated nanoclusters are used. This latter approach can also allow us to vary the incubation time of each formulation. If a synergistic effect still cannot be achieved, one can move forward with an ICG-only nanocluster (i.e. no photosensitizer) that exhibits the lowest $EC_{50}$, with well-aligned photoacoustic and MR imaging properties and will utilize only PTT for treatment. Notably, significantly better tissue penetration can be obtained with PTT than PDT, due to the significant red-shift in the peak absorbance of ICG compared with the photosensitizers.

Evaluating the Pharmacokinetics, Contrast Enhancement, and Ability of IPS Nanoclusters to Enhance Intraoperative Photoacoustic-Guided Resection and Local Treatment in a Rabbit Model of GBM.

Brain tumor model: One can work with New Zealand White rabbits with intracranially-induced VX2 carcinoma. Although for cost reasons, this limits the number of animals and studies that can be performed, this model provides tumors of reasonable size (5-8 mm) for image-guided resection, and is much simpler to work with than intracranial rat tumor models for this application. Moreover, this rabbit model has been previously validated as an imageable surgical resection model of GBM. No glial tumor model is available in the rabbit. However, VX2 tumors exhibit various attributes of primary brain tumors, such as microinvasion, pseudopalisading, and growth along blood vessels and in perivascular spaces, causing breakdown of the blood brain barrier (BBB) within the tumor and in brain adjacent to the tumor.

Prior to implantation, the VX2 cells can be engineered to express enhanced green fluorescent protein (GFP) to allow these cells to be easily distinguished from host cells. It has previously been shown that GFP expression in VX2 cells has no detectable effects on cancer cell morphology, tumor size, or rabbit survival rate. Tumors can be induced in an equal number of male and female New Zealand White rabbits (3.3-3.8 kg, Charles River). A burr hole can be drilled 5 mm posterior to the sagittal suture and 5 mm left of the midline. $2\times10^5$ VX2 cells can be injected 2 mm below the dura and allowed to grow for 7 days, which is expected to result in tumors 5-8 mm in size.

Clearance and biodistribution of IPS nanoclusters: To measure the rate of blood clearance and biodistribution of IPS nanoclusters, tumor-bearing New Zealand White rabbits (n=18) can be bled and sacrificed at various times after the injection of the IPS nanoparticles (10 mg Fe/kg). All animals can be intravenously injected with IPS nanoclusters (10 mg Fe/kg) 7 days after the intracranial injection of VX2 cells. Notably, SPION doses of 1.1 mg Fe/kg in humans and 10-15 mg/kg in rats have previously been used successfully to aid in brain tumor visualization by MRI. Six rabbits can be bled at 30 min and 6 hr, six can be bled at 1 hr and 12 hr, and six can be bled at 6 hr and 24 hr. The rabbits can be sacrificed at 24 hr, 48 hr, and 1 week (6 per time point), blood can be collected, and the lungs, heart, brain, tumor, kidneys, bladder, spleen, and liver can be harvested and fractionated for fluorescent imaging, ICP-OES and histopathological analysis. Fluorescent images of the organs and blood samples can be acquired using a Perkin Elmer IVIS, to monitor the pharmacokinetics of ICG and photosensitizer. For these studies, the tissues can be digested and the nanoclusters can be dissolved in DMSO, to eliminate self-quenching and SPION-mediated quenching. Intensities can be compared to ICG and photosensitizer standards. For all pharmacokinetic studies, one can incorporate trace levels of gadolinium into SPION to also allow for sensitive (background free) quantification of SPION pharmacokinetics by ICP-OES. Additional time points can be evaluated to measure clearance, as necessary. For comparison, blood and tissues can also be collected from tumor bearing rabbits injected with saline and sacrificed at 24 hr post-injection (n=6). All biodistribution measurements will be reported as % injected dose per gram tissue (% ID/g). If biodistribution analysis reveals SPION, ICG, and/or PpIX concentrations within tumors that are expected to be too low for imaging and/or therapy, dosing can be adjusted in subsequent studies, as deemed appropriate.

Toxicological analysis of IPS nanoclusters: After administration of IPS nanoclusters, animals can be examined regularly for survival and evident behavioral or motor impairments. Rabbits can also be weighed regularly. Blood and histopathological analyses can be performed on the rabbits that were sacrificed at 24 hours, 48 hours, and 1 week post-injection by the UPenn School of Veterinary Medicine Comparative Pathology Core. Hematology analyses of blood collected at time of sacrifice may include hematocrit, hemoglobin, MCV, white blood cell and differential counts. Additional analyses may include BUN, creatinine, total protein, albumin, globin, and liver function tests. Histopathological analysis including hematoxilin/eosin staining of the brain, kidney, liver, spleen, and lungs can be performed to assess for potential effects of IPS nanoclusters on organ morphology and function.

Comparative analysis of photoacoustic and MR images: New Zealand White rabbits (n=6) can be intravenously injected with IPS nanoclusters (10 mg Fe/kg) 7 days after the intracranial injection of VX2 cells. All animals can be imaged by MR (described below) immediately before and 24 hours after injection of the IPS nanoclusters. A craniotomy can then be performed, the bone flap removed, and the tumor visualized by photoacoustic imaging. The rabbits can then be sacrificed and the brains can be harvested. Non-fixed frozen tumors can be cryo-sectioned and images of tumor and surrounding brain tissue in both the GFP and ICG channels can be acquired, using a fluorescent microscope Images can be subsequently stained with H&E and DAB-amplified Prussian Blue and examined with white light microscopy.

PA images, MR images and histology slices can be spatially aligned, for qualitative comparison of tumor morphology. In addition, the signal intensity within the PA images can be compared with the relative signal intensity (rSI) within MR images as well as the calculated iron concentration, as determined from 72 maps.

Methods for MR image analysis are described below. For the PA images, the mean signal intensity can be acquired within a region of interest (ROI) within the tumor. A linear regression analysis can be used to compare the various measurements and the p-value and R2 values can be determined. A $p<0.05$ can be considered statistically significant.

Accuracy of determining tumor margin via IPS nanoclusters: The accuracy of determining the tumor margin with IPS nanoclusters can be quantified by analyzing the fluorescent images of GFP and ICG, as known in the art. Briefly, a region of interest (ROI) can be selected within the tumor and within normal brain tissue, so that a threshold value can be established that allows for the differentiation between the tumor and normal tissue. This can be done separately for GFP and ICG. The threshold value canbe set to 'B+0.5 (T-B)', where B is the average pixel intensity of the background and T is the average pixel intensity within the tumor. An automated growing ROI algorithm can be used to identify the tumor boundary in both the GFP and ICG images.

To quantify how accurately the IPS nanoclusters can identify the tumor margin, for every point along the tumor margin in the GFP image, a line can be drawn to the nearest point along the margin on the corresponding ICG image. These values can be plotted on a histogram (frequency vs. distance between GFP and ICG tumor margins) and fitted to a Gaussian to identify the mean over-/under-estimation, the standard deviation, and standard error of the mean. This analysis may also allow for identification of maximum over- and underestimation of the tumor margin with IPS nanoclusters. Note, all fluorescent images can be corrected for spectral shift, prior to conducting this analysis. A similar approach can also be taken to compare GFP and ICG images within Prussian blue images.

In vivo MR imaging of IPS nanoclusters following intravenous injection: T2-weighted MR images can be acquired before and 24-hours after the intravenous injection of IPS nanoclusters (10 mg Fe/kg). The MR imaging protocol can consist of a gradient echo multi-slice (GEMS) imaging sequence (repetition time, TR=200 msec; echo time, TE=5 msec; number of excitations, NEX=8; field of view, FOV=4 cm, with a resolution of 256×256). In an attempt to provide a more quantitative measure of SPION-enhancement, one can also acquire T2* and T2 maps. Specifically, for T2* maps the MR imaging protocol may consist of a GEMS imaging sequence with multiple echoes (TR=200, TE=3, 6, 9, 12 ms). For T2 maps, the MR imaging protocol may consist of a spin echo pulse sequence with multiple echoes (TR=3000, TE=5, 15, 30, 45, 60, 75, 90, 105, and 120 ms). Imaging parameters can be adjusted as deemed necessary; however, we have previously found these parameters to be appropriate for the imaging of SPIONs on this system. To compare SPION-based tumor enhancement to the clinical standard of gadolinium (Gd) enhancement, pre and post-Gd (0.1 mmol Gd/kg intravenous) T1-weighted images can be obtained before nanocluster administration. T1-weighted imaging may consist of spin echo multi-slice images (TR=1000, TE=15 sec).

MR image analysis: All images can be converted to a lossless image format using ImageJ. T2 and T2* images can be evaluated using the open source DICOM viewer OsiriX. Relative signal intensity (rSI) can be measured within an operator-defined region of interest (ROI) within each tumor before and after SPION administration and normalized to surrounding brain. The signal change can then be determined by calculating the rSI ratio, defined as the quotient of the rSI in the pre- and post-SPION MRI images. The Wilcoxon signed-rank test can be used to compare the rSI ratios of each group of animals. A $p<0.05$ can be considered statistically significant. For quantitative analysis, T2 and T2* maps can be generated using the OsiriX T2 Fit Map plug-in, after inputting the echo times. Mean relaxation time within tumor and background brain ROIs can be recorded.

The effect of SPIO-based contrast agents on magnetic resonance relaxation rates (R2=1/T2) is typically governed by the relation: $R2=R2,0+r2C$ where $R2,0$ is the relaxation rate in the absence of contrast agent, C is the concentration of the agent and r2 is a constant for a given agent known as the relaxivity. The relaxivity of the contrast agent can be measured separately using phantom experiments with varying concentrations of the contrast agent. Relaxivity can be measured using the measured relaxation rates (R2=1/T2) as a function of iron concentration. For comparison of SPION-enhanced and gadolinium-enhanced tumor volumes, T1, T2 and T2* images can be segmented with ITK-SNAP open source segmentation software using a semi-automated combination of classification-based segmentation and region growing. The average difference in volume can be calculated and compared across each group of animals.

Figure 19:
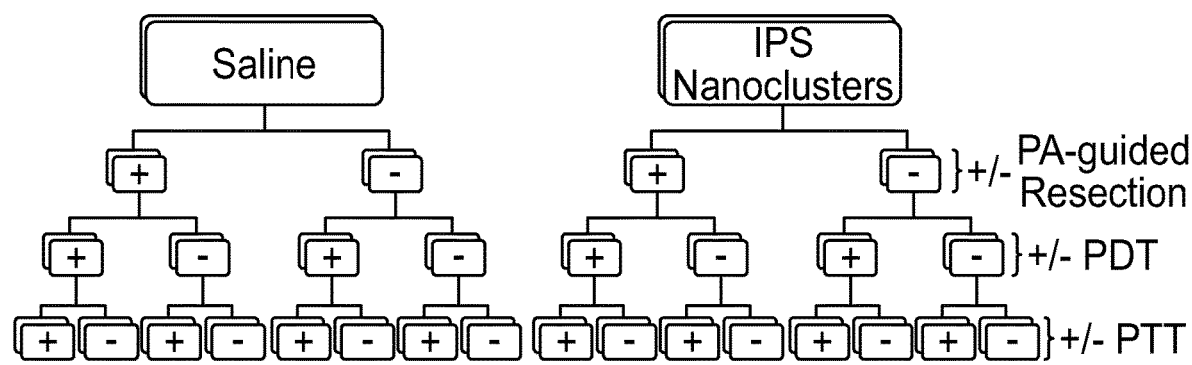
FIG. 19. Outline of animals (16 groups) used to evaluate the therapeutic efficacy of IPS nanoclusters. Each group consists of 10 animals (5 male, 5 female). Groups are subject to resection, PDT, and/or PTT. Control groups can receive saline, in place of the IPS nanoclusters.

Evaluation of therapeutic efficacy: New Zealand White rabbits (16 groups, n=10 per group) can be intravenously injected with IPS nanoclusters (10 mg Fe/kg) or saline 7 days after the intracranial injection of VX2 cells. Twenty-four hours later, the animals can be subjected to various permutations of resection, PDT, and/or PTT. A summary of the groups is provided in FIG. 19. All animals can be imaged by MR (described above) prior to the injection of IPS nanocluster on day 7. The imaging protocol on day 7 may consist of both pre-contrast and Gd-enhanced imaging. This can allow SPION-based tumor enhancement to be compared with the clinical standard of Gd-enhancement. Following MR imaging, the IPS nanoclusters can be administered and the animals can be imaged again 24 hrs later (day 8), i.e. SPION-enhanced imaging. A craniotomy can then be performed, the bone flap removed, the dura cut and subsequently the tumor can be located with an operating microscope under white light illumination and, depending on the group, not resected or resected under white light illumination, followed by removal of any residual tumor tissue under PA-guidance. The surgeon can be blinded to whether or not the animal received IPS nanoclusters, to minimize surgical bias. The resected tissue can be evaluated by immunohistochemistry, as described below. For some groups, the resection cavity or whole tumor can be subjected to PDT and/or PTT. PDT can be of the surgically-exposed tumor using a microlens-tipped fiber. PDT can be performed with a 632 nm or 655 nm laser, for PpIX and Chlorin e6, respectively, at a fluence of 50 J/cm$^2$. PTT can be performed with an 808 nm laser and a fluence of 250 J/cm$^2$. The timing between PDT and PTT can be based on findings, to the extent that is possible (i.e. ensuring a reasonable surgical timeframe). Animals that did not receive IPS nanoclusters can still be subjected to PDT and PTT illumination, as indicated in FIG. 19. Notably, although IPS nanocluster dose, timing of surgery after injection of IPS nanoclusters, PDT fluence and PTT fluence were derived from prior experience and are consistent with typical values reported in the literature, the final selected doses and timing of surgery can also be guided by in vitro cytotoxicity studies as well as biodistribution studies.

Following surgery, rabbits can be evaluated at least daily for weight, activity, well-being, signs of neurological deficit, and survival (out to 45 days). Rabbits can be sacrificed upon first signs of neurological deficit, which is expected to manifest as a pronounced head tilt. At time of sacrifice, tumors can be excised and pathologically examined (described below). A log-rank analysis can be performed on data in Kaplan-Meier curves to identify statistical significance ($p<0.05$) between groups.

Immunohistochemistry: The weight and volume of resected tissue specimens and whole brains, acquired at time of sacrifice, can be recorded. The tissues can be embedded in OCT, frozen on dry ice/butane, and stored at ~80° C. Frozen sections can be cryostat-cut, counterstained with hematoxylin, dehydrated through graded ethanol and xylene, dried, and mounted on glass coverslips. The SPIONs can be visualized by DAB-amplified Prussian blue staining. Images can be acquired using an Axioskope40 (Zeiss) Immunostaining can be performed to identify GFP expression in cancer cells. The area of staining as a percentage of total area can be calculated using five representative view fields. Fluorometric TUNEL staining can be performed to investigate the presence of PDT/PTT induced apoptotic cells. In brains with non-resected tumors, this can also give an indication of the depth at which these therapies are effective.

Statistics: Statistical significance between groups/time points can be determined by analysis of variance (ANOVA) or a Student's t-test where appropriate. A $p<0.05$ can be considered statistically significant.

Figure 20:
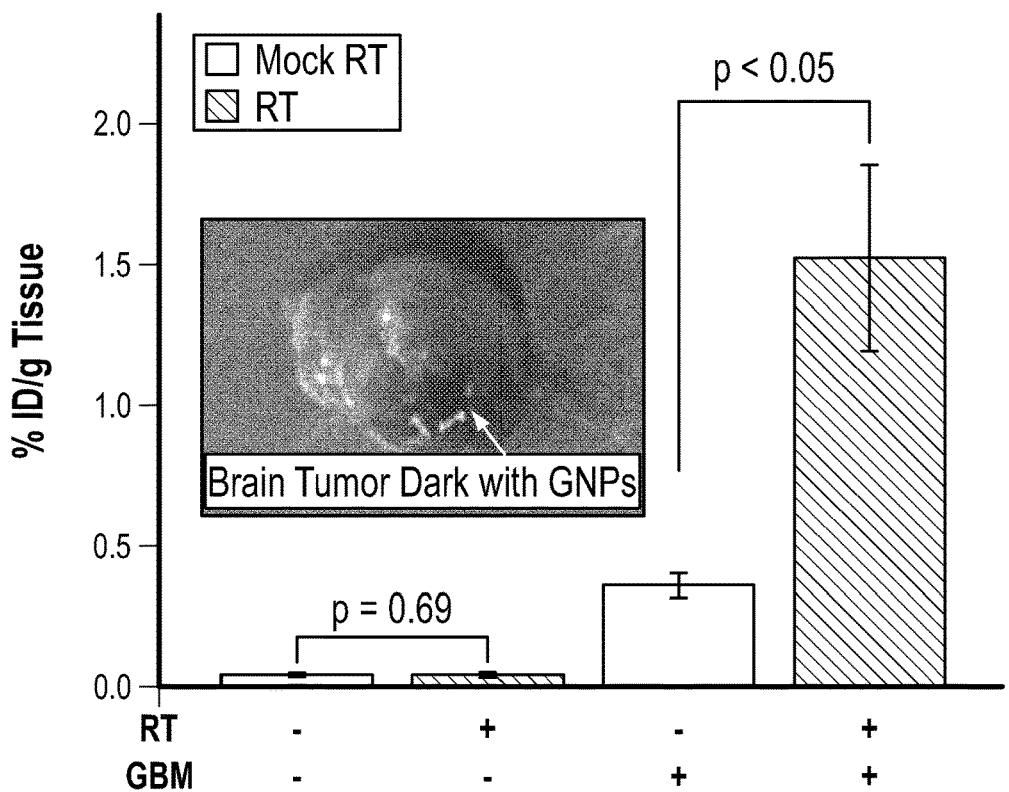
FIG. 20. ICP-MS analysis of gold uptake in healthy brains and those with orthotopic GBM, 48 hours after i.v. injection of saline or AuNPs at 0.4 g Au/kg. AuNPs were administered 7-14 days after 20 Gy RT or mock-irradiation. Inset: Representative orthotopic U251 tumor in mouse brain harvested 48 hr after GNP administration.

If IPS nanoclusters are found to be highly toxic to healthy organs, one can try a low dose, an alternative formulation (e.g. different ratio between ICG, SPION, and photosensitizer), a different photosensitizer (PpIX or chlorin e6), or IPS nanoclusters of a different size. If there is a disagreement between MR and PA images, it will likely be due to poor sensitivity in one of the imaging modalities or because of dissociation of ICG from the nanoclusters in serum. These shortcomings can be overcome by injecting a higher dose and/or adjusting the ratio of ICG-to-SPION. If the IPS nanoclusters prove to be inaccurate in identifying tumor margins, this may be due insufficient accumulation of IPS nanoclusters within the tumor. Initially one can attempt to overcome this limitation by increasing the total injected dose of IPS nanoclusters. As a second option, one can attempt to utilize IPS nanoclusters with smaller hydrodynamic diameters, to improve tissue penetration. If these simple measures fail, one can explore the use of matrix-modifying enzymes (e.g. collagenase, hyaluronidase) to enhance IPS nanocluster delivery. We and others have shown that matrix-modifying enzymes can be used to significantly improve the overall accumulation of nanoparticles in tumors. If it is found that sub-regions of brain tumor are devoid of IPS nanoclusters due to an intact and robust BBB, one can explore the possibility of adding specificity for the transferrin receptor (TfR) to the IPS nanocluster. It has previously been reported that targeting the TfR can improve the delivery of nanoparticles into the brain. Lastly, one can consider using radiation therapy to increase the permeability of the BBB. We have previously shown that there is significant increase in the total uptake of nanoparticles in brain tumors following irradiation (FIG. 20). This option will only be pursued after all of the other options noted above have been ruled out, since this approach is not aligned with the current standard of care, whereby surgical resection precedes radiation therapy. It should be noted that we have already demonstrated that we can use SPION-loaded micelles to visualize orthotopic GBMs in mice. Moreover, SPION have also previously been used successfully to aid in brain tumor visualization by MRI in humans; therefore, a similar level of success can be achieved with rabbits.

Figure 21:
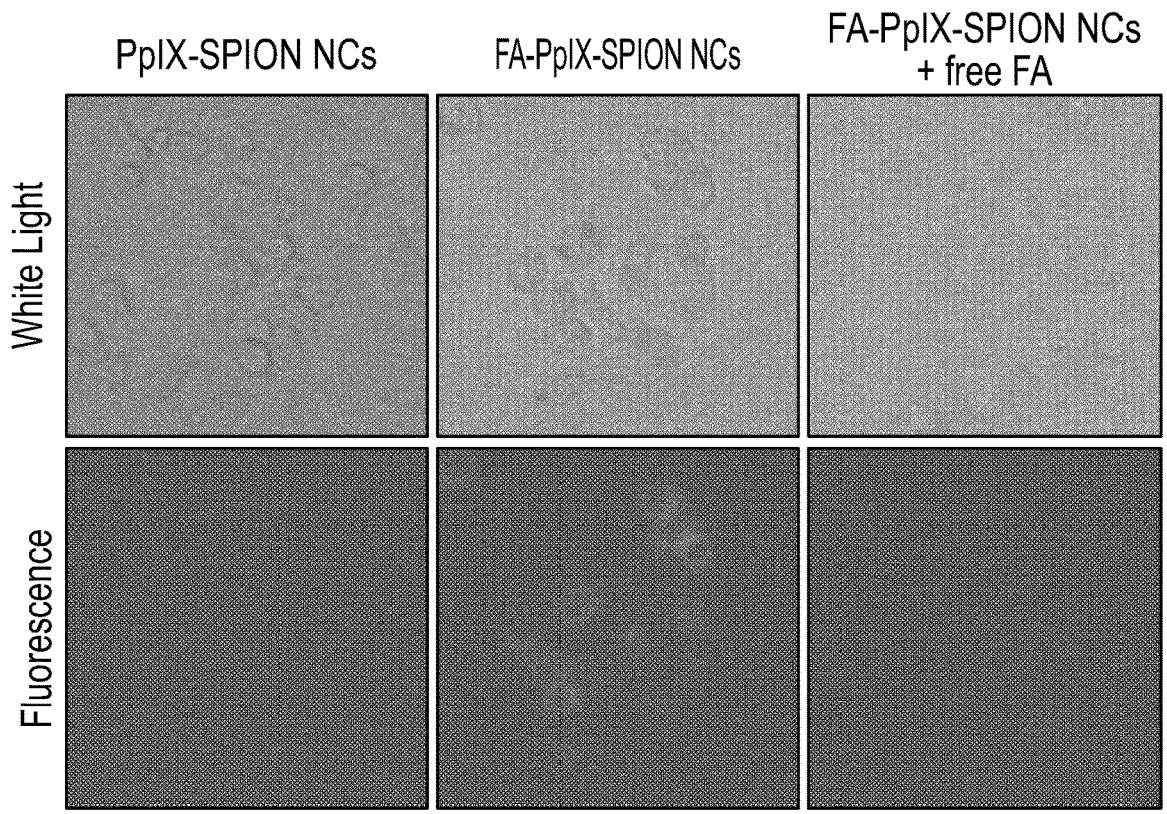
FIG. 21. PpIX-loaded SPION nanoclusters (NCs) were functionalized with folic acid (FA) and incubated with folate receptor-positive KB cells (middle column). Cell labeling led to a significant increase in cellular fluorescence. To confirm specificity, a competitive inhibition study was performed with free FA, which led to a statistically significant reduction in fluorescence (right column). Non-targeted PpIX-loaded SPION NCs did not bind to KB cells (left column).

If tumor specificity is deemed to be poor, one can try adding GBM specific targeting ligands to the IPS nanoclusters. Moreover, we have developed a proprietary method to functionalize the surface of IPS nanoclusters with targeting ligands and have confirmed specific binding of these targeting ligands (FIG. 21). If it is found that it is necessary to improve specificity, EGFR represents a reasonable target option, since it is overexpressed on 54% of GBMs, but not low grade gliomas.

If PDT does not lead to a clear improvement in median and/or overall survival when compared with and/or added to PTT, it may be the result of inadequate tissue penetration of light used for PDT. If this is the case, one can consider evaluating ICG-only nanoparticles, for image-guided resection and PTT. The peak excitation wavelength of ICG is red-shifted compared with most photosensitizers, including PpIX and Chlorin e6, and can be excited at depths greater than 1 cm in the human brain.

If the sensitivity of detecting GFP is too low to get confident measurements of tumor margin on tissue sections, one can use immunofluorescence to detect GFP. If PA-guided resection does not lead to an improvement in survival, higher nanocluster doses can be used. One could also test the prospect of using ICG fluorescence or absorbance, as alternative methods of detection. If PDT and PTT do not improve survival, again this problem may be rectified by utilizing a higher dose, an alternative IPS nanocluster formulation, a different photosensitizer, or nanoclusters with a different hydrodynamic diameter.

Example 4

Chlorin e6-Coated Superparamagnetic Iron Oxide Nanoparticle (SPION) Nanoclusters as a Theranostic Agent for Dual-Mode Imaging and Photodynamic Therapy In this study, the inventors demonstrate that Ce6 can also be used to solubilize nanoclusters of SPIONs without using any extra carrier or complicated chemical reaction. Ce6 is structurally similar to PpIX, but possesses a higher peak extinction coefficient (55,000 at 667 nm vs. 5,186 at 631 nm), has a 46 nm red-shifted peak absorbance, and higher singlet oxygen quantum yield (0.75 vs. 0.54). The physical-chemical properties of the Ce6-SPION clusters (Ce6-SCs) were systematically evaluated. The Ce6-SCs were further tested for their ability to serve as magnetic resonance and fluorescence contrast agent as well as a PS for PDT in a murine tumor model.

Materials and Methods

Materials.

Chlorin e6 (Ce6, MW=596.68) was purchased from Santa Cruz Biotechnology, iron (III) acetylacetonate, 1,2-hexadecanediol, benzyl ether, oleylamine, and anhydrous dimethyl sulfoxide (DMSO) were obtained from Aldrich. Oleic acid was purchased from Chem-Impex International, Inc. Ethanol was purchased from Decon Labs, Inc. All other chemicals and solvents were of analytical grade and were used without further purification. All the buffer solutions were prepared with deionized water.

Synthesis of SPIONs.

SPIONs were synthesized according to thermal decomposition method as previously described.[36] Briefly, iron(III) acetylacetonate [Fe(acac)$_3$] (2 mmol), 1,2-hexadecanediol (5 mmol), oleic acid (2 mmol), and oleylamine (6 mmol) were added, to benzyl ether (20 mL) in a two-necked round-bottomed flask, equipped with a reflux condenser and stir bar. The mixture was heated to 200° C. for 15 min, and then the temperature of the mixture was maintained at 300° C. for 1 h under nitrogen with vigorous stirring. At the end of this period, the mixture was left to cool down to room temperature, two volumes of ethanol were added, and the resulting mixture was centrifuged (5500×g for 15 min) to precipitate the nanoparticles. The particles were then allowed to air dry and dissolved in toluene. Large aggregates were removed by centrifugation at 3000×g for 15 min.

Preparation of Ce6-SCs.

A mixture (200 μL) containing Ce6 (2 mg into dimethyl sulfoxide (DMSO)) and SPION (1, 2, 4, 5, or 6 mg based on the Fe concentration in toluene) was pipetted into a glass vial containing 4 mL of water, and the sample was sonicated until a homogeneous solution was observed. The toluene was evaporated overnight. Dialysis was performed with dialysis tubing (3500 MWCO, Fisherbrand) into 4 L of water to remove dimethyl sulfoxide. The Ce6-SCs were further purified by MACS (25 LD columns, Miltenyi Biotec, Germany) column.

Characterization of Ce6-SCs.

The diameter and size distributions of the Ce6-SCs were measured with dynamic light scattering (DLS, Malvern, Zetasizer, Nano-ZS). The morphology of the nanoparticles was observed using a transmission electron microscope (TEM) (JOEL 1010). T2 relaxation times were measured using a benchtop relaxometer (Bruker, mq60 NMR analyzer). The encapsulation efficiency and payload of Ce6 was determined using UV-Vis spectrophotometer (Varian, 100 Bio). The concentration of the coated Ce6 was quantified by dissolving the Ce6-SCs in DMSO, measuring the absorbance at 404 nm and comparing the reading to a standard concentration curve of free Ce6 in DMSO. Iron concentration was quantified by plasma optical emission spectroscopy (ICP-OES) (Spectro Genesis, GMBH).

Ce6-SCs Release and Stability Studies.

The amount of Ce6 adsorbed on Ce6-SCs, size stability and magnetic properties ($T_2$ mode) in water/fetal bovine serum (FBS) (1/10, v/v) solution were determined as previously reported[36]. Briefly, prepared Ce6-SCs were incubated in water as well as in FBS at 37° C. for the stability study. DLS was used to monitor the particle size for 6 days. Aliquots taken from the sample were tested at various time points for the determination magnetic properties via $T_2$.

To investigate in vitro release behavior of Ce6 from the nanocluster, 1 ml Ce6-SCs solution was placed in a tube containing 9 ml FBS and incubated at 37° C. under continuous shaking. At specific time intervals within two days, 0.5 ml solution was sampled and run through MACS columns ((25 LD columns, Miltenyi Biotec, Germany)) to separate free Ce6 released from Ce6 nanoclusters. UV-absorption spectroscopy was used to determine the amount of Ce6 in the purified Ce6 nanocluster samples. Normalized peak absorbance was measured over 2 days and the cumulative release percentage of Ce6 was plotted as a function of incubation time.

MTS Assay.

Human umbilical vein endothelial (HUVEC) and 4T1 cells ($1 \times 10^4$ cells per well) were seeded in 96-well plates and incubated overnight to allow the cells to attach to the surface of the wells. The cells were then mixed with increasing concentrations of Ce6-SCs for 24 h, and the cell viabilities were determined using an MTS assay (Abcam Inc.) according to the supplier's instructions. Briefly, after 24 h of incubation with Ce6-SCs, 10 ul of MTS reagent was added. After 2 h, absorbance was read at 490-nm on a Tecan microplate reader.

Phantom and animal imaging by MR.

Relaxometry measurements were performed in $T_2$* mode (Varian, 4.7 T); Iron concentration was determined by ICP-OES. A plastic 384-well plate (MR phantom) was used to test the $T_2$ hypointensity associated with Ce6-SCs compared to control (i.e., water) on a 4.7 T magnet. [Fe] concentrations were as follows: 0.5, 0.25, 0.125, 0.0625, and $0.0312 \times 10^{-3}$ m. Unenhanced MR images of the mice bearing 4T1 flank xenografts were first obtained, and then MRI was performed 24 h after the intravenous injection of Ce6-SCs at a dose of 2.5 mg kg$^{-1}$ (based on Fe mass) via retro-orbital injection. The MR acquisition parameters were as follows: TR 200 ms, TE 5 ms, matrix 128×128, and gap 0. Contrast enhancement on $T_2$*-weighted imaging (seen as hypoenhancement following injection of Ce6-SCs) was quantified using ImageJ. The region of interest of tumor (signal) was normalized to the paraspinous musculature as background and expressed as a signal-to-background ratio (SBR). T-test comparisons were made between the mean SBRs in animals pre-injection versus post-injection, with a p-value of <0.05 considered to be statistically significant.

Phantom and Animal Imaging by Fluorescence.

Serial 1/2×dilutions from [40 μg mL$^{-1}$] to 1/32×[1.25 μg mL$^{-1}$] of Ce6 in DMSO/water (1/20, v/v) solution were used in a 96-well plate as a control. 5% DMSO was necessary to improve the solubility of Ce6 in water. An equivalent amount of Ce6-SCs was dissolved in the same solution for comparison. For the in vivo animal experiments, 4T1 tumor cells were introduced into female nude mice. When the tumor volume reached about 80 mm$^3$, Ce6-SCs nanoparticles (dose: equivalent Ce6 2.5 mg/kg) and free Ce6 (dose: 2.5 mg/kg) were injected intravenously into the tumor-bearing nude mice. Images were acquired with a Perkin Elmer IVIS Spectrum In Vivo System (excitation, 640 nm; emission, 720 nm; exposure time, Auto; binning 4; and f=2).

In Vitro PDT.

For in vitro PDT experiments, 4T1 cells (1×10$^4$ cells) were seeded onto 96-well cell culture plates and incubated for 24 h with various concentrations of Ce6-SCs (0.625, 1.25, 2.5, 5, and 10 μg/mL based on the Ce6 concentration). The cells were then irradiated with a 665 nm diode laser (B&W Tek, Inc.) to a dose of 5 J/cm$^2$ (16.40 min), while the control groups were still cultured in the dark. Illumination was delivered through microlens-tipped fibers (Pioneer), and intensity of laser output was monitored and adjusted (Lab-Master power meter; Coherent) to a power density of 5 mW/cm$^2$. Afterward, all samples were incubated in the dark for another 24 h. Cell viability was measured by the MTS colorimetric assay and recorded as the percentage of live cells in the treated samples compared with the percentage of live cells in the untreated control.

In Vivo PDT of Ce6-SCs in 4T1 Tumor-Bearing Mice.

4T1 tumors cells (5×10$^6$ cells in 100 ul) were implanted in the right flank of athymic nude female mice (aged 6 weeks). When the tumor size reached approximately 80 mm$^3$, free Ce6 (2.5 mg/kg of Ce6), and Ce6-SCs (2.5 mg/kg of Ce6) were injected into the mice via retro-orbital injection. At 24 h post-injection, mice were irradiated (30 min) at the tumor site with 665 nm light (B&W Tek, Inc. diode laser) to a dose of 135 J/cm$^2$ at a power density of 75 mW/cm$^2$. The therapeutic efficacy of the treatments was monitored by measuring the tumor volumes calculated as 1/2×(length× width$^2$). All measurements were made with a caliper.

Results

Synthesis and Physical-Chemical Characterization of Ce6-SCs.

Figure 23A:
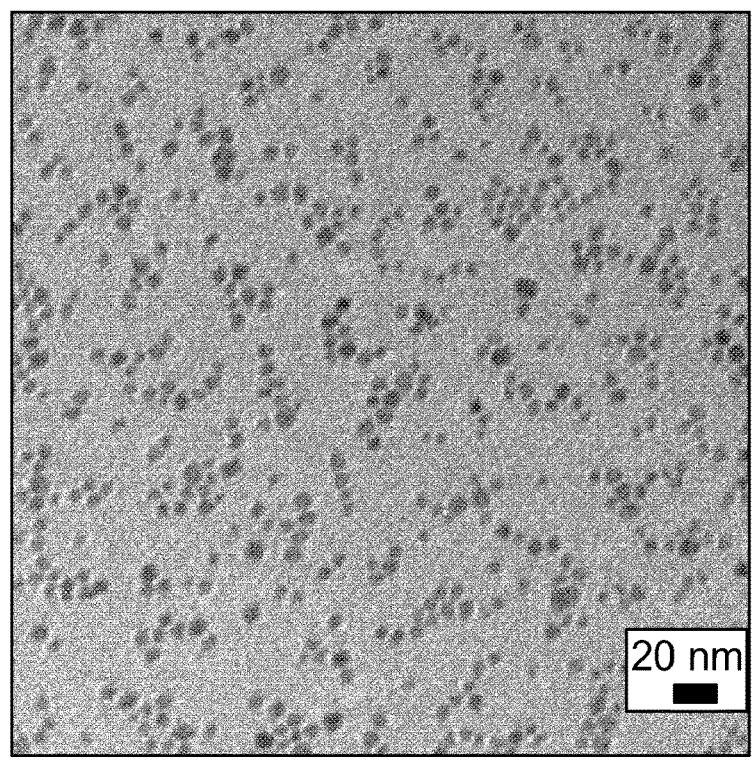
FIGS. 23A-23B.
Figure 23B:
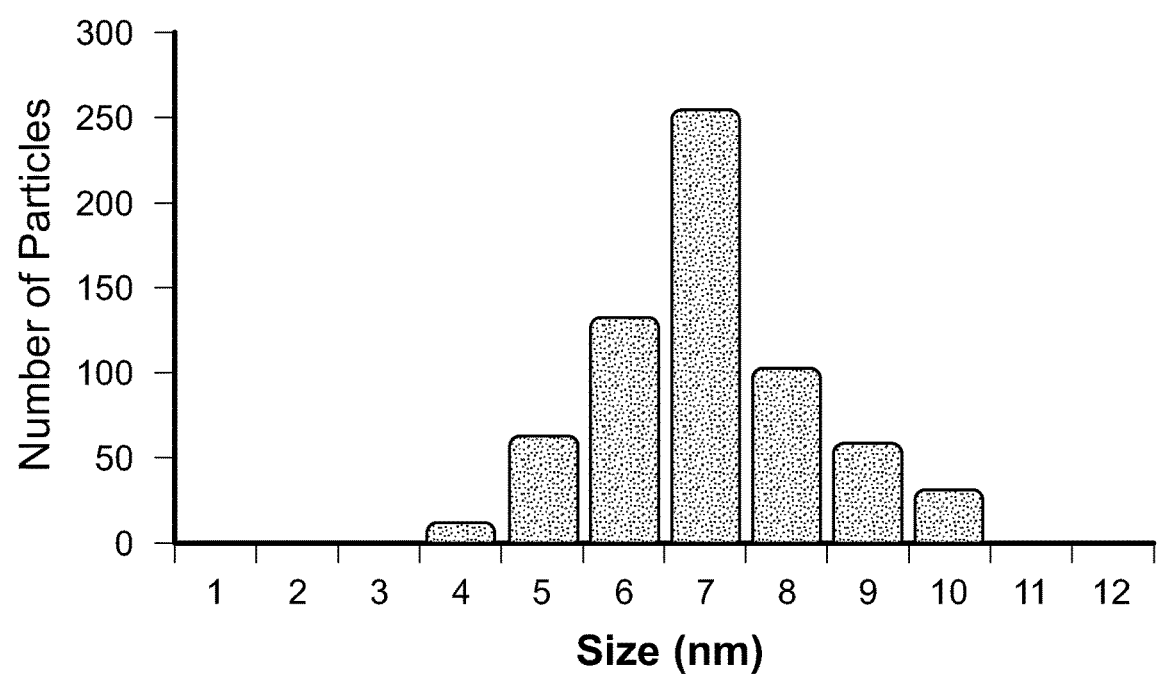

Ce6-SCs (FIG. 22A) were prepared by simply dissolving two clinically-used functional materials, Ce6 and SPIONs (diameter=7.6±1.0 nm; FIG. 23A-23B) at a ratio of 2:1, into the oil phase of an oil-in-water emulsions. No additional amphiphiles or carrier materials were required. The amphiphilic Ce6 molecules solubilized the hydrophobic SPIONs, creating stable nanoclusters with an average hydrodynamic diameter of 96.38±4.6 nm and an average polydispersity index (PDI) of <0.2 (FIG. 22B). Transmission electron microscopy (TEM) images confirmed the formation of tightly packed SPIONs nanoclusters with a narrow size distribution (FIG. 22B, inset). The preparation of Ce6-SCs was highly reproducible (Table 3) and easily scalable.

TABLE 3

Repeatability of Ce6—SCs synthesis

|  | Batch 1 | Batch 2 | Batch 3 | Average | St. Dev. |
|---|---|---|---|---|---|
| Hydrodynamic Diameter (nm) | 97.03 | 100.7 | 91.42 | 96.38 | 4.67 |
| PDI | 0.201 | 0.190 | 0.184 | 0.19 | 0.0086 |
| Relaxivity (r$_2$) (mM$^{-1}$s$^{-1}$) | 215 | 220 | 247 | 227 | 17.2 |

The effect of varying the amount of Ce6, with a fixed amount of SPIONs, on the physical-chemical properties of the Ce6-SCs was evaluated. All measurements were made after free Ce6 was removed by a magnetic purification. It was found that the encapsulation efficiency is >96% for SPION and >90% for Ce6, when the Ce6:Fe ratio (w/w) is in the range of 1:3 to 1:2.5 (Table 4), which is noticeably higher than most other methods that have been used to solubilize Ce6. The Ce6 payload was approximately 25% of the total weight (Ce6+Fe) at these same ratios. Increasing the Ce6:Fe ratio to 2:1 led to a reduction in encapsulation efficiency to 65%, but the payload increased to 56% of the total weight. Interestingly, the hydrodynamic diameter was similar (90-97 nm) for all of the conditions tested, except the lowest Ce6:Fe ratio (1:3), which resulted in Ce6-SCs with a slightly larger diameter of ~115 nm. The r$_2$ relaxivity of the Ce6-SCs increased from 247 mM$^{-1}$ s$^{-1}$ to 410 mM$^{-1}$ s$^{-1}$ as the Ce6:Fe ratio decreased from 2:1 to 1:3. The PDI was <0.2 for all conditions tested. Ce6-SCs formed using a Ce6:Fe ratio of 1:1 were used for all subsequent studies, since they provided balanced values for encapsulation efficiency, payload, and relaxivity.

TABLE 4

Physical-chemical properties of Ce6—SCs as a function of starting Ce6:Fe ratio (w/w).

| | Starting Ce6:Fe Ratio (w/w) | | | | |
|---|---|---|---|---|---|
| | 2:1 | 1:1 | 1:2 | 1:2.5 | 1:3 |
| Encapsulation Efficiency (%) | 65.39 | 71.06 | 81.07 | 90.87 | 100 |
| Ce6 Payload: Ce6/ (Ce6 + Fe) (%) | 56.52 | 41.52 | 28.35 | 26.11 | 24.39 |
| Relaxivity (r$_2$) (mM$^{-1}$s$^{-1}$) | 247 | 301 | 369 | 382 | 410 |
| Hydrodynamic Diameter (nm) | 91.42 | 90.03 | 92.6 | 96.8 | 114.4 |
| PDI | 0.184 | 0.165 | 0.147 | 0.158 | 0.156 |

Stability of Ce6-SCs.

Figure 25:
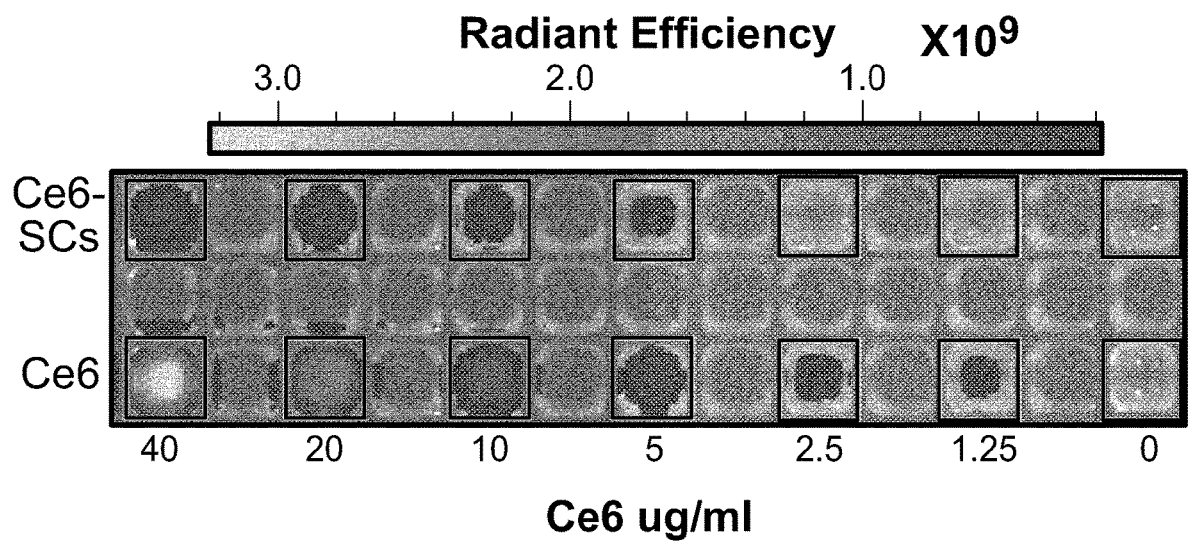
FIG. 25 Fluorescent image of a microplate containing increasing concentrations of Ce6-SCs (top row) and Ce6 free (bottom row) in 5% DMSO/95% water. Instrumentation/parameters: Perkin Elmer IVIS Spectrum In Vivo System (excitation 640 nm, emission 720 nm, exposure time=Auto, binning 4, f=2).

Ce6-SCs demonstrated size stability in water without aggregation or precipitation as indicated by no significant changes in the T2 relaxation time (FIG. 22C) or hydrodynamic diameter over the course of at least 6 days. Relaxometry measurements indicated an average r$_2$ value of 301±4 mM$^{-1}$ s$^{-1}$ and MR images of a phantom confirmed strong T$_2$ contrast relative to water (FIG. 22D). Analysis of the absorbance spectrum of Ce6-SCs reveals a distinct peak at ~665 nm, suggestive of excellent solubility. In comparison, there was no absorbance peak for free Ce6 (FIG. 22E, inset), owing to its poor solubility and susceptibility to aggregation. Not surprisingly, the loading of the high payload of Ce6 on nanoclusters does result in decreased fluorescent intensities, due to both self-quenching and iron-mediated quenching (FIG. 25).

Figure 24A:
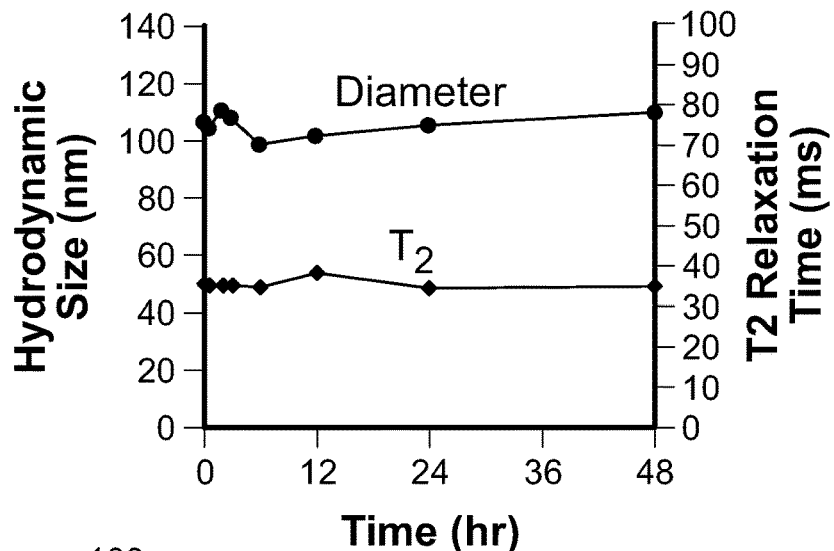
FIGS. 24A-24D (FIG. 24A) Ce6-SCs were incubated in serum, at 37° C. Hydrodynamic size and T2 relaxation time were monitored as a function of time.
Figure 24B:
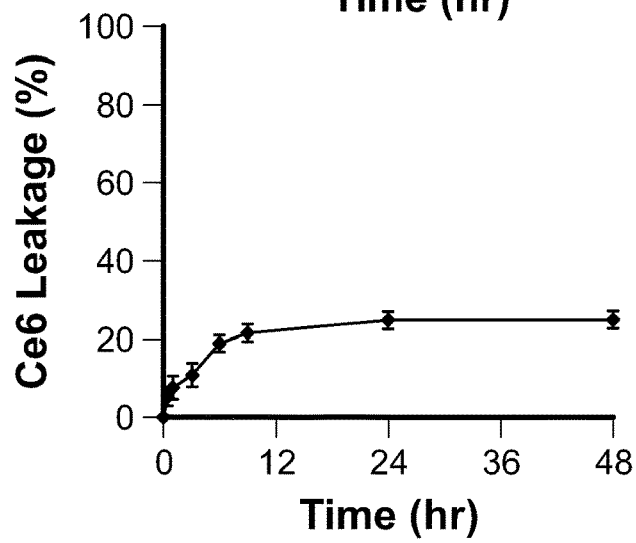

The stability of Ce6-SCs was tested by incubating Ce6-SCs in FBS for 48 h at 37° C. under constant shaking. The hydrodynamic diameter of Ce6-SCs increased by 10-15 nm immediately upon addition to serum, due to protein absorption, but then remained constant over the remaining 48 h. No aggregation or precipitate was observed and there was no remarkable change in the T2 relaxation time (FIG. 24A). The release of Ce6 from Ce6-SCs was evaluated by magnetic separation. As shown in FIG. 24B, the percentage of Ce6 leaking from the nanoparticles was only about 22% within 9 h after addition of serum, and then no further release was detectable for up to 48 h. These results confirm that the Ce6 forms a highly stable interaction with the SPION surface.

Singlet Oxygen Production with Ce6-SCs.

Figure 27A:
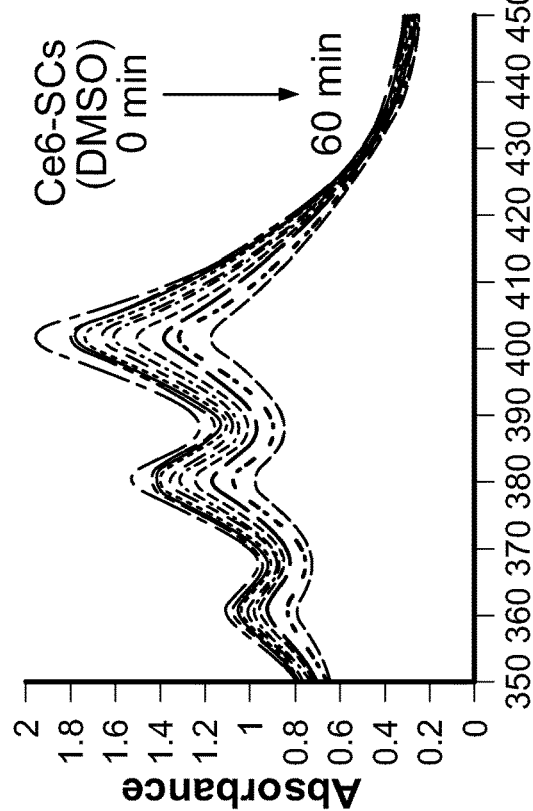
FIGS. 27A-27D Comparison of the singlet oxygen generation rate of various Ce6 formulations. The absorption spectra of 9,10-Anthracenediyl-bis-(methylene)dimalonic acid (ABDA, 30 uM) after photodecomposition by ROS generation in the presence of (FIG. 27A) Free Ce6, (FIG. 27B) Ce6-SCs in DMSO and (FIG. 27C) Ce6-SCs in water at the same dose of Ce6 (10 uM) for different exposures from 0 to 60 min. The method for $^1O_2$ detection by UV-vis spectroscopy was based on the protocol reported previously. Briefly, different Ce6 formulations (Ce6=10 uM) were prepared in 15 mL DMSO and water in presence of 30 uM 9,10-Anthracenediyl-bis-(methylene)dimalonic acid (ABDA). Then the solutions were irradiated under a laser (λ=665 nm, power density=5 mW/cm$^2$), and aliquots of sample solution were removed from the irradiated sample at predetermined intervals and subjected to UV-vis absorption measurement. The absorbance change of ABDA at 350-500 nm under different laser-irradiation periods was monitored.
Figure 27C:
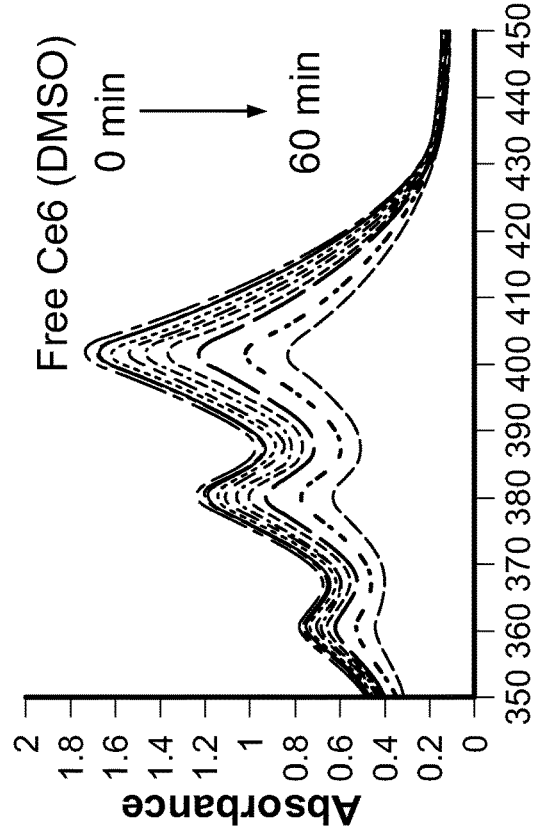
Figure 27B:
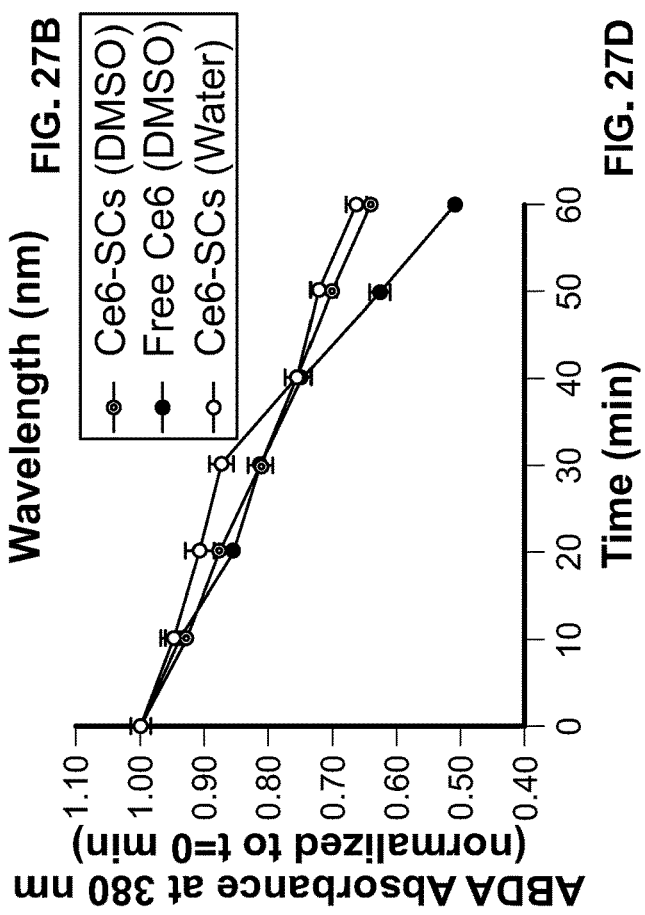
Figure 27D:
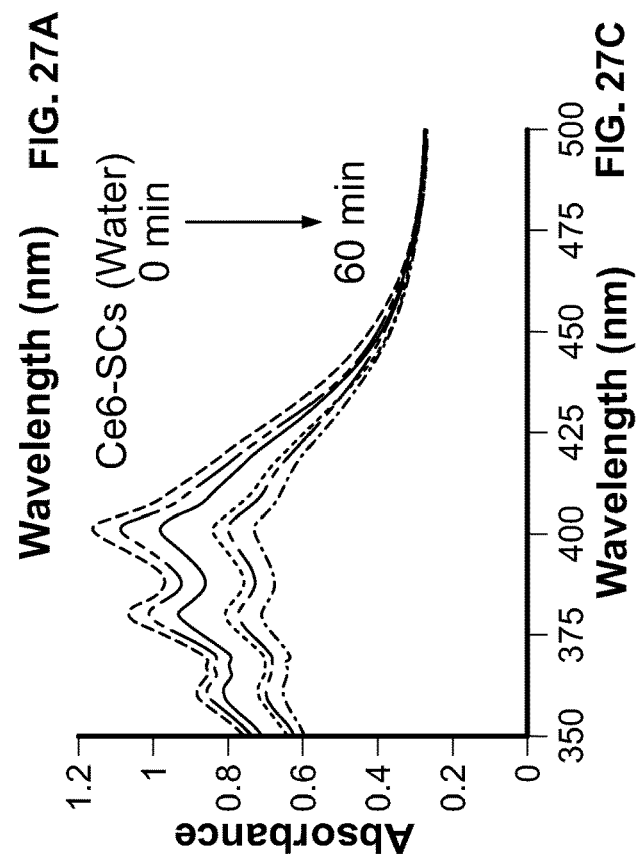

To explore singlet oxygen ($^1O_2$) generation efficiency of Ce6-SCs compared with free Ce6, the absorbance spectrum of ABDA was monitored, a chemical-sensitive probe of ROS, in response to light irradiation at 665 nm (5 mW/cm$^2$) as a function of time (FIGS. 27A-27B). Upon irradiation, the optical density of ABDA decreased rapidly for both Ce6-SCs and free Ce6. Incorporation of Ce6 into the nanoclusters resulted in little to no reduction in singlet oxygen production, despite being densely packed on the surface of SPIONs. High singlet oxygen production was also observed regardless of whether the Ce6-SCs were in water or DMSO (FIGS. 27B-27C). These findings suggest that single oxygen production from Ce6 is not significantly quenched when incorporated into Ce6-SCs. The inventors attempted to compare the singlet oxygen production of Ce6-SCs with Ce6 that had been encapsulated in micelles, to see if the lack of quenching was unique to Ce6-SCs, due to the likely alignment of the amphiphilic Ce6 with its hydrophobic domains facing the SPIONs and its hydrophilic domains facing the surrounding water. In micelles, Ce6 is likely to be randomly oriented. Unfortunately, encapsulation of Ce6 in micelles was not successful due to the amphiphilic nature of Ce6.

To explore how the singlet oxygen production of Ce6 and Ce6-SCs compares to Protoporphyrin IX (PpIX), a common PS with a similar chemical structure, and PpIX-coated SPION nanoclusters, the absorbance spectrum of ABDA of these samples was monitored, but in response to light irradiation at 632 nm (5 mW/cm$^2$), the peak absorbance of PpIX (FIGS. 29A-29E). Like Ce6, significant singlet oxygen production was observed for both the free PpIX and PpIX-SCs, with the PpIX-SCs only exhibiting a slightly lower level of singlet oxygen production. However, when PpIX was encapsulated within micelles, no singlet oxygen production was observed upon irradiation. These findings suggest that the orientation of the Ce6 and PpIX on the surface of SPION nanoclusters could be helping to limit the extent of singlet oxygen quenching that is observed.

Cytotoxicity and Phototoxicity of Ce6-SCs.

Figure 24C:
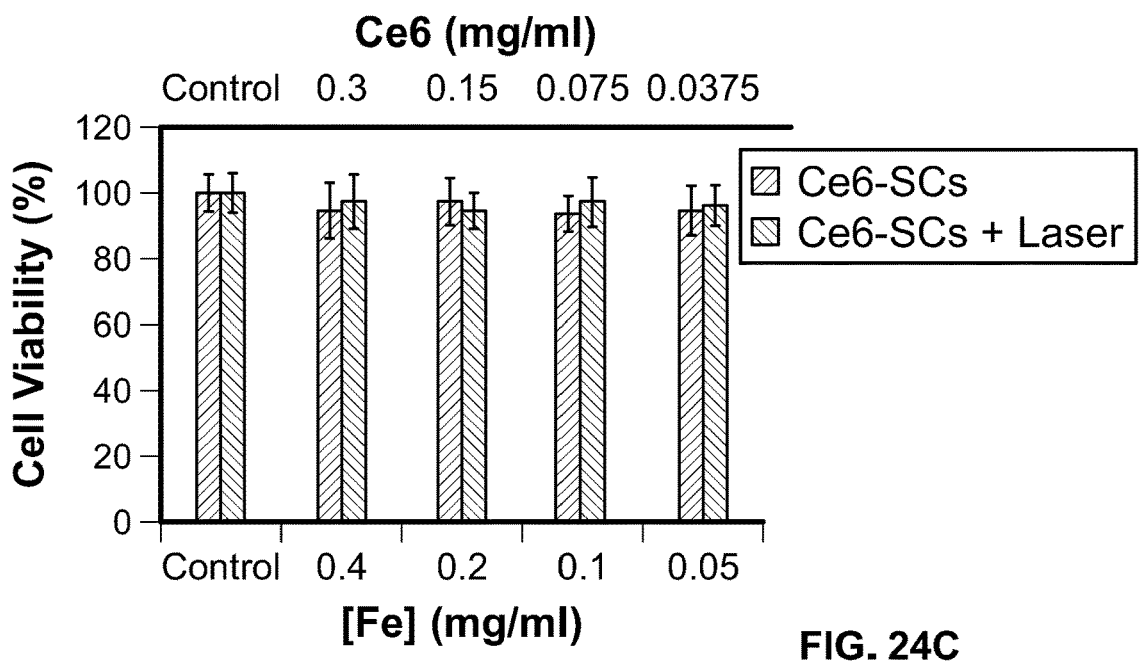
Figure 30:
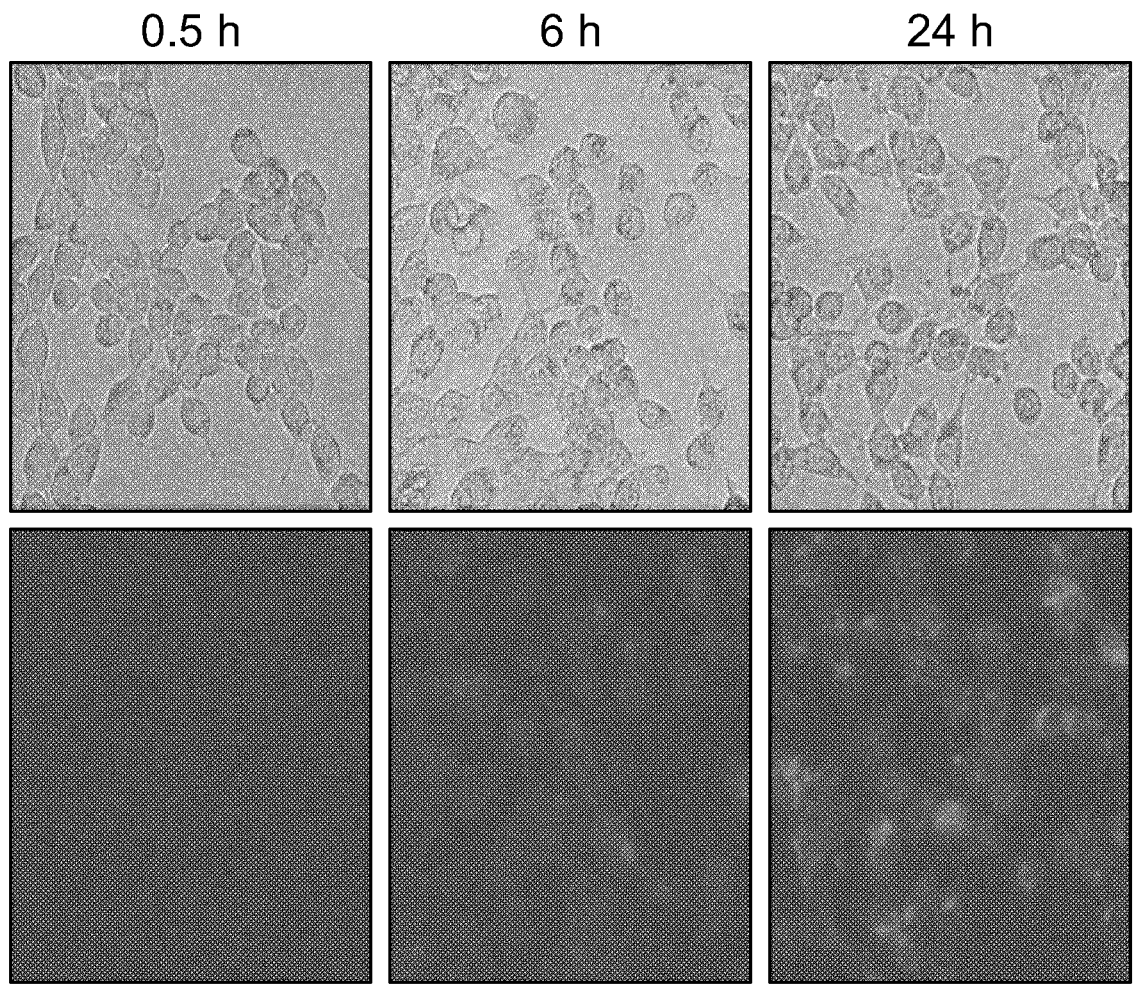
FIG. 30 Phase contrast (top row) and fluorescence microscopy (bottom row) images of 4T1 cells incubated with Ce6-SCs for 0.5, 6, and 24 h.

To ensure that Ce6-SCs can be safely injected into mice, the cytotoxicity of the Ce6-SCs, without irradiation, was examined in an MTS cell proliferation assay. Increasing concentration of Ce6-SCs were incubated with cells for 24 hours. It was found that the Ce6-SCs exhibited no obvious cytotoxicity to 4T1 murine breast cancer cells or human umbilical vein endothelial human embryonic (HUVEC) cells, even at relatively high concentrations of Fe (up to 400 µg/mL) and Ce6 (up to 300 µg/mL), respectively (FIG. 24C). Cellular uptake of Ce6-SCs was monitored by fluorescence microscopy, where a time-dependent increase in fluorescence intensity was observed at different time intervals from 0.5 to 24 h (FIG. 30).

Figure 24D:
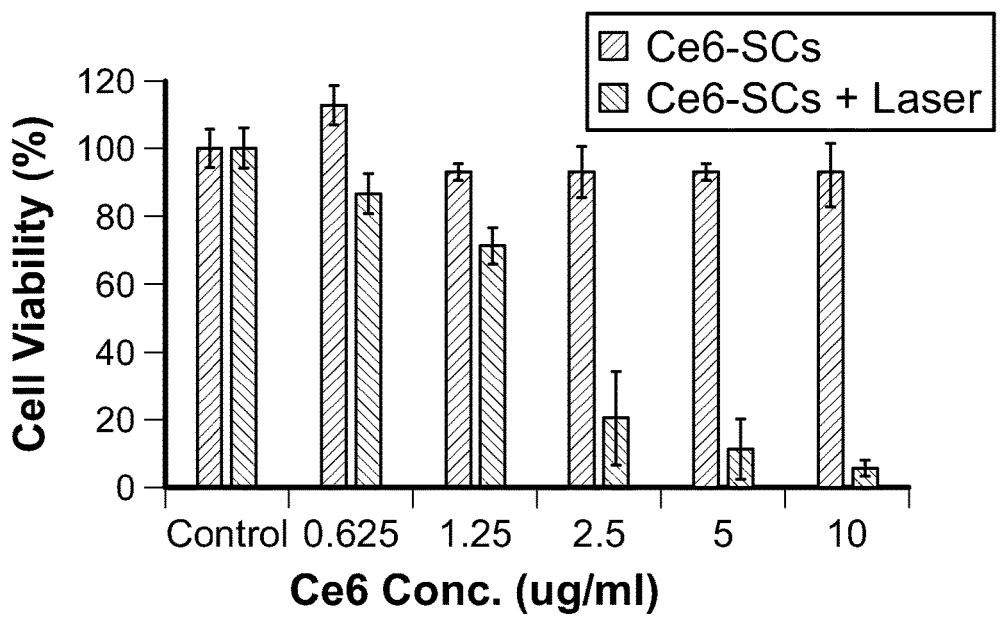
Figure 31A:
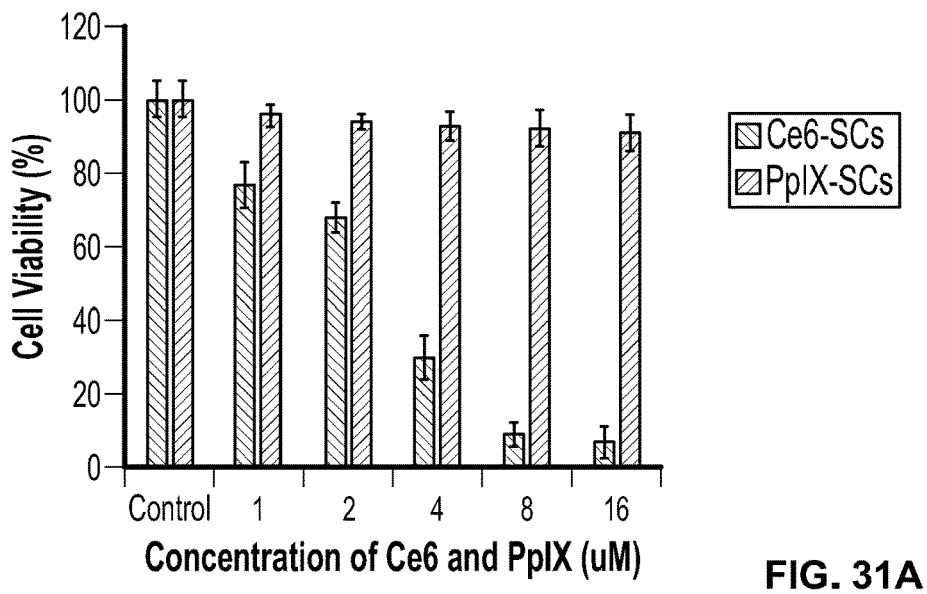
FIGS. 31A-31C Viability of 4T1 cells treated with different concentrations of Ce6-SCs and PpIX-SCs and irradiated with a (FIG. 31A) 665 nm and (FIG. 31B) 632 nm laser. These wavelengths correspond to the absorbance peak of each PS.
Figure 31B:
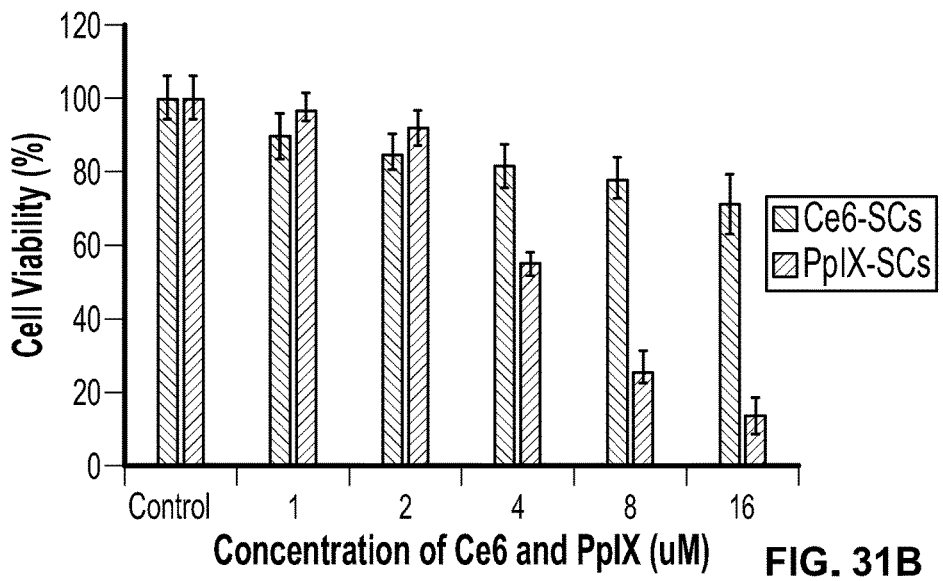
Figure 31C:
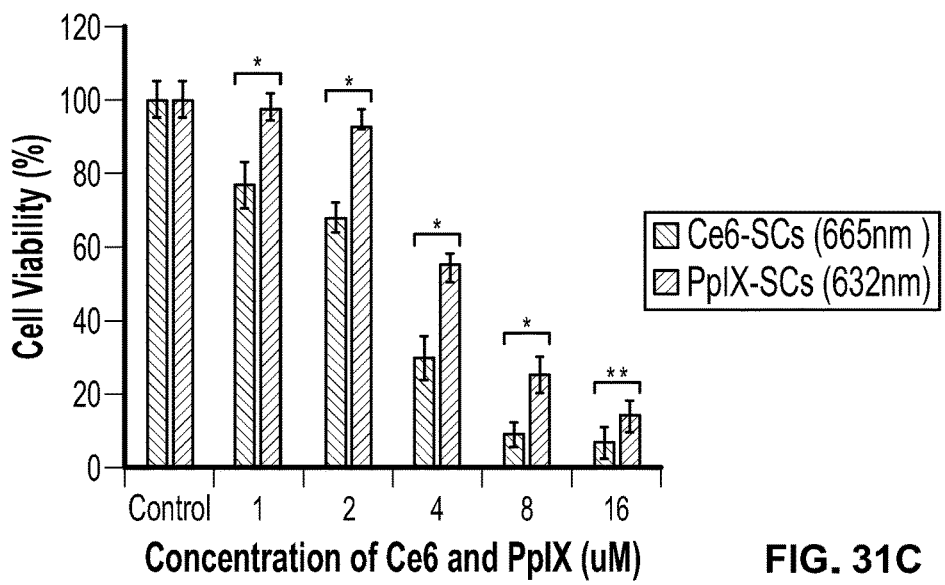

The phototoxicity of Ce6-SCs was also examined with 4T1 cells as a function of Ce6-SC concentration using MTS assays (FIG. 24D). Increasing the concentration of Ce6-SCs led to a direct increase in phototoxicity, upon irradiation with a 665 nm laser (5 J/cm$^2$), with less than 10% viability observed at a dose of just 10 µg/mL. Ce6-SCs alone did not induce any significant toxicity to 4T1 cells, nor did irradiation alone. Ce6-SCs also exhibited a statistically significant improvement in phototoxicity compared with PpIX-SCs, when irradiated at their respective peak absorbances (FIGS. 31A-31C).

Evaluation of Ce6-SCs in a Murine Tumor Model.

To demonstrate the contrast-enhancing capabilities of Ce6-SCs in a murine tumor model, 4T1 breast cancer cells were implanted subcutaneously in the flank of athymic nude mice. In vivo, MR imaging was then conducted before and 24 h after intravenous injection of Ce6-SCs to track their accumulation within tumors. As shown in FIG. 26A, a significant loss in signal (i.e., hypointensity) was observed in the flank tumors following injection, consistent with the accumulation of SPIONs. Signal-to-background (SBR) measurements were performed using the tumor and the paraspinous musculature as background. The post injection SBR was significantly lower at 0.23±0.04 compared to the pre-injection SBR of 1.01±0.05, p<0.001 (FIG. 26B).

The Ce6-SCs within the tumor were also detectable via fluorescence imaging (FIG. 26C), despite the significant degree of quenching in the stock formulation. The signal was significantly higher than observed following the intravenous injection of free Ce6, confirming that the accumulation of Ce6-SCs in tumors is much more efficient than that of free Ce6 (FIG. 26D).

Next, the inventors investigated the efficacy of PDT on the inhibition of tumor-cell growth in athymic mice bearing 4T1 flank tumors. Tumors were allowed to grow to sizes of 5-6 mm in diameter prior to PDT treatment. Mice (5-7 mice/group) were divided into four treatment groups (i) Ce6-SCs+PDT; (ii) free Ce6+PDT; (iii) Ce6-SCs alone; and (iv) untreated controls. Ce6-SCs and free were intravenously injected at the same Ce6 concentration (2.5 mg/kg) then irradiated with a 665 nm laser at a power density of 75 mW/cm$^2$ to a dose of 135 J/cm$^2$ (30 min), 24 h post-injection. Tumor volume was measured daily post-irradiation for a period of 10 days. The rate of tumor growth was significantly slowed in mice that received Ce6-SCs+PDT compared with mice that received free Ce6+PDT (day 10, P<0.001) (FIG. 28). There was no a significant loss of weight in any of the treatment groups following PDT (FIG. 28). As expected, the Ce6-SCs were nontoxic in their native state but damaged target tumor cells when irradiated.

In conclusion, the inventors successfully developed a novel nanoformulation by coating nanoclusters of SPIONs with the photosensitizer Ce6. The method is efficient, only requires the use of two clinically-used compounds and is highly reproducible. The synthesized nanoclusters were systemically characterized in vitro and in vivo. The nanoclusters possess high solubility and stability in serum and good biocompatibility, thus facilitating its use biomedical applications, particularly for cancer theranostics. Ce6-SCs showed high Ce6 and SPIONs encapsulation efficiency and high Ce6 payloads. The Ce6-SCs also exhibited enhanced delivery of Ce6 into tumors, compared with free Ce6, and could be visualized by both MR and fluorescence imaging. The therapeutic activity of Ce6 molecules in Ce6-SCs was minimally reduced when incorporated onto SPION nanoclusters and exhibited efficient phototoxicity in tumor-bearing mice because of the enhanced delivery into the tumor, compared with free Ce6. Based on the inventors' findings, Ce6-SCs represent a promising theranostic agent for clinical applications.

Example 5

Synthesis of Azide-Functionalized Indocyanine Green (ICG-N$_3$) and Protoporphyrin IX (PpIX-N$_3$)

The use of nanoparticles as a drug delivery platform has received a significant amount of attention in recent years, due to their ability to reduce off-target effects, extend drug circulation, and improve the treatment of disease. The types of nanocarriers that exist are diverse and include liposomes; polymeric nanoparticles; polymeric micelles; silica, gold, silver and other metal nanoparticles; carbon nanotubes; solid lipid nanoparticles; and dendrimers. As discussed herein, the inventors have introduced a new class of nanoparticles, whereby amphiphilic functional dyes such as the near-infrared fluorescent dye Indocyanine Green (ICG) and the photosensitizer Protoporphyrin IX (PpIX) (i.e., clinically-used functional materials) are used to drive the formation of stable nanoemulsions, without the use of any amphiphilic polymers or surfactants. Hydrophobic materials such as superparamagnetic iron oxide nanoparticles (SPIONs) can be encapsulated in the nanoemulsions to confer additional functionality. It has also been shown that small-molecule drugs can be packaged into nanoemulsions using a similar approach. These dye-stabilized nanoemulsions allow for extremely high drug payloads and have been shown to exhibit improved functionality compared with free drug and even analogous micelle carriers. However, dye-stabilized nanoemulsions have yet to be functionalized with targeting ligands. The surface chemistry and chemical handles available for bioconjugation are dependent on the dye used and for some dyes no chemical handle is available for subsequent bioconjugations. Preferably, a bio-orthogonal chemical handle would be available for the attachment of targeting ligands via click-chemistry. Click chemistry is a highly efficient and specific reaction chemistry that has become the preferred approach for bioconjugations. One of the most popular click chemistry reactions occurs between an azide and a constrained alkyne, with efficiencies nearing 100%, without copper catalysts.

The attachment of targeting ligands to nanoparticles is desirable because it has the potential to increase tumor accumulation, specificity, and therapeutic efficacy. While many nanoparticles rely primarily on enhanced permeability and retention (EPR) for preferential accumulation at tumor sites, active targeting is generally preferred to more specifically deliver drugs to the desired cell type based on molecular recognition processes such as ligand-receptor or antibody-antigen interactions. Targeting has also been shown to trigger cellular uptake for more effective delivery of drug to intracellular targets. Despite the benefits of targeting, low bioconjugation efficiencies, high batch-to-batch variability, and the inability to control the orientation and density of the targeting ligands on the nanoparticle surface slows clinical translation. Herein, described is a strategy for the site-specific and efficient attachment of targeting ligands onto carrier-free, dye-stabilized nanoemulsions.

Preparation of Antibody Conjugated Nanocluster

To prepare antibody-conjugated nanocluster, 20 uM of azide-functionalized nanoclusters (based on the ICG-N$_3$ and PpIX-N$_3$ concentration) and were reacted with 40 uM of DBCO-functionalized antibody in 1 ml of PBS for 12 h at room temperature with shaking. The antibody conjugated nanoclusters were washed with PBS several times by using centrifugal filter (50K, Amicon Ultra) to remove free antibody.

Characterization of ISCs-HER2 and PSCs-HER2

The diameter and size distributions of the HER2-targeted nanoclusters were measured with dynamic light scattering (DLS, Malvern, Zetasizer, Nano-ZS). The morphology of the nanoparticles was observed using a transmission electron microscope (TEM) (JOEL 1010). $T_2$ relaxation times were measured using a benchtop relaxometer (Bruker, mq60 NMR analyzer). Iron concentration was quantified by plasma optical emission spectroscopy (ICP-OES) (Spectro Genesis, GMBH).

Cell Viability Assay

T6-17 cells ($1\times10^4$ cells per well) were seeded in 96-well plates and incubated overnight to allow the cells to attach to the surface of the wells. The cells were then mixed with increasing concentrations of HER2-targeted nanoclusters 24 h, and the cell viabilities were determined according to the supplier's instructions. After 24 h of incubation, 10 ul of MTS reagent was added. After 2 h, 490-nm absorbance was read on a Tecan microplate reader.

Cellular Binding/Uptake Measured by Fluorescence Microscopy

Fluorescence microscopy was used to determine the cellular binding behavior of ISCs-HER2 and PSCs-HER2 nanoclusters. T6-17 cells were utilized upon seeding in a 12-well plate at a density of $2\times10^5$ cells per well. The cells were submerged in 2 mL of DMEM cell culture medium and incubated in a 5% CO2 environment at 37° C. for 24 h. After incubation, the original culture medium was removed and incubated with HER2-targeted nanoclusters at ICG and PpIX concentration of 10 uM in newly added DMEM for 1 h. The cells were washed with phosphate buffer saline (PBS) two times to remove excess nanoclusters that were not uptaken by the T6-17 cells. As a negative control, we prepared and used non-targeted nanocluster, ISCs-EGFR and PSCs-EGFR nanoclusters at the same condition. Microscopy images were taken with an Olympus IX81 motorized inverted fluorescence microscope with a back-illuminated EMCCD camera (Andor), an X-cite 120 excitation source, and Sutter excitation and emission filter wheels.

Cellular Targeting

T6-17 cells were incubated with 100 μg Fe/mL of HER2-targeted nanoclusters for 1 h in full media in triplicate. The media was removed and the cells were washed with PBS two times to remove any unbound nanoclusters. Cells were harvested and counted. Cell suspensions were diluted to $5\times10^5$ cells/ml and $T_2$ relaxation times were measured using a benchtop relaxometer (Bruker mq60).

Figure 32A:
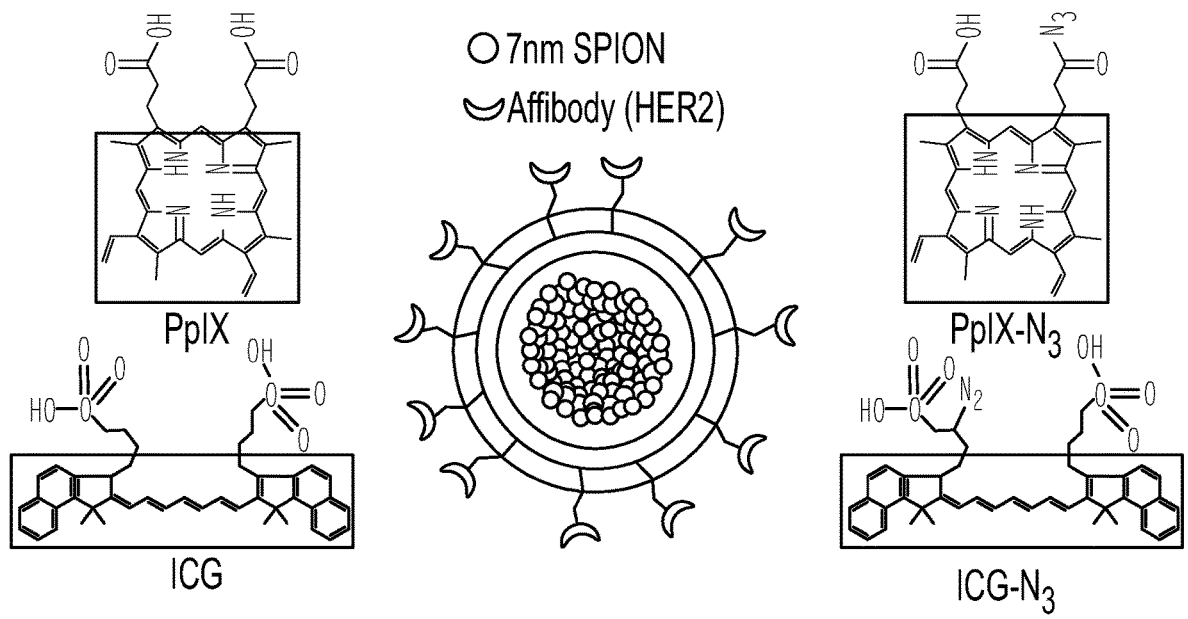
FIGS. 32A-32D show the formation of azide-modified variants of PpIX and ICG, their combination of the dye mixture with SPIONS and preparation of HER2-targeted nanoclusters with either ISCs or PSCs.
Figure 32B:
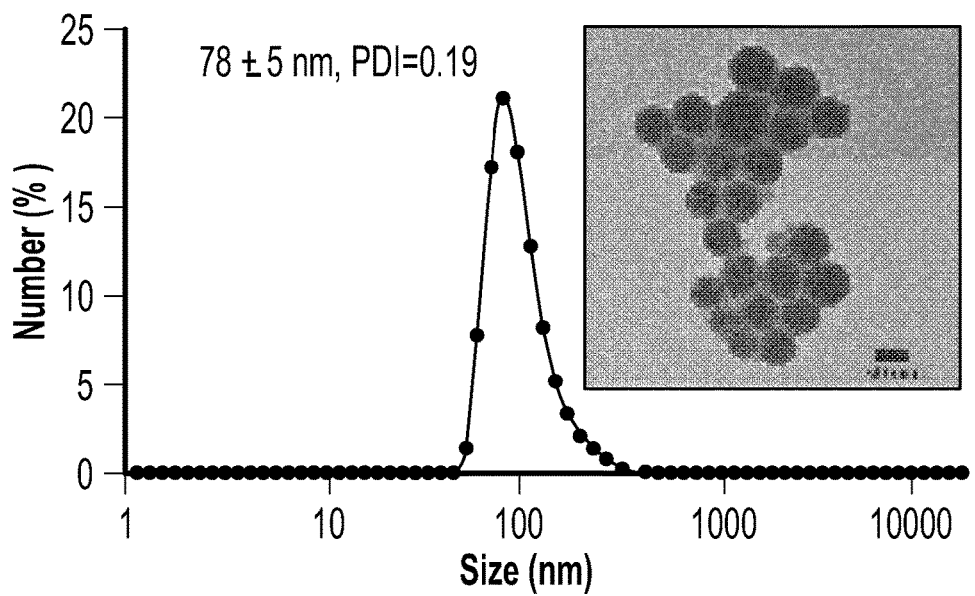
Figure 32C:
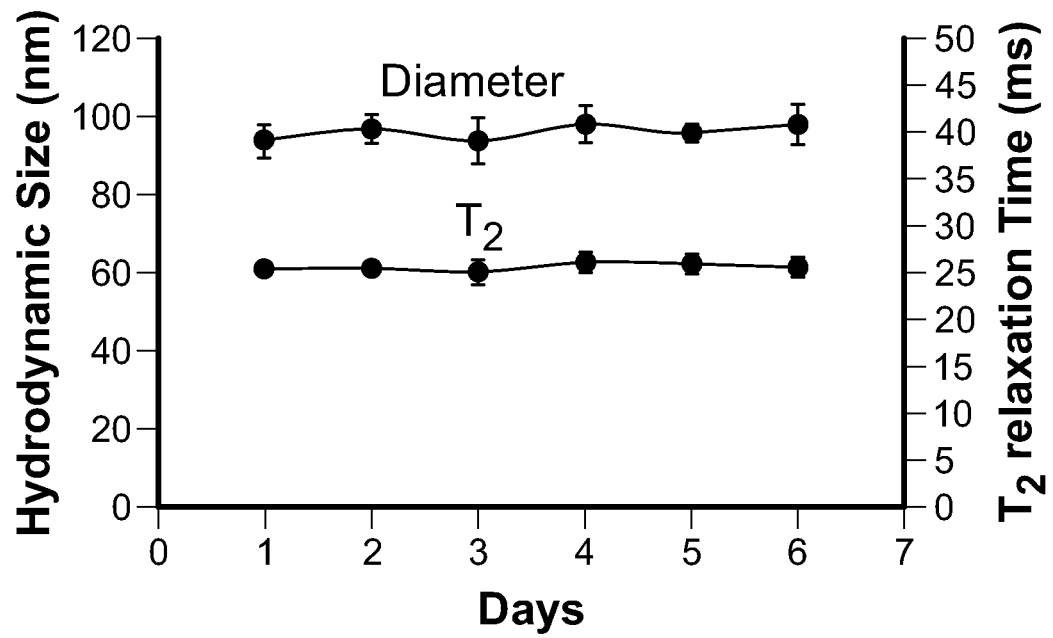
Figure 34A:
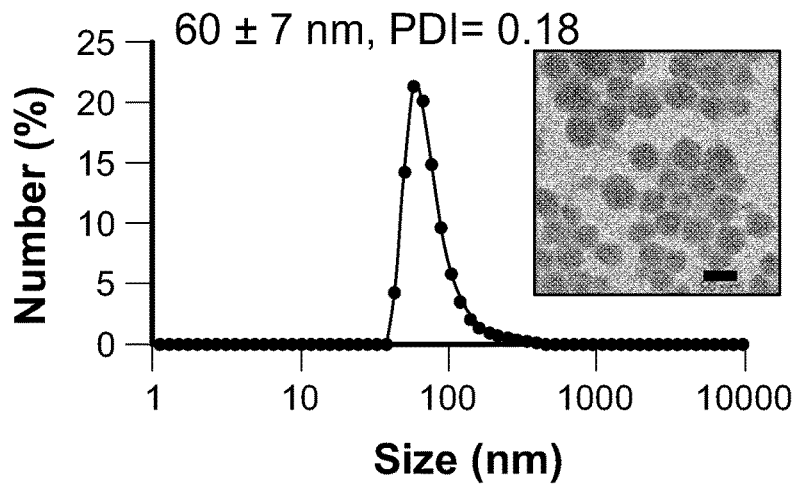
FIGS. 34A-34C show HER2-targeted nanoclusters (HER2-PSCs).
Figure 34B:
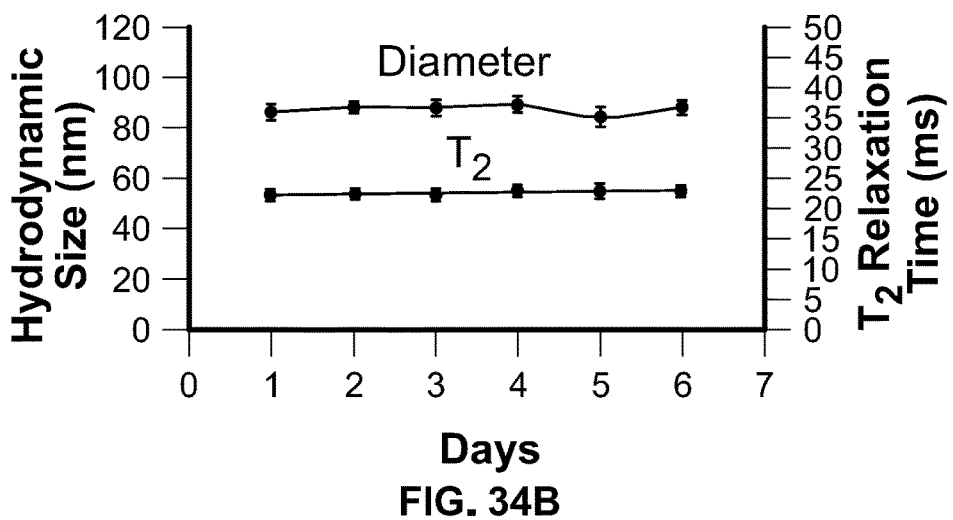

Azide-handles for click-chemistry were introduced onto the surface of dye-stabilized nanoemulsions, by first preparing azide-modified variants of PpIX and ICG (FIG. 32A). The azide was introduced near the hydrophilic sulfate and carboxyl groups of ICG and PpIX, respectively, to increase the likelihood that it would be exposed to the surrounding aqueous medium and available for subsequent conjugations. The structure of the azide variants was confirmed by mass spectrometry and NMR. Azide-functionalized nanoemulsions were formed by first dissolving the azide-dyes at a 1:20 molar ratio with unmodified dye in toluene. This dye mixture was combined with SPION (SPIONs, diameter=7.6±1.0 nm) in toluene at a ratio of 1:1 w/w. No additional amphiphiles or carrier materials were applied. The sample was sonicated in water to form the nanoemulsion and purified by dialysis. The amphiphilic ICG-N$_3$/ICG and PpIX-N$_3$/PpIX mixtures solubilized the hydrophobic SPIONs, creating stable ICG-SPION clusters (ISCs) and PpIX-SPION clusters (PSCs), respectively. The average hydrodynamic diameter of the ISC and PSCs was 78±5 nm and 60±7 nm, respectively. The average polydispersity index (PDI) was <0.2 for both formulations (FIG. 32B, FIG. 34A).

Anti-Her2 targeting affibodies were used as a model targeting ligand and were site-specifically modified at the C-terminus with a constrained alkyne, dibenzocyclooctyne (DBCO), via sortase-tagged expressed protein ligation (STEPL). Briefly, the affibody was expressed as a fusion protein with the sortase-recognition motif, sortase, and a histidine affinity tag. Once captured on affinity resin, the addition of a triglycine peptide modified with DBCO, led to the sortase mediation ligation of the peptide onto the affibody and release of the anti-Her2 affibody-DBCO conjugate (HER2-DBCO) from the column.

Figure 32D:
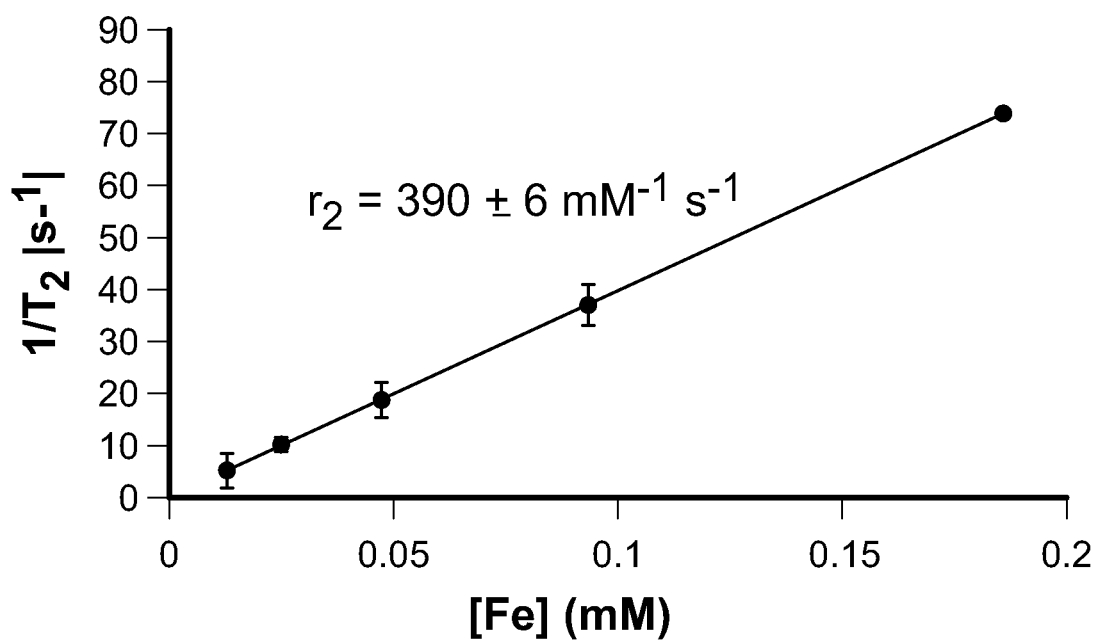
Figure 34C:
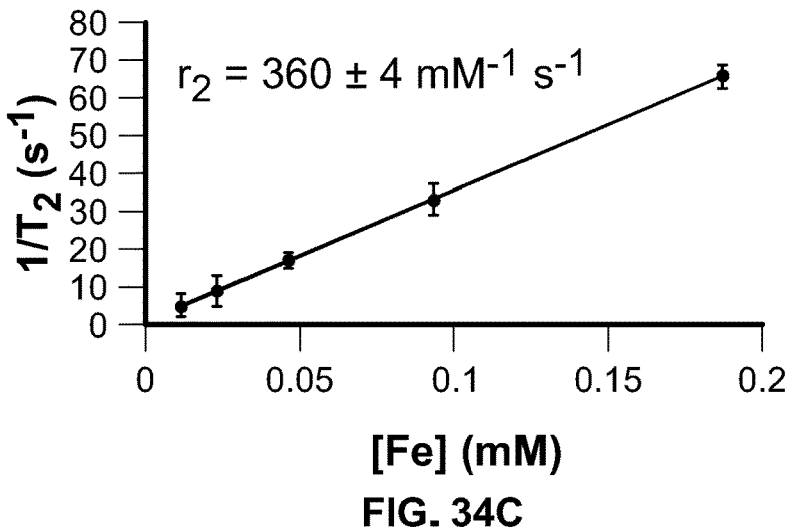

Affibody-targeted nanoclusters (FIG. 32A) were then prepared by simply mixing the HER2-DBCO with either the ISCs or the PSCs to produce HER2-targeted nanoclusters (HER2-ISCs and HER2-PSCs). ISCs-HER2 and PSCs-HER2 were found to be highly stable in water with no signs of aggregation or precipitation, as indicated by no significant changes in the $T_2$ relaxation time (FIG. 1C, FIG. 1B) or hydrodynamic diameter over the course of at least 6 days. Relaxometry measurements indicated an average $r_2$ value of 390±6 and 360±4 $mM^{-1}$ $s^{-1}$ for HER2-ISCs and HER2-PSCs, respectively (FIG. 32D, FIG. 34C).

Figure 35A:
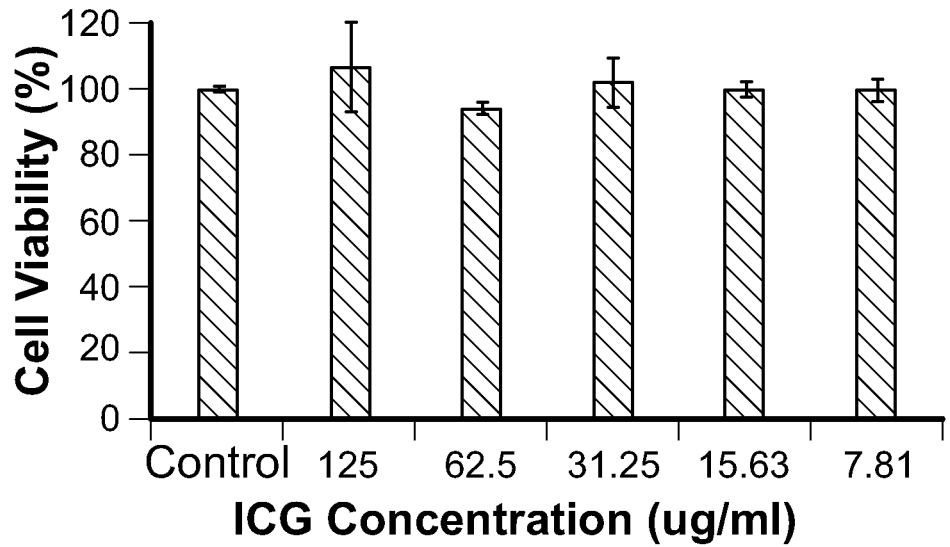
FIGS. 35A-35B graphically illustrate the viability of T617 cells after incubation with increasing concentrations of ISCs-HER2 (FIG. 35A) and PSCs-HER2 (FIG. 35B) for 24 h.
Figure 35B:
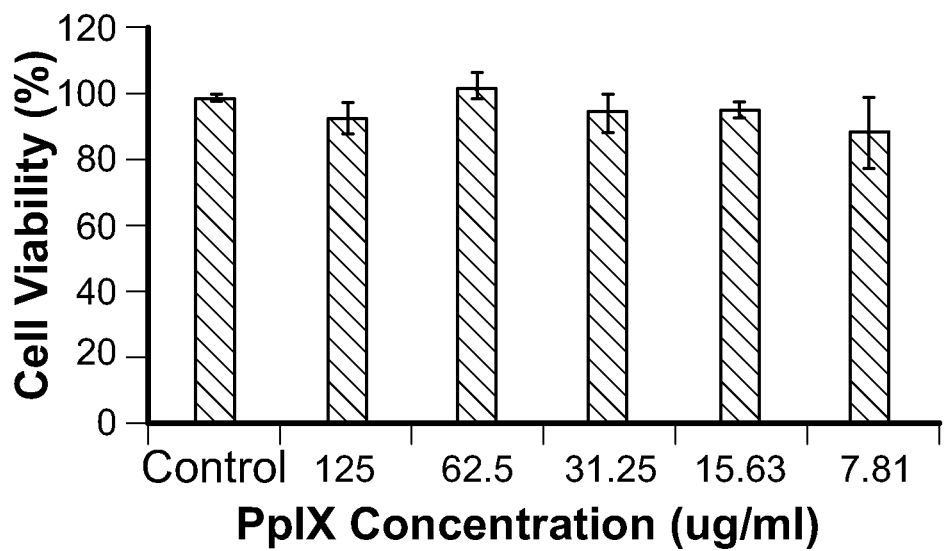
Figure 36:
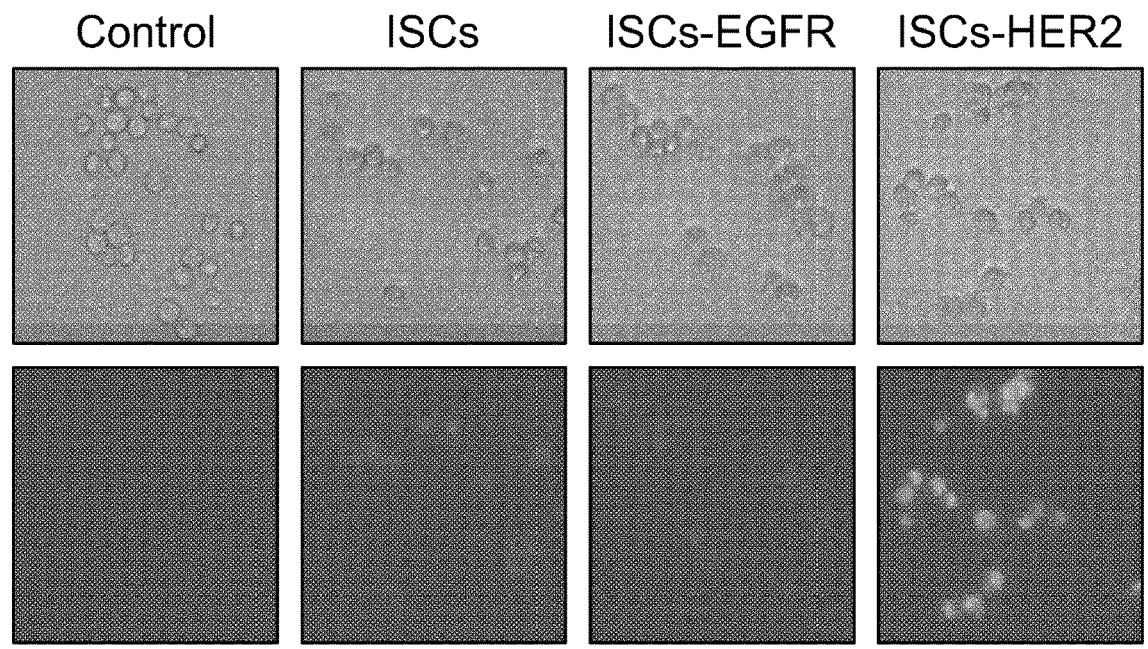
FIG. 36 shows phase contrast (top row) and fluorescence microscopy (bottom row) images of HER2/neu cells incubated without particles (control) and with ISCs, ISC-EGFR and
ISCs-HER2 for 1 hour.
Figure 37:
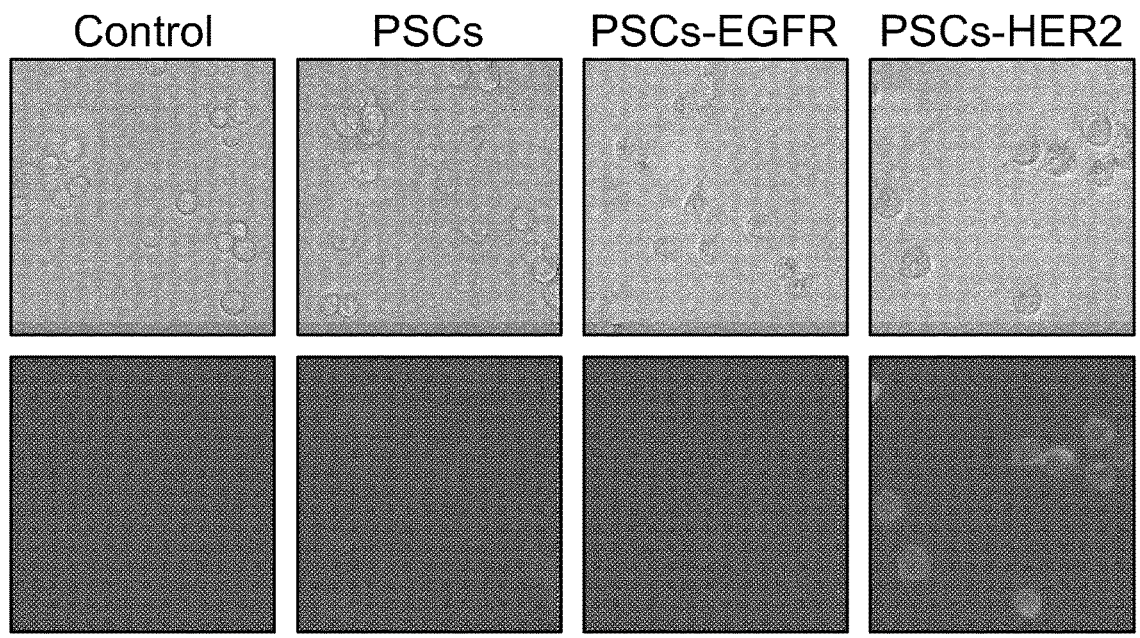
FIG. 37 shows phase contrast (top row) and fluorescence microscopy (bottom row) images of HER2/neu cells incubated without particles (control) and with PSCs, PSCs-EGFR and PSCs-HER2 for 1 hour.
Figure 38:
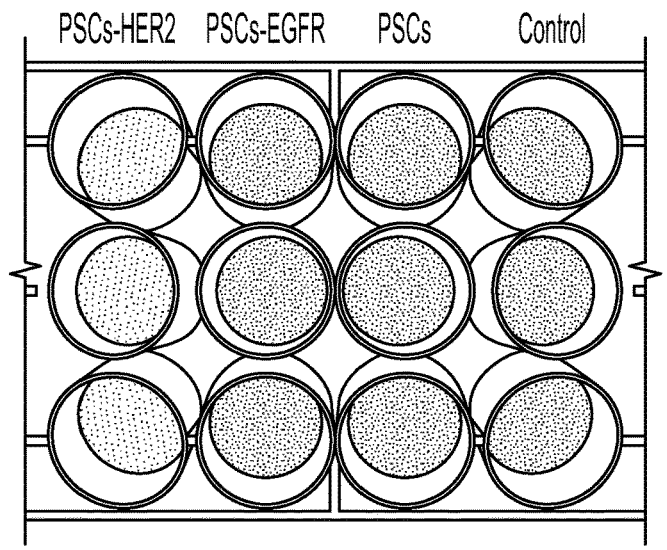
FIG. 38 shows visible detection of PSCs-HER2 binding with HER2/neu in 12 well-plate.

The cytotoxicity of the ISCs-1-1ER2 and PSCs-1-1ER2 were examined in an MTS cell proliferation assay. Increasing concentrations of targeted-nanoclusters were incubated with HER2/neu-positive (T6-17) breast cancer cells. It was found that the targeted-nanoclusters exhibited no obvious cytotoxicity to (FIGS. 35A-35B).

To investigate binding of the nanoclusters to target cells, HER2-ISCs-were incubated with T617 breast cancer cells for 1 hr incubation. The cells were then washed and imaged by phase contrast and fluorescence microscopy. Negative control studies were performed with ISCs that had not been functionalized with any targeting ligands as well as ISCs labeled with an anti-EGFR affibody. All studies were performed at equimolar concentrations of ICG (10 uM). Little to no cellular fluorescence was observed following incubation of T617 cells with either EGFR-ISCs or unlabeled ISCs. In contrast, a bright fluorescence signal was observed when T617 cells incubated with the HER2-ISCs Similar observations were made when T617 cells were incubated with HER2-PSCs and the analogous negative controls (Figure S3).

To confirm that the HER2 affibody-dye conjugate was not dissociating from the nanocluster, labeled T617 cells were also assessed by magnetic resonance. For these studies, all experiments were performed at equivalent concentrations of iron (100 μg/mL) and nanoclusters were incubated with cells for 1 hr.

Figure 33A:
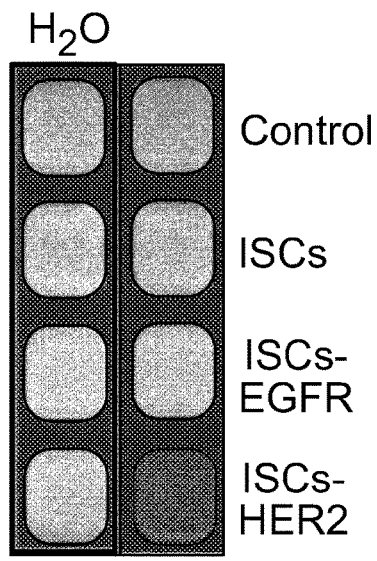
FIGS. 33A-33D MR phantom image of targeted and non-targeted ISCs after incubated with HER2/neu cells for 1 h (FIG. 33A). Relaxivity measurements of HER2/neu cells incubated with targeted and non-targeted nanocluster were acquired (FIG. 33B). MR phantom image and relaxivity measurements of HER2/neu with targeted and non-targeted PSCs (FIG. 33C) and (FIG. 33D), respectively
Figure 33B:
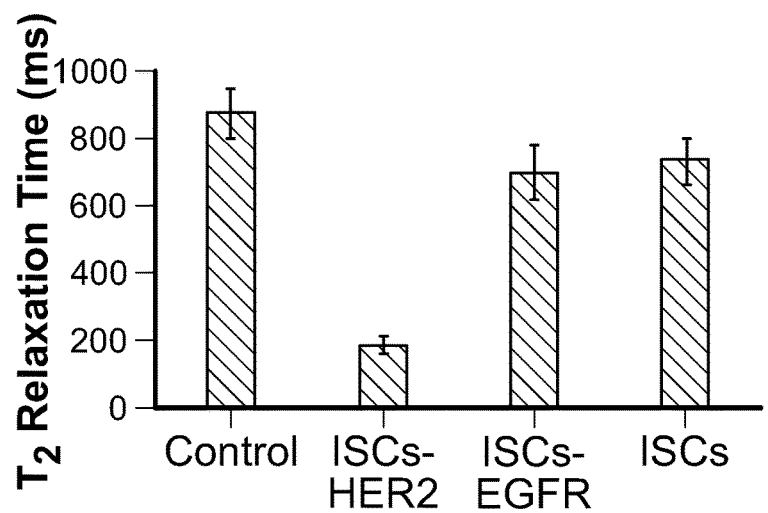
Figure 33C:
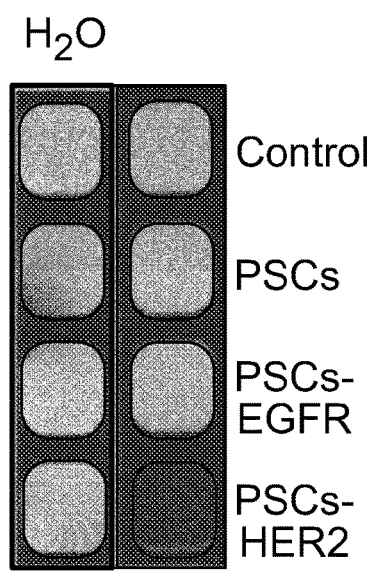
Figure 33D:
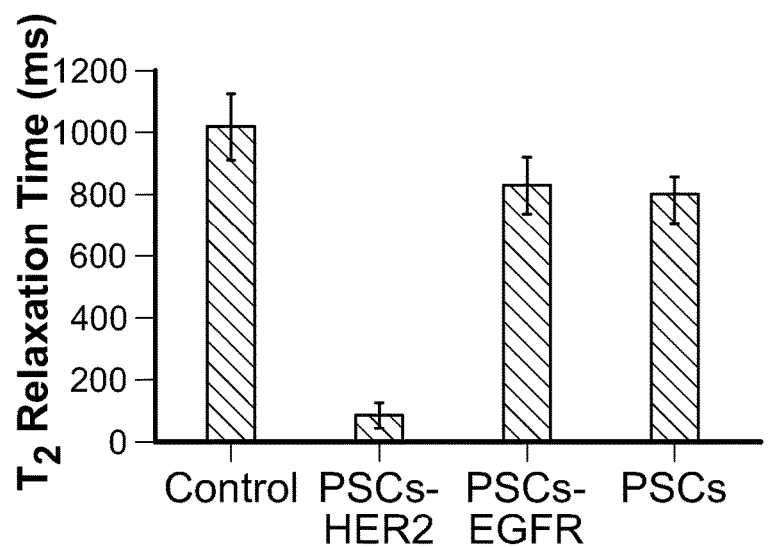

Only a slight reduction in the T2 relaxation time of T617 cells was observed following incubation with EGFR-ISCs and the non-targeted ISCs, indicative of little to no nonspecific binding (FIG. 33B). Similar results were observed with EGFR-PSCs and non-targeted PSCs (FIG. 33D). In contrast, the T617 cells that were incubated with the HER2-ISCs or HER2-PSCs exhibited a significantly lower $T_2$ relaxation time (FIG. 33B and FIG. 33D), consistent with the presence of SPION. MR images of a phantoms confirmed strong $T_2$ contrast relative to the negative controls (FIG. 33A and FIG. 33C). Therefore, these results provide clear evidence that antibodies-targeted nanoclusters specifically bind to HER2/neu-positive cells and the targeting ligands remains associated with the nanoclusters.

In summary, the inventors have demonstrated the ability to functionalize dye-stabilized nanoemulsions with targeting ligands. They have developed a versatile and easy-to-operate affibody conjugation method using click chemistry. These particles are highly stable, allow for high loading of dyes, and display high relaxivity. The affibody conjugation strategy, using catalyst-free click chemistry, can be applied to diverse applications such as molecular imaging, drug delivery, and photodynamic therapy.

Example 6

Ce6 Molecules Solubilized in Polymer Produce Stable Ce6 Nanoclusters

Materials

Polycaprolactone (PCL, Mn=10,000) was purchased from Sigma. Indocyanine green (ICG) was purchased from USP. Chlorin e6 (Ce6, MW=596.68) was purchased from Santa Cruz Biotechnology. All of the buffer solutions were prepared with deionized water.

Preparation of ICG and Ce6 Nanocluster

ICG or Ce6 was dissolved in DMSO at 20 mg/mL, and PCL was dissolved in toluene at a concentration of 50 mg/mL. A combined DMSO/toluene solution (200 μL) of the PCL (4 mg) and the ICG (2 mg) (or Ce6) was added directly to a glass vial containing 4 mL of Millipore water, and the mixture was sonicated for approximately 5 min in an ultrasonic bath. The emulsions were then allowed to stand overnight to evaporate toluene. The mixture was purified by dialysis (molecular weight cutoff: 3.5 kDa) against water for 36 h to remove free ICG or Ce6 and the trace amount of DMSO.

Figure 39:
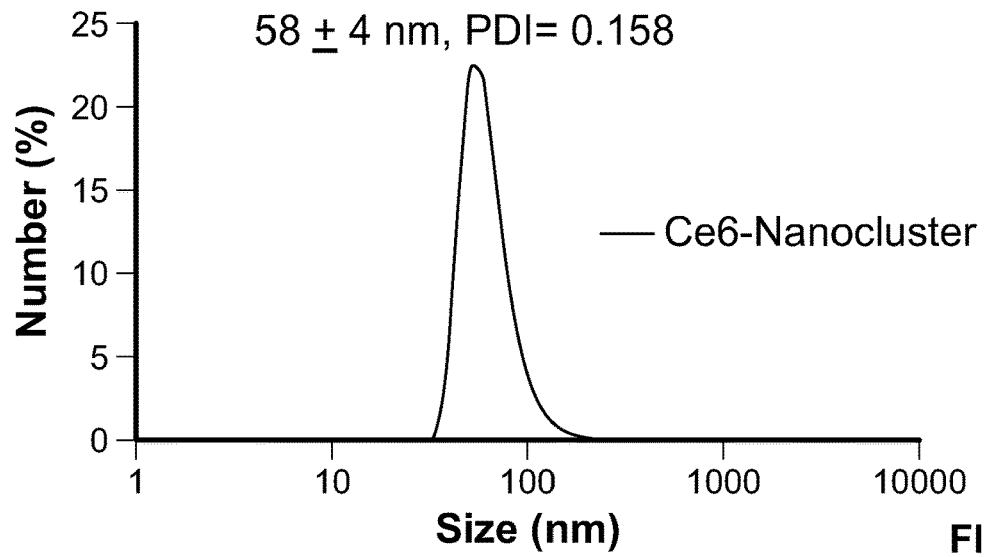
FIG. 39 shows the size distribution of Ce6 nanoclusters was measured by dynamic light scattering (DLS) in water at 25° C. The amphiphilic Ce6 molecules solubilized the PCL, creating stable nanoclusters with an average hydrodynamic diameter of 58±4 nm and an average polydispersity index (PDI) of <0.2.
Figure 40:
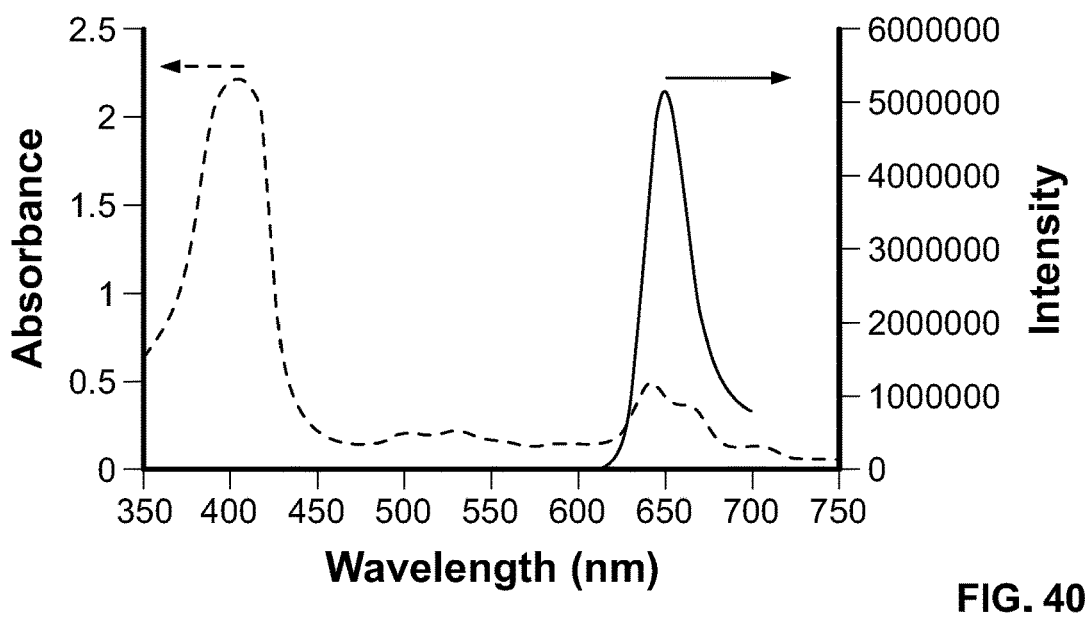
FIG. 40 shows UV-Vis absorbance and fluorescence emission spectra of Ce6 nanoclusters in DMSO. Fluorescence detection takes place when Ce6 is excited at around 404 nm, which then emits a characteristic ref fluorescence peak at approximately 650 nm.
Figure 43:
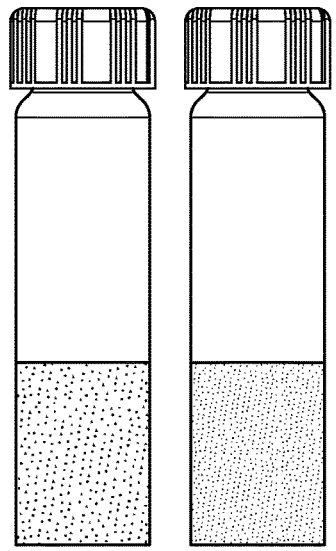
FIG. 43 is a photograph of vials containing solution with free Ce6 or Ce6 nanoclusters in water (at equal concentrations of Ce6). The amphiphilic Ce6 molecules solubilized the PCL in water and produce stable Ce6 nanoclusters. In contrast, the free Ce6 molecules aggregate and precipitate in water.

Results:

The size distribution of Ce6 nanoclusters was measured by dynamic light scattering (DLS) in water at 25° C. (FIG. 39). The amphiphilic Ce6 molecules solubilized the PCL, creating stable nanoclusters with an average hydrodynamic diameter of 58±4 nm and an average polydispersity index (PDI) of <0.2. Fluorescence detection takes place when Ce6 is excited at around 404 nm, which then emits a characteristic reference fluorescence peak at approximately 650 nm (FIG. 40). The amphiphilic Ce6 molecules solubilized the PCL in water and produce stable Ce6 nanoclusters; the free Ce6 molecules, by contrast, molecules aggregate and precipitate in water (FIG. 43).

Figure 41:
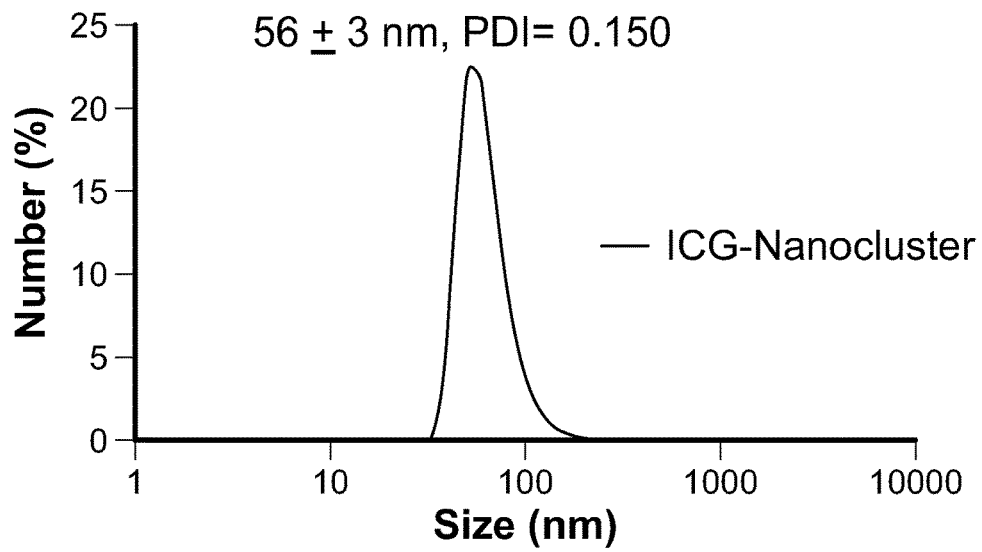
FIG. 41 shows the size distribution of the ICG nanoclusters was measured by dynamic light scattering (DLS) in water at 25° C. The amphiphilic ICG molecules solubilized the PCL, creating stable nanoclusters with an average hydrodynamic diameter of 56±3 nm and an average polydispersity index (PDI) of <0.2.
Figure 42:
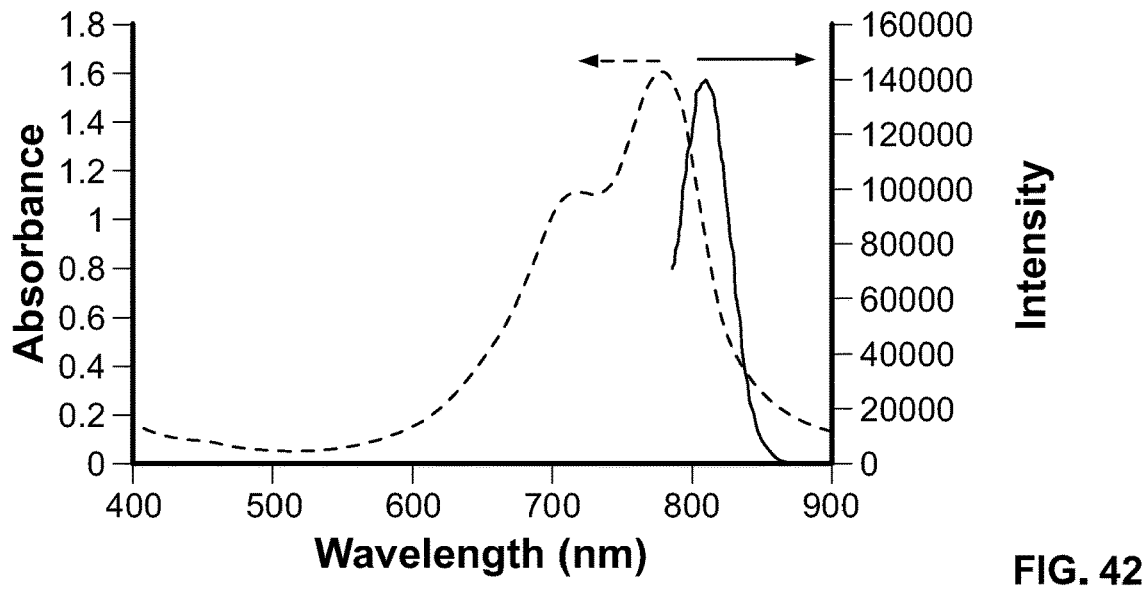
FIG. 42 shows UV-Vis absorbance and fluorescence emission spectra of ICG nanoclusters in DMSO. Fluorescence detection takes place when ICG is excited at around 780 nm, which then emits a fluorescence peak at approximately 810 nm.

The size distribution of the ICG nanoclusters was measured by dynamic light scattering (DLS) in water at 25° C. (FIG. 41). The amphiphilic ICG molecules solubilized the PCL, creating stable nanoclusters with an average hydrodynamic diameter of 56±3 nm and an average polydispersity index (PDI) of <0.2. Fluorescence detection takes place when ICG is excited at around 780 nm, which then emits a fluorescence peak at approximately 810 nm (FIG. 42).

Any patent, patent application publication, or scientific publication, cited herein, is incorporated by reference herein in its entirety.

The examples are presented in order to more fully illustrate embodiments of the invention. They should in no way be construed, however, as limiting the broad scope of the invention.

Having described preferred embodiments of the invention, it is to be understood that the invention is not limited to the precise embodiments, and that various changes and modifications may be effected therein by those skilled in the art without departing from the scope or spirit of the invention as defined in the appended claims.

What is claimed is:

1. A nanocluster comprising: a plurality of inorganic nanoparticles or of hydrophobic polymers, wherein said nanoparticles or said hydrophobic polymers are coated by one or more amphiphilic dyes, and wherein said one or more amphiphilic dyes are capable of solubilizing said nanoparticles or said hydrophobic polymers in an aqueous solvent.

2. The nanocluster according to claim 1, wherein said polymers are is a biodegradable polyester and wherein the biodegradable polyester is polylactic acid (PLA), polyglycolic acid (PGA), poly-ε-caprolactone (PCL), polyhydroxybutyrate (PHB), poly(3-hydroxy valerate)polycaprolactone, polyethylene succinate) (PESu), poly(propylene succinate) (PPSu) and poly(butylene succinate) (PBSu).

3. The nanocluster of claim 1, wherein said nanoparticles are metal nanoparticles, magnetic nanoparticles, nanophosphors, quantum dots, or a combination thereof.

4. The nanocluster according to claim 1, wherein said nanoparticles comprise doped or undoped iron oxide nanoparticles.

5. The nanocluster according to claim 1, wherein said nanoparticles comprise gold nanoparticles.

6. The nanocluster according to claim 1, wherein at least one of said one or more amphiphilic dyes is a cyanine dye, a cyclic tetrapyrrole, or a combination thereof.

7. The nanocluster according to claim 1, wherein the size of said nanocluster ranges from about 10 nm to about 750 nm.

8. The nanocluster according to claim 1, wherein said nanoparticles or polymers are coated with a ligand and wherein said ligand is oleic acid, oleylamine, dodecanethiol, or combinations thereof.

9. The nanocluster according to claim 1, further comprising at least one targeting agent on the surface of said nanocluster.

10. The nanocluster according to claim 1, further comprising a drug on the surface of said nanocluster, within a core of said nanocluster, dispersed throughout said nanocluster, or a combination thereof.

11. The nanocluster of claim 1, wherein the amphiphilic dye is a photosensitizer.

12. The nanocluster of claim 11, wherein the nanoparticles are superparamagnetic iron oxide nanoparticles (SPIONs).

13. The nanocluster of claim 11, wherein the photosensitizer is a chlorin.

14. A method for treating a cancer in a subject, the method comprising:
  (a) administering to said subject the nanocluster according to claim 1;
  (b) detecting said nanocluster by an imaging modality;
  (c) based on the detection, identifying a tumor associated with said cancer; and
  (d) treating said cancer.

15. A method for performing an image-guided surgery in a subject, the method comprising:
  (r) administering to said subject the nanocluster according to claim 1;
  (b) detecting said nanocluster by an imaging modality;
  (c) based on the detection, identifying a tissue that needs to be surgically removed; and
  (d) performing said surgery in said subject, and thereby performing said image-guided surgery in said subject.

16. A method for enhancing the effect of a radiation therapy in a subject, the method comprising:
  (a) administering to said subject the nanocluster according to claim 1;
  (b) detecting said nanocluster by an imaging modality;
  (c) based on the detection, identifying a target site; and
  (d) treating said subject with radiation at said identified target site,
  wherein the nanocluster increases the amount of radiation absorbed at said target site.

17. A method for ablating a tissue by a phototherapy in a subject, the method comprising:
  (a) administering to said subject the nanocluster according to claim 1;
  (b) detecting said nanocluster by an imaging modality;
  (c) based on the detection, identifying a target site; and
  (d) treating said subject with electromagnetic radiation at said target site,
  wherein the nanocluster absorbs the electromagnetic radiation and converts the electromagnetic radiation to heat, reactive oxygen species, or a combination thereof, to ablate the tissue at said target site.

18. An azide-functionalized nanocluster comprising the nanocluster of claim 11, wherein the amphiphilic dye is bioconjugated to an azide.

19. The azide-functionalized nanocluster of claim 18, wherein the amphiphilic dye is protoporphyrin IX (PpIX) or indocyanine green (ICG).

20. A targeting ligand comprising the azide-functionalized nanocluster of claim 19 conjugated to a targeting antibody.

21. A method for preparing a targeting antibody conjugated nanocluster, the method comprising:
  reacting by copper-free click chemistry (i) an azide-functionalized nanocluster comprising the nanocluster of claim 11, wherein the amphiphilic dye is bioconjugated to an azide, and the nanocluster is carrier-free; and (ii) a targeting antibody functionalized with a dibenzocyclooctyne (DBCO) group, wherein the DBCO group labels the azide, thereby conjugating the targeting antibody to the nanocluster.

22. The method of claim 21, further comprising washing the targeting antibody conjugated nanocluster to remove non-specifically bound targeting antibody, wherein the washing is a high stringency washing.

* * * * *